United States Patent
Mattoussi et al.

(10) Patent No.: US 10,294,213 B2
(45) Date of Patent: May 21, 2019

(54) CONTROLLING THE ARCHITECTURE, COORDINATION, AND REACTIVITY OF NANOPARTICLE COATING UTILIZING AN AMINO ACID CENTRAL SCAFFOLD

(71) Applicant: The Florida State University Research Foundation, Inc., Tallahassee, FL (US)

(72) Inventors: Hedi Mattoussi, Tallahassee, FL (US); Naiqian Zhan, Tallahassee, FL (US); Goutam Palui, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 190 days.

(21) Appl. No.: 15/366,316

(22) Filed: Dec. 1, 2016

(65) Prior Publication Data
US 2017/0168042 A1     Jun. 15, 2017

Related U.S. Application Data

(60) Provisional application No. 62/265,031, filed on Dec. 9, 2015, provisional application No. 62/268,574, filed on Dec. 17, 2015.

(51) Int. Cl.
C07C 271/22     (2006.01)
C07D 339/04     (2006.01)
(Continued)

(52) U.S. Cl.
CPC ............ C07D 339/04 (2013.01); A61K 49/00 (2013.01); C07C 271/22 (2013.01);
(Continued)

(58) Field of Classification Search
CPC .... C07C 271/22; C07D 339/04; A61K 49/00; C09K 11/025; C09K 11/58; C09K 11/883
See application file for complete search history.

(56) References Cited

U.S. PATENT DOCUMENTS 9,150,748 B1   10/2015   Mattoussi et al.
9,309,432 B1    4/2016   Mattoussi et al.
(Continued)

OTHER PUBLICATIONS

Zhan et al. Controlling the architecture, coordination, and reactivity of nanoparticle coating utilizing an amino acid central scaffold. J. Am. Chem. Soc. 2015, vol. 137, pp. 16084-16-97. (Year: 2015).*
(Continued)

*Primary Examiner* — Shafiqul Haq
(74) *Attorney, Agent, or Firm* — Armstrong Teasdale LLP

(57) ABSTRACT

A series of multicoordinating and multifunctional ligands optimized for the surface-functionalization of luminescent quantum dots (QDs) and gold nanoparticles (AuNPs) alike is disclosed. An L-aspartic acid precursor is modified with functionality, through simple peptide coupling chemistry, one or two lipoic acid (LA) groups and poly(ethylene glycol) (PEG) moieties in the same ligand. These ligands were combined with a new photoligation strategy to yield hydrophilic and reactive QDs that are colloidally stable over a broad range of conditions, including storage at nanomolar concentration and under ambient conditions.

11 Claims, 19 Drawing Sheets

(51) Int. Cl.
  A61K 49/00 (2006.01)
  C09K 11/02 (2006.01)
  C09K 11/58 (2006.01)
  C09K 11/88 (2006.01)
  G01N 33/53 (2006.01)
  G01N 33/58 (2006.01)
(52) U.S. Cl.
  CPC ............ *C09K 11/025* (2013.01); *C09K 11/58* (2013.01); *C09K 11/883* (2013.01)

(56) References Cited

U.S. PATENT DOCUMENTS

| | | |
|---|---|---|
| 9,598,635 B2 | 3/2017 | Mattoussi et al. |
| 2015/0284493 A1 | 10/2015 | Mattoussi et al. |
| 2015/0284517 A1 | 10/2015 | Mattoussi et al. |

OTHER PUBLICATIONS

Alivisatos, A.P., Semiconductor Clusters, Nanocrystals, and Quantum Dots, Science; Feb. 16, 1996, vol. 271, No. 5251; ProQuest; pp. 933-937.
Murray, C. B., et al., Synthesis and Characterization of Monodisperse Nanocrystals and Close-Packed Nanocrystal Assemblies, Annu. Rev. Mater. Sci, 2000, vol. 30 pp. 545-610.
Klimov, V.I. et al., Optical Gain and Stimulated Emission in Nanocrystal Quantum Dots, Science, Oct. 13, 2000, vol. 290, No. 5490; ProQuest, pp. 314-317.
Malko, A.V. et al., From amplified spontaneous emission to microring lasing using nanocrystal quantum dots solids, Applied Physcis Letters, Aug. 12, 2002, vol. 81, No. 7, pp. 1303-1305.
Nozik, A. J. et al., Semiconductor Quantum Dots and Quantum Dot Arrays and Applications of Multiple Exciton Generation to Third-Generation Photovoltaic Solar Cells, Chem. Rev., 2010, vol. 110, pp. 6873-6890.
Li Ling et al., Highly Efficient CdS Quantum Dot-Sensitized Solar Cells Based on a Modified Polysulfide Electrolyte, Journal of the American Chemical Society, 2011, vol. 133, pp. 8458-8460.
Raymo, Francisco M., et al., Luminescent chemosensors based on semiconductor quantum dots, Physical Chemistry Chemical Physics, Feb. 1, 2007, vol. 9, pp. 2036-2043.
Medintz, Igor L., et al., Quantum dot bioconjugates for imaging labelling and sensing, Nature Materials, Jun. 2005, vol. 4, pp. 435-446.
Michalet, X. et al., Quantum Dots for Live Cells, in Vivo Imaging, and Diagnostics, Science, Jan. 28, 2005, vol. 307, pp. 538-544.
Biju, Vasudevanpillai et al., Delivering quantum dots to cells: bioconjugated quantum dots for targeted and nonspecific extracellular and intracellular imaging, Chemical Society Reviews, May 27, 2010, vol. 39, pp. 3031-3056.
Zrazhevskiy, Paul et al., Designing multifunctional quantum dots for bioimaging, detection, and drug delivery, Chemical Society Reviews, Dec. 23, 2009, vol. 39, pp. 4326-4354.
Pinaud, Fabien et al., Probing cellular events, one quantum dot at a time, Nature Methods, Apr. 2010, vol. 7, No. 4, pp. 275-285.
Jaiswal, Jyoti K. et al., Long-term multiple color imaging of live cells using quantum dot bioconjugates, Nature Biotechnology, Jan. 2003, vol. 21, pp. 47-51.
Gao, Xiaohu, et al., In vivo cancer targeting and imaging with semiconductor quantum dots, Nature Biotechnology, Aug. 2004, vol. 22, No. 8, pp. 969-976.
Rossetti, R. et al., Size effects in the excited electronic states of small colloidal CdS crystallites, Journal of Chemical Physics, 1984, vol. 80, pp. 4464-4469.
Murray, C. B. et al., Synthesis and Characterization of Nearly Monodisperse CdE (E = S, Se, Te) Semiconductor Nanocrystallites, American Chemical Socity, 1993, vol. 115, pp. 8706-8715.
Dabbousi, B. O. et al., (CdSe)Zns Core-Shell Quantum Dots: Synthesis and Characterization of a Size Series of Highly Luminescent Nanocrystallites, 1997, vol. 101, pp. 9463-9475.
Liu, Wenhao et al., Compact Biocompatible Quantum Dots Functionalized for Cellular Imaging, Journal of American Chemical Society, 2008, vol. 130, pp. 1274-1284.
Susumu, Kimihiro et al., Multifunctional ligands based on dihydrolipoic acid and polyethylene glycol to promote biocompatibility of quantum dots, Nature Protocols, 2009, vol. 4, No. 3, pp. 424-436.
Jung, Jongjin et al., Selective Inhibition of Human Tumor Cells through Multifunctional Quantum-Dot-Based siRNA Delivery**, Angew. Chem. Inc. Ed., 2010, vol. 49, pp 103-107.
Liu, Wenhao et al., Compact Biocompatible Quantum Dots via RAFT-Mediated Synthesis of Imidazole-Based Random Copolymer Lignad, American Chemical Society, 2010, vol. 132, pp. 472-483.
Lee, Jae-Hyun et al., Artificially engineered magnetic nanoparticles for ultra-sensitive molecular imaging, Jan. 2007, vol. 13, No. 1, pp. 95-99.
Stewart, Michael H. et al., Multidentate Poly(ethylene glycol) Ligands Provide Colloidal Stability to Semiconductor and Metallic Nanocrystals in Extreme Conditions, Journal of American Chemical Society, 2010, vol. 132, pp. 9804-9813.
Muro, Eleonora et al., Small and Stable Sulfobetaine Zwitterionic Quantum Dots for Functional Live-Cell Imaging, Journal of American Chemical Society, 2010, vol. 132, pp. 4556-4557.
Lees, Emma E. et al., Experimental Determination of Quantum Dot Size Distributions, Ligand Packing Densities, an Bioconjugation Using Analytical Ultracentrifugation, American Chemical Society, 2008, vol. 8, No. 9, pp. 2883-2890.
Liu, Lu et al., Bifunctional Multidentate Ligand Modified Highly Stable Water-Soluble Quantum Dots, Inorganic Chemistry, American Chemical Society, 2010, vol. 49, pp. 3768-3775.
Clapp, Aaron R, et al., Capping of CdSe—ZnS quantum dots with DHLA and subsequent conjugation with proteins, Nature Protocols, 2006, vol. 1, No. 3, pp. 1258-1266.
Qu, Lianhua et al., Alternative Routes toward High Quality CdSe Nanocrystals, American Chemical Society, 2001, vol. 1, No. 6, pp. 333-337.
Mei, Bing C., Modular poly(ethylene glycol) ligands for biocompatible semiconductor and gold nanocrystals with extended pH and ionic stability, J, Mater. Chem., 2008, vol. 18, pp. 4949-4958.
Uyeda, Tetsuo H. et al., Synthesis of Compact Multidentate Ligands to Prepare Stable Hydrophilic Quantum Dot Fluorophores, Journal of American Chemical Society, 2005, vol. 127, pp. 3870-3878.
Choi, Chung Hang J., et al., Mechanism of active targeting in solid tumors with transferrin-containing gold nanoparticles, PNAS, Jan. 19, 2010, vol. 107, No. 3, 1235-1240.
Clapp, Aaron R. et al., Fluorescence Resonance Energy Transfer Between Quantum Dot Donors, Journal of American Chemical Society, 2004, vol. 126, pp. 301-310.
Medintz, Igor L., et al., Proteolytic activity monitored by fluorescence resonance energy transfer through quantum-dot-peptide conjugates, Nature Materials, Jul. 2006, vol. 5, pp. 581-589.
Chen, Chun-Yen et al., Potassium ion recognition by 15-crown-5 functionalized CdSe/ZnS quantum clots in H2O, Chem. Commun, 2006, pp. 263-265.
Susumu, Kimihiro et al., Colloidal Quantum Dots: Synthesis, Photophysical Properties, and Biofunctionalization Strategies, Atrech House, Aug. 25, 2008, pp. 1-26.
Hines, Margaret A., et al., Synthesis and Characterization of Strongly Luminescing ZnS-Capped CdSe Nanocrystals, J. Phys. Chem, American Chemical Society, 1996, vol. 100, No. 2, pp. 468-471.
van Embden, Joel et al., Mapping the Optical Properties of CdSe/CdS Heterostructure Nanocrystals: The Effects of Core Size and Shell Thickness, Journal of American Chemical Society, 2009, vol. 131, pp. 14299-14309.
Gerion, Daniele, et al., Synthesis and Properties of Biocompatible Water-Soluble Silica-Coated CdSe/ZnS Semicondutor Quantum Dots, J. Phys. Chem. B, 2001, vol. 105, pp. 8861-8871.
Bhang, Suk Ho et al., Hyaluronic Acid-Quantum Dot Conjugates for In Vivo Lymphatic Vessel Imaging, American Chemical Society, May 28, 2009, vol. 3, No. 6, pp. 1389-1398.

(56) References Cited

OTHER PUBLICATIONS

Yildiz, Ibrahim et al., Biocompatible CdSe—ZnS Core-Shell Quantum Dots Coated with Hydrophilic Polythiols, American Chemical Society, 2009, vol. 25, No. 12, pp. 7090-7096.

Yildiz, Ibrahim et al,, Biocompatibie CdSe—Zn Core-Shell Quantum Dots with Reactive Function Groups on Their Surface, Langmuir, 2010, vol. 26, No. 13, pp. 11503-11511.

Shen, Hongyan et al., Poly(ethylerie glycol) Carbondiimide Coupling Reagents for the Biological and Chemical Functionalization of Water-Soluble Nanoparticles, American Chemical Society, 2009, vol. 3, No. 4, pp. 915-923.

Anderson, Robin E. et al., Systematic Investigation of Preparing Biocompatible, Single, and Small ZnS-Capped CdSe Quantum Dots with Amphiphilic Polymers, American Chemical Society, 2006, vol. 2; No. 7, pp. 1341-1352.

Bullen, C. et al., The Effects of Chemisorption on the Luminescence of CdSe Quantum Dots, Langmuir, 2006, vol. 22, pp. 3007-3013.

Munro, Andrea M. et al., Quantitative Study of the Effects of Surface Ligand Concentration on CdSe Nanocrystal Photoluminescence, J. Phys. Chem. C, 2007, vol. 111, pp. 6220-6227.

Mei, Bing C. et al., Effects of Ligand Coordination Number and Surface Curvature on the Stability of Gold Nanoparticles in Aqueous Solutions, Langmuir, American Chemical Society, 2009, vol. 25, No. 18, pp. 10604-10611.

Na, Hyon Bin et al., Multidentate Catechol-Based Polyethylene Glycol Oligomers Provide Enhanced Stability and Biocompatibility to Iron Oxide Nanoparticles, American Chemical Society, 2012, vol. 6, No. 1, pp. 389-399.

\* cited by examiner

CONTROLLING THE ARCHITECTURE, COORDINATION, AND REACTIVITY OF NANOPARTICLE COATING UTILIZING AN AMINO ACID CENTRAL SCAFFOLD

CROSS REFERENCE TO RELATED APPLICATIONS

This application claims priority to U.S. provisional application Ser. No. 62/265,031, filed Dec. 9, 2015, the contents of which are hereby incorporated by reference as if set forth in its entirety. This application claims priority to U.S. provisional application Ser. No. 62/268,574, filed Dec. 17, 2015, the contents of which are hereby incorporated by reference as if set forth in its entirety.

STATEMENT REGARDING FEDERALLY SPONSORED RESEARCH OR DEVELOPMENT

This invention was made with Government support under Grant Nos. NSF-CHE #1508501 and NSF-CHE #1058957 awarded by the National Science Foundation. The Government has certain rights in the invention.

FIELD OF THE INVENTION

The present invention relates to a method for preparing a series of multicoordinating and multifunctional ligands optimized for the surface-functionalization of luminescent quantum dots (QDs) and gold nanoparticles (AuNPs) alike.

BACKGROUND OF THE INVENTION

In the past decade, inorganic nanocrystals, specifically gold nanoparticles (AuNPs) and semiconductor quantum dots (QDs), have generated great interest for applications in several areas of biology and medicine. See References 1 through 18. This stems from their unique sets of physical and chemical properties that exhibit size-, shape- and composition-dependence. For example, metallic AuNPs show size- and shape-dependent Surface Plasmon Resonance (SPR) absorption ranging from the visible to the near-infrared (NIR). See References 19 through 24. Similarly, some of the properties of semiconductor QDs including broad excitation, narrow and tunable emission across the visible and near-IR spectrum, high two-photon action cross-section and superior chemical stability account for their widespread applications as biological tagging and sensing agents. See References 3, 7, and 25 through 29. However, typical synthesis of high quality QDs (via "hot injection" routes) with narrow size distribution and control over size and core crystallinity provides nanocrystals that are capped with hydrophobic organic ligands. See References 30 through 36. These materials are exclusively soluble in hydrophobic solvents (such as toluene or hexane); this limits one's ability to integrate them with biomolecules, or introduce them into live cells. Therefore, an additional surface-modification with tailor-made ligands is required to render the nanocrystals stable in buffer media and biocompatible. See References 14 and 37 through 39.

Several strategies including silica coating, encapsulation, and ligand exchange have been reported for preparing biocompatible QDs. See References 40 through 53. Among those routes, ligand exchange which relies on the substitution of the native surface cap with hydrophilic coordinating ligands offers a few key advantages. This strategy is easy to implement and provides compact nanocrystals in aqueous media. It also permits easy introduction of specific reactive functionalities on the nanocrystal surfaces, for further modification with target biomolecules. See References 41, 45, 46, 49, and 54 through 57. Several modular ligands bearing thiol, amine, pyridine and imidazole as anchoring groups have been recently documented in the literature. See References 58 through 61. Among these, multidentate thiolated ligands, such as derivatives of dihydrolipoic acid (DHLA), provide enhanced colloidal stability of QDs (e.g., CdSe—ZnS) in aqueous media compared with those presenting monodentate coordinating groups, due to the strong affinity of thiol to the zinc-rich QD surface and higher coordination of dithiol groups. Over the past decade, a variety of DHLA-based ligands have been synthesized and tested, confirming the benefits of cooperative coordination onto the ZnS-overcoated QDs. See References 46, 50, 51, 60, and 62 through 65. The enhanced binding affinity of multithiol-appended ligands to AuNPs and AuNRs have also been reported. See References 66 through 68. To further exploit these effects, several groups have explored the possibility of using polymeric ligands instead, even though these can increase the hydrodynamic size of nanoparticles in buffer media. See References 41, 46, 48, 55, and 61. One of the challenges in designing the ligands (either polymeric or molecular scale) is the versatility and scalability of the synthetic scheme. Specifically, factors that need to be taken into consideration include the design of ligands with multiple functionalities and the use of versatile and scalable reaction schemes.

The following articles are referenced herein as if set forth in their entirety:

(1) Chan, W. C. W.; Nie, S. M. *Science* 1998, 281, 2016.

(2) Bruchez, M.; Moronne, M.; Gin, P.; Weiss, S.; Alivisatos, A. P. *Science* 1998, 281, 2013.

(3) Alivisatos, P. *Nature Biotechnology* 2004, 22, 47.

(4) Kim, S.; Lim, Y.; Soltesz, E.; De Grand, A.; Lee, J.; Nakayama, A.; Parker, J.; Mihaljevic, T.; Laurence, R.; Dor, D.; Cohn, L.; Bawendi, M.; Frangioni, J. *Nature Biotechnology* 2004, 22, 93.

(5) Michalet, X.; Pinaud, F.; Bentolila, L.; Tsay, J.; Doose, S.; Li, J.; Sundaresan, G.; Wu, A.; Gambhir, S.; Weiss, S. *Science* 2005, 307, 538.

(6) El-Sayed, I. H.; Huang, X. H.; El-Sayed, M. A. *Nano Lett* 2005, 5, 829.

(7) Medintz, I.; Uyeda, H.; Goldman, E.; Mattoussi, H. *Nature Materials* 2005, 4, 435.

(8) Chithrani, B. D.; Ghazani, A. A.; Chan, W. C. W. *Nano Lett* 2006, 6, 662.

(9) Huang, X. H.; El-Sayed, I. H.; Qian, W.; El-Sayed, M. A. *J Am Chem Soc* 2006, 128, 2115.

(10) Murphy, C. J.; Gole, A. M.; Stone, J. W.; Sisco, P. N.; Alkilany, A. M.; Goldsmith, E. C.; Baxter, S. C. *Accounts of Chemical Research* 2008, 41, 1721.

(11) Ghosh, P.; Han, G.; De, M.; Kim, C. K.; Rotello, V. M. *Adv Drug Deliver Rev* 2008, 60, 1307.

(12) You, C. J.; Wilmes, S.; Beutel, O.; Lochte, S.; Podoplelowa, Y.; Roder, F.; Richter, C.; Seine, T.; Schaible, D.; Uze, G.; Clarke, S.; Pinaud, F.; Dahan, M.; Piehler, J. *Angewandte Chemie—International Edition* 2010, 49, 4108.

(13) Pinaud, F.; Clarke, S.; Sittner, A.; Dahan, M. *Nat Methods* 2010, 7, 275.

(14) Mattoussi, H.; Palui, G.; Na, H. B. *Adv Drug Deliver Rev* 2012, 64, 138.

(15) Weintraub, K. *Nature* 2013, 495, S14.

(16) Cai, E.; Ge, P.; Lee, S. H.; Jeyifous, O.; Wang, Y.; Liu, Y.; Wilson, K. M.; Lim, S. J.; Baird, M. A.; Stone, J. E.; Lee, K. Y.; Davidson, M. W.; Chung, H. J.; Schulten, K.;

Smith, A. M.; Green, W. N.; Selvin, P. R. *Angewandte Chemie International Edition* 2014, 53, 12484.

(17) Howes, P. D.; Chandrawati, R.; Stevens, M. M. *Science* 2014, 346.

(18) Rana, S.; Le, N. D. B.; Mout, R.; Saha, K.; Tonga, G. Y.; Bain, R. E. S.; Miranda, O. R.; Rotello, C. M.; Rotello, V. M. *Nat Nanotechnol* 2015, 10, 65.

(19) Mie, G. *Ann Phys-Berlin* 1908, 25, 377.

(20) Jana, N. R.; Gearheart, L.; Murphy, C. J. *The Journal of Physical Chemistry B* 2001, 105, 4065.

(21) Kelly, K. L.; Coronado, E.; Zhao, L. L.; Schatz, G. C. *J Phys Chem B* 2003, 107, 668.

(22) Gole, A.; Murphy, C. J. *Chemistry of Materials* 2005, 17, 1325.

(23) Liz-Marzan, L. M. *Langmuir* 2006, 22, 32.

(24) Jain, P. K.; Lee, K. S.; El-Sayed, I. H.; El-Sayed, M. A. *The Journal of Physical Chemistry B* 2006, 110, 7238.

(25) Jaiswal, J. K.; Mattoussi, H.; Mauro, J. M.; Simon, S. M. *Nature Biotechnology* 2003, 21, 47.

(26) C. B. Murray, C. R. K., M. G. Bawendi *Ann. Rev. Mater. Sci.* 2000, 30, 545.

(27) Talapin, D. V.; Lee, J. S.; Kovalenko, M. V.; Shevchenko, E. V. *Chemical Reviews* 2010, 110, 389.

(28) Resch-Genger, U.; Grabolle, M.; Cavaliere-Jaricot, S.; Nitschke, R.; Nann, T. *Nat Meth* 2008, 5, 763.

(29) Larson, D. R.; Zipfel, W. R.; Williams, R. M.; Clark, S. W.; Bruchez, M. P.; Wise, F. W.; Webb, W. W. *Science* 2003, 300, 1434.

(30) Talapin, D. V.; Rogach, A. L.; Komowski, A.; Haase, M.; Weller, H. *Nano Lett* 2001, 1, 207.

(31) Reiss, P.; Bleuse, J.; Pron, A. *Nano Lett* 2002, 2, 781.

(32) Peng, Z. A.; Peng, X. G. *J Am Chem Soc* 2001, 123, 183.

(33) Murray, C. B.; Norris, D. J.; Bawendi, M. G. *J Am Chem Soc* 1993, 115, 8706.

(34) Hines, M. A.; Guyot-Sionnest, P. *Journal of Physical Chemistry* 1996, 100, 468.

(35) Dabbousi, B. O.; Rodriguez Viejo, J.; Mikulec, F. V.; Heine, J. R.; Mattoussi, H.; Ober, R.; Jensen, K. F.; Bawendi, M. G. *J Phys Chem B* 1997, 101, 9463

(36) Reiss, P.; Protiere, M.; Li, L. *Small* 2009, 5, 154.

(37) Sapsford, K. E.; Algar, W. R.; Berti, L.; Gemmill, K. B.; Casey, B. J.; Oh, E.; Stewart, M. H.; Medintz, I. L. *Chemical Reviews* 2013, 113, 1904.

(38) Nam, J.; Won, N.; Bang, J.; Jin, H.; Park, J.; Jung, S.; Jung, S.; Park, Y.; Kim, S. *Adv Drug Deliver Rev* 2013, 65, 622.

(39) Tyrakowski, C. M.; Snee, P. T. *Physical Chemistry Chemical Physics* 2014, 16, 837.

(40) Liu, D.; Snee, P. T. *ACS Nano* 2011, 5, 546.

(41) Giovanelli, E.; Muro, E.; Sitbon, G.; Hanafi, M.; Pons, T.; Dubertret, B.; Lequeux, N. *Langmuir* 2012, 28, 15177.

(42) Yi, D. K.; Selvan, S. T.; Lee, S. S.; Papaefthymiou, G. C.; Kundaliya, D.; Ying, J. Y. *J Am Chem Soc* 2005, 127, 4990.

(43) Gerion, D.; Pinaud, F.; Williams, S. C.; Parak, W. J.; Zanchet, D.; Weiss, S.; Alivisatos, A. P. *The Journal of Physical Chemistry B* 2001, 105, 8861.

(44) Dubertret, B.; Skourides, P.; Norris, D. J.; Noireaux, V.; Brivanlou, A. H.; Libchaber, A. *Science* 2002, 298, 1759.

(45) Susumu, K.; Uyeda, H. T.; Medintz, I. L.; Pons, T.; Delehanty, J. B.; Mattoussi, H. *J Am Chem Soc* 2007, 129, 13987.

(46) Liu, W. H.; Greytak, A. B.; Lee, J.; Wong, C. R.; Park, J.; Marshall, L. F.; Jiang, W.; Curtin, P. N.; Ting, A. Y.; Nocera, D. G.; Fukumura, D.; Jain, R. K.; Bawendi, M. G. *J Am Chem Soc* 2010, 132, 472.

(47) Snee, P. T.; Somers, R. C.; Nair, G.; Zimmer, J. P.; Bawendi, M. G.; Nocera, D. G. *J Am Chem Soc* 2006, 128, 13320.

(48) Yildiz, I.; McCaughan, B.; Cruickshank, S. F.; Callan, J. F.; Raymo, F. M. *Langmuir* 2009, 25, 7090.

(49) Mei, B. C.; Susumu, K.; Medintz, I. L.; Delehanty, J. B.; Mountziaris, T. J.; Mattoussi, H. *J Mater Chem* 2008, 18, 4949.

(50) Uyeda, H. T.; Medintz, I. L.; Jaiswal, J. K.; Simon, S. M.; Mattoussi, H. *J Am Chem Soc* 2005, 127, 3870.

(51) Muro, E.; Fragola, A.; Pons, T.; Lequeux, N.; Ioannou, A.; Skourides, P.; Dubertret, B. *Small* 2012, 8, 1029.

(52) Palui, G.; Aldeek, F.; Wang, W. T.; Mattoussi, H. *Chemical Society Reviews* 2015, 44, 193.

(53) Pellegrino, T.; Manna, L.; Kudera, S.; Liedl, T.; Koktysh, D.; Rogach, A. L.; Keller, S.; Radler, J.; Natile, G.; Parak, W. J. *Nano Lett* 2004, 4, 703.

(54) Susumu, K.; Mei, B. C.; Mattoussi, H. *Nature Protocols* 2009, 4, 424.

(55) Yildiz, I.; Deniz, E.; McCaughan, B.; Cruickshank, S. F.; Callan, J. F.; Raymo, F. M. *Langmuir* 2010, 26, 11503.

(56) Muro, E.; Pons, T.; Lequeux, N.; Fragola, A.; Sanson, N.; Lenkei, Z.; Dubertret, B. *J Am Chem Soc* 2010, 132, 4556.

(57) Zhang, P.; Liu, S.; Gao, D.; Hu, D.; Gong, P.; Sheng, Z.; Deng, J.; Ma, Y.; Cai, L. *J Am Chem Soc* 2012, 134, 8388.

(58) Susumu, K.; Oh, E.; Delehanty, J. B.; Pinaud, F.; Gemmill, K. B.; Walper, S.; Breger, J.; Schroeder, M. J.; Stewart, M. H.; Jain, V.; Whitaker, C. M.; Huston, A. L.; Medintz, I. L. *Chemistry of Materials* 2014, 26, 5327.

(59) Wang, W.; Kapur, A.; Ji, X.; Safi, M.; Palui, G.; Palomo, V.; Dawson, P. E.; Mattoussi, H. *J Am Chem Soc* 2015, 137, 5438.

(60) Liu, W.; Howarth, M.; Greytak, A. B.; Zheng, Y.; Nocera, D. G.; Ting, A. Y.; Bawendi, M. G. *J Am Chem Soc* 2008, 130, 1274.

(61) Viswanath, A.; Shen, Y.; Green, A. N.; Tan, R.; Greytak, A. B.; Benicewicz, B. C. *Macromolecules* 2014, 47, 8137.

(62) Mattoussi, H.; Mauro, J. M.; Goldman, E. R.; Anderson, G. P.; Sundar, V. C.; Mikulec, F. V.; Bawendi, M. G. *J Am Chem Soc* 2000, 122, 12142.

(63) Gravel, E.; Tanguy, C.; Cassette, E.; Pons, T.; Knittel, F.; Bernards, N.; Garofalakis, A.; Duconge, F.; Dubertret, B.; Doris, E. *Chemical Science* 2013, 4, 411.

(64) Stewart, M. H.; Susumu, K.; Mei, B. C.; Medintz, I. L.; Delehanty, J. B.; Blanco-Canosa, J. B.; Dawson, P. E.; Mattoussi, H. *J Am Chem Soc* 2010, 132, 9804.

(65) Zhan, N.; Palui, G.; Grise, H.; Tang, H.; Alabugin, I.; Mattoussi, H. *ACS Applied Materials & Interfaces* 2013, 5, 2861.

(66) Oh, E.; Susumu, K.; Goswami, R.; Mattoussi, H. *Langmuir* 2010, 26, 7604.

(67) Chen, X. J.; Lawrence, J.; Parelkar, S.; Emrick, T. *Macromolecules* 2013, 46, 119.

(68) Mei, B. C.; Oh, E.; Susumu, K.; Farrell, D.; Mountziaris, T. J.; Mattoussi, H. *Langmuir* 2009, 25, 10604.

(69) Palui, G.; Avellini, T.; Zhan, N.; Pan, F.; Gray, D.; Alabugin, I.; Mattoussi, H. *J Am Chem Soc* 2012, 134, 16370.

(70) Zhan, N. Q.; Palui, G.; Safi, M.; Ji, X.; Mattoussi, H. *J Am Chem Soc* 2013, 135, 13786.

(71) Mei, B. C.; Susumu, K.; Medintz, I. L.; Mattoussi, H. *Nature Protocols* 2009, 4, 412.

(72) Isaacs, S. R.; Cutler, E. C.; Park, J. S.; Lee, T. R.; Shon, Y. S. *Langmuir* 2005, 21, 5689.

(73) Daniels, T. R.; Delgado, T.; Rodriguez, J. A.; Helguera, G.; Penichet, M. L. *Clin Immunol* 2006, 121, 144.

(74) Lowe, S. B.; Dick, J. A. G.; Cohen, B. E.; Stevens, M. M. *Acs Nano* 2012, 6, 851.

(75) Silvi, S.; Credi, A. *Chemical Society Reviews* 2015, 44, 4275.

(76) Medintz, I. L.; Stewart, M. H.; Trammell, S. A.; Susumu, K.; Delehanty, J. B.; Mei, B. C.; Melinger, J. S.; Blanco-Canosa, J. B.; Dawson, P. E.; Mattoussi, H. *Nature Materials* 2010, 9, 676.

(77) Chung, E. Y.; Ochs, C. J.; Wang, Y.; Lei, L.; Qin, Q.; Smith, A. M.; Strongin, A. Y.; Kamm, R.; Qi, Y.-X.; Lu, S.; Wang, Y. *Nano Lett* 2015, 15, 5025.

(78) Mattoussi, H.; Cumming, A. W.; Murray, C. B.; Bawendi, M. G.; Ober, R. *Phys Rev B* 1998, 58, 7850.

(79) Leatherdale, C. A.; Woo, W. K.; Mikulec, F. V.; Bawendi, M. G. *J Phys Chem B* 2002, 106, 7619.

(80) Clapp, A. R.; Medintz, I. L.; Mauro, J. M.; Fisher, B. R.; Bawendi, M. G.; Mattoussi, H. *J Am Chem Soc* 2004, 126, 301.

(81) Palui, G.; Na, H. B.; Mattoussi, H. *Langmuir* 2012, 28, 2761.

(82) Susumu, K.; Oh, E.; Delehanty, J. B.; Blanco-Canosa, J. B.; Johnson, B. J.; Jain, V.; Hervey, W. J.; Algar, W. R.; Boeneman, K.; Dawson, P. E.; Medintz, I. L. *J Am Chem Soc* 2011, 133, 9480.

(83) Yu, W. W.; Peng, X. G. *Angewandte Chemie—International Edition* 2002, 41, 2368.

(84) Ojea-Jimenez, I.; Garcia-Fernandez, L.; Lorenzo, J.; Puntes, V. F. *ACS Nano* 2012, 6, 7692.

(85) Schnolzer, M.; Alewood, P.; Jones, A.; Alewood, D.; Kent, S. B. H. *Int J Pept Prot Res* 1992, 40, 180.

SUMMARY OF THE INVENTION

Among the various aspects of the present invention may be noted a versatile strategy to prepare a series of multicoordinating and multifunctional ligands optimized for the surface-functionalization of luminescent quantum dots (QDs) and metallic, e.g., gold, nanoparticles (AuNPs) alike. The chemical design of the present disclosure relies on the modification of L-aspartic acid precursor to controllably combine, through simple peptide coupling chemistry, one or two lipoic acid (LA) groups and poly(ethylene glycol) (PEG) moieties in the same ligand. In some embodiments, this route has provided two sets of modular ligands: (i) bis(LA)-PEG which presents two lipoic acids (higher coordination) appended onto a single end-functionalized PEG, and (ii) LA-(PEG)$_2$ made of two PEG moieties (higher branching, with various end reactive groups) appended onto a single lipoic acid. These ligands were combined with a new photoligation strategy to yield hydrophilic and reactive QDs that are colloidally stable over a broad range of conditions, including storage at nanomolar concentration and under ambient conditions. Metal nanoparticles, e.g., AuNPs, capped with these ligands also exhibited excellent stability in various biological conditions and improved resistance against NaCN digestion. This route also provided compact nanocrystals with tunable surface reactivity. As such, according to some embodiments of the present disclosure, QDs capped with bis(LA)-PEG-COOH are covalently coupled to transferrin to facilitate intracellular uptake. The coupling of dye-labeled peptides to QD surfaces may be characterized and quantified using fluorescence resonance energy transfer interactions in QD-peptide-dye assemblies.

In one aspect, the present invention is therefore directed to a compound having the general structure (I):

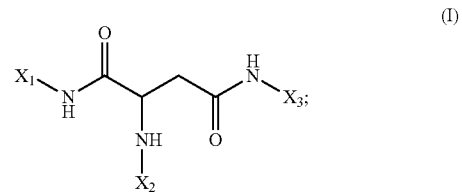

wherein $X_1$, $X_2$, and $X_3$ are each independently selected from the group consisting of hydrogen —H, hydroxyl —OH,

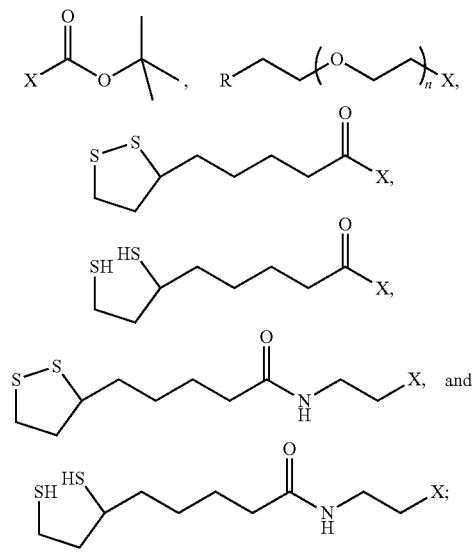

wherein at least one of $X_1$, $X_2$, and $X_3$ are selected from the group consisting of:

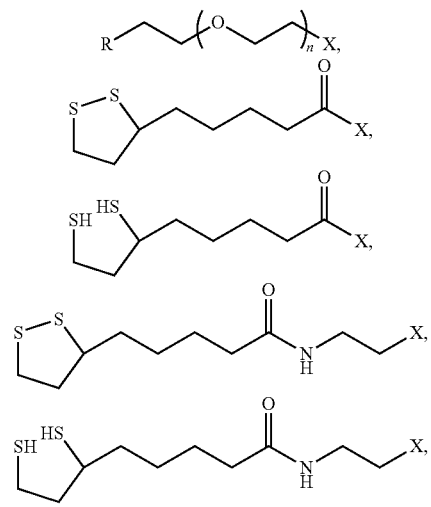

and any combination thereof;
wherein R is selected from the group consisting of hydrogen —H, hydroxyl —OH, methoxy —OCH$_3$, methoxy —OCH$_3$, azido —N$_3$, and —NR$_1$R$_2$, wherein R$_1$ and R$_2$ are independently selected from the group consisting of hydrogen —H, 4-oxopentanoic acid

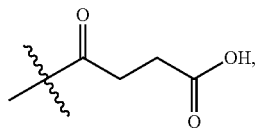 [SMILES: *C(=O)CCC(=O)O]

and 4-acetylbenzaldehyde

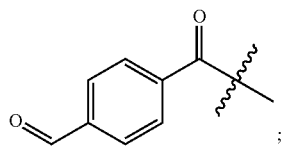

and wherein each n has a value between 3 and about 20.

In another aspect, the present invention is further directed to a composition comprising: a nanoparticle comprising a material selected from the group consisting of Fe$_3$O$_4$, Fe$_2$O$_3$, FePt, Co, Mn-doped Fe$_3$O$_4$, CdSe/ZnS, InP/ZnS, PbS, CdTe, CoPt, FeCoPt, CoFe$_2$O$_4$, MnO, Mn$_3$O$_4$, Co$_3$O$_4$, FeO, Ni, TiO$_2$, Al$_2$O$_3$, CdSe, PbSe, ZrO$_2$, ZnO, Au, Ag, and graphene oxide; and a capping layer comprising the above described compound.

In yet another aspect, the present invention is still further directed to a composition comprising: a nanoparticle comprising a material selected from the group consisting of silicon, germanium, tin, silicon carbide, selenium, tellurium, boron nitride, boron phosphide, boron arsenide, aluminum nitride, gallium nitride, gallium arsenide, indium nitride, indium antimonide, cadmium selenide, cadmium sulfide, zinc oxide, zinc sulfide, and lead sulfide; and a capping layer comprising the above described compound.

In yet another aspect, the present invention is still further directed to a composition comprising: a nanoparticle comprising a material selected from the group consisting of gold (Au), silver (Ag), platinum (Pt), copper (Cu), nickel (Ni), and alloys thereof; CdSe, CdS, CdSeS, CdTe, InAs, InP, GaAs, PbSe, PbS, HgSe, HgTe, AgInS$_2$, CuInS$_2$, CdSeTe, ZnCdSe, and ZnCdTe; and a capping layer comprising the above described compound.

Other objects and features will be in part apparent and in part pointed out hereinafter.

BRIEF DESCRIPTION OF THE DRAWINGS

(FIG. 4A) LA-PEG-OCH$_3$—AuNPs; (FIG. 4B) LA-(PEG-OCH$_3$)$_2$—AuNPs; (FIG. 4C) bis(LA)-PEG-OCH$_3$—AuNPs. The spectra shown in (FIG. 4A) and (FIG. 4B) were collected at 20 min intervals, while the spectra shown in (FIG. 4C) were collected at 40 min intervals. The progressive digestion of the AuNPs by added NaCN is reflected by the decrease of the SPR peak with time. The absorption feature at 350 nm (FIGS. 4B and 4C) is attributed to the re-formation of lipoic acid after digestion of the AuNP cores.

(FIG. 4A) LA-PEG-OCH$_3$—AuNPs (■); (FIG. 4B) LA-(PEG-OCH$_3$)$_2$—AuNPs (♦); (FIG. 4C) bis(LA)-PEG-OCH$_3$—AuNPs (▲). Data were normalized with respect to the value at t=0. The solid lines are fits to equation 1.

DESCRIPTION OF THE EMBODIMENT(S) OF THE INVENTION

Figure 1A:
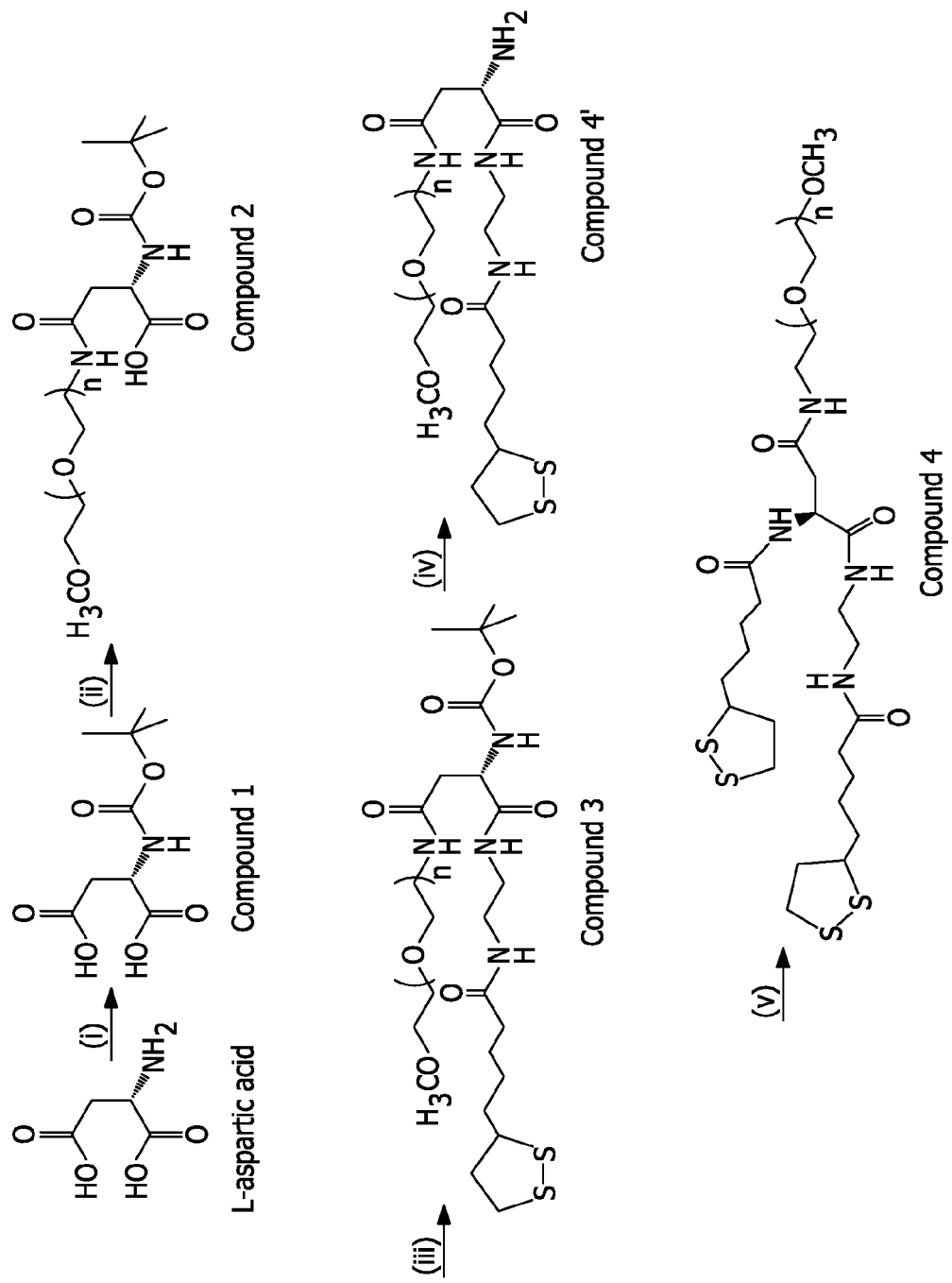
FIG. 1A is a schematic representation of the chemical structures and synthetic steps used to prepare the various ligands including: (Compound 4) bis(LA)-PEG-OCH$_3$ via the synthetic pathway shown through (i) Boc$_2$O (Di-tert-butyl dicarbonate); (ii) NH$_2$-PEG-OCH$_3$, DCC (N,N'-dicyclohexylcarbodiimide); (iii) LA-ethylenediamine, DCC, HOBt.H$_2$O (Hydroxybenzotriazole monohydrate); (vi) 4 M HCl in dioxane; and (v) LA (lipoic acid), DCC, DMAP (4-dimethylaminopyridine).
Figure 1B:
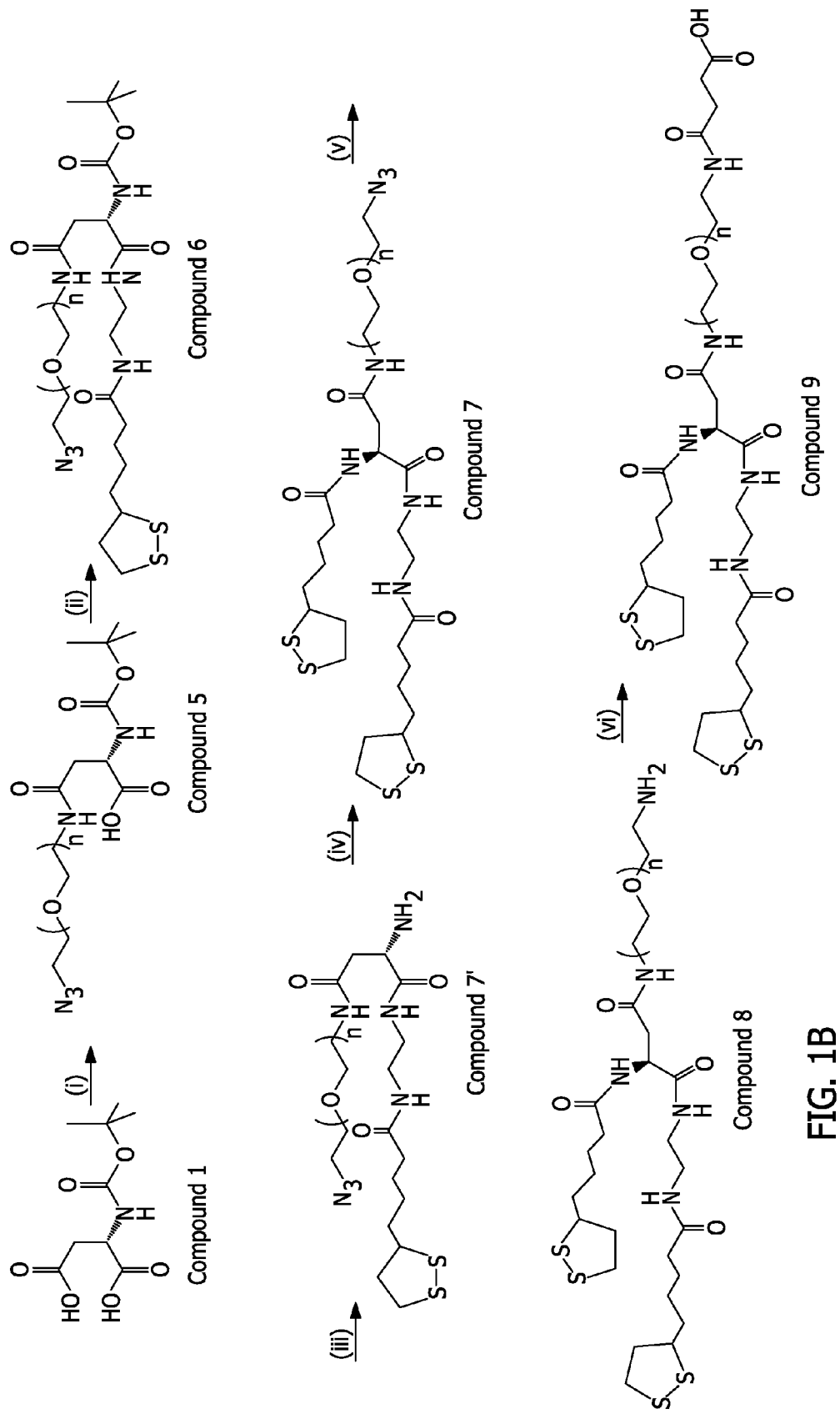
FIG. 1B is a schematic representation of the chemical structures and synthetic steps used to prepare the various ligands including: (Compound 9) bis(LA)-PEG-N$_3$/NH$_2$/COOH via the synthetic pathway shown through (i) NH$_2$-PEG-N$_3$, DCC; (ii) LA-ethylenediamine, DCC, HOBt.H$_2$O; (iii) 4 M HCl in dioxane; (iv) LA (lipoic acid), DCC, DMAP; (v) PPh$_3$ (triphenylphosphine), H$_2$O; and (vi) succinic anhydride, Et$_3$N.

According to some embodiments of the present invention, multi-coordinating ligands that are suitable for capping both QDs and metal nanoparticles, e.g., AuNPs, are provided. The present synthetic scheme starts from L-aspartic acid to develop a versatile platform that allows controllable coupling of one or more lipoic acid (LA) groups, one or more polyethylene glycol (PEG) moieties, along with terminal reactive groups, yielding a series of molecular-scale ligands with various architectures and selective reactivity. In some embodiments of the invention, a series of reactive ligands are prepared, the ligands presenting either one PEG chain appended with two lipoic acid (e.g., bis(LA)-PEG), or two PEG chains attached onto one lipoic acid (e.g., LA-(PEG)$_2$). The chemical structures of ligands and schemes for preparing such ligands according to some embodiments of the invention are shown in FIG. 1A, FIG. 1B, FIG. 1C, and FIG. 1D. This synthetic route provides high reaction yield at each step, and the ligand synthesis can be easily scaled up. In some embodiments, the ligands cap, for example, metal nanoparticles, e.g., AuNPs, and luminescent QDs. Additionally, these ligands are fully compatible with a mild photoligation strategy to promote the in-situ ligand exchange and phase transfer of hydrophobic QDs to buffer media. See References 59, 69, and 70. The nanocrystals ligated with bis(LA)-PEG exhibit remarkable colloidal stability over a broad range of biological conditions. In addition, AuNPs capped with bis(LA)-PEG show greatly improved resistance to sodium cyanide digestion, compared to dithiol-capped nanoparticles. Incorporation of acid or amine groups in the ligand coating permits covalent conjugation of a specific protein or dye-labeled peptide to the QDs using common bioconjugation strategies. In particular, QDs coupled to transferrin facilitate efficient intracellular uptake of QDs, while QD-peptide conjugates has been confirmed by quantifying the Förster Resonance Energy Transfer interactions in the assembled QD-peptide-dye conjugates.

I. Ligand Compounds

In some embodiments, the present invention is directed to a ligand compound that is a derivative of aspartic acid. In some embodiments, the ligand compound has the general structure (I):

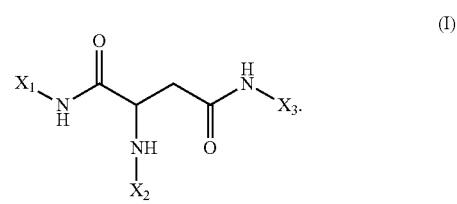

In some embodiments, the present invention is directed to a ligand compound that is a derivative of L-aspartic acid. In some embodiments, the ligand compound has the general structure (I-A):

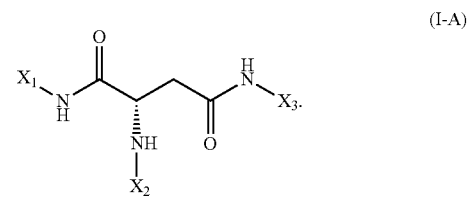

In the context of the above general structures (I) and (I-A), X$_1$, X$_2$, and X$_3$ are each independently selected from the group consisting of hydrogen —H, hydroxyl —OH,

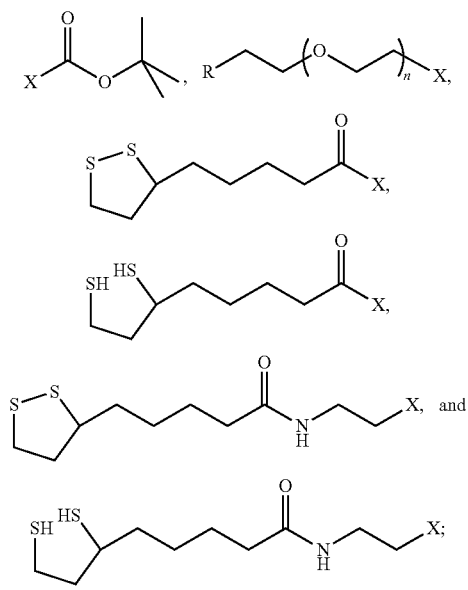

wherein R is selected from the group consisting of hydrogen —H, hydroxyl —OH, methoxy —OCH$_3$, azido —N$_3$, and —NR$_1$R$_2$, wherein R$_1$ and R$_2$ are independently selected from the group consisting of hydrogen —H, 4-oxopentanoic acid

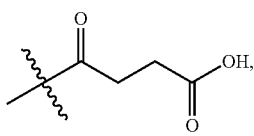 [SMILES: *C(=O)CCC(=O)O]

and 4-acetylbenzaldehyde

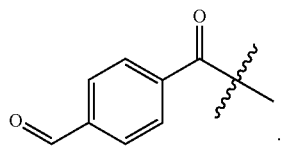 [SMILES: *C(=O)c1ccc(C=O)cc1]

For those moieties comprising repeating groups, each n has a value between 3 and about 20, such as between about 3 and about 10.

In the context of the general structures (I) and (I-A), the "X" denotes the attachment point of the ligand to the $X_1$, $X_2$, and $X_3$ on the derivative of aspartic acid. For example, if a ligand may be depicted as

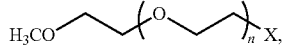

and this ligand is attached at the $X_1$ of the derivative of aspartic acid of Structure (I), this compound has the following structure:

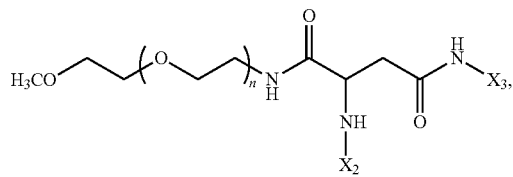

and the $X_2$ and $X_3$ may comprise other moieties as defined herein.

Exemplary ligands of

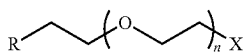

include the following:

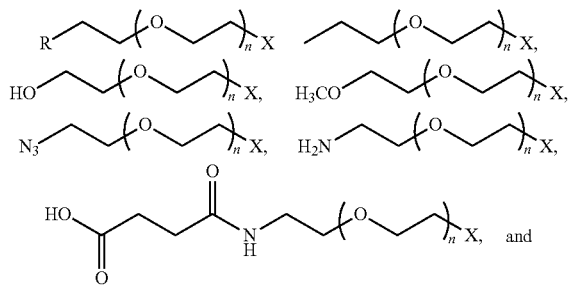

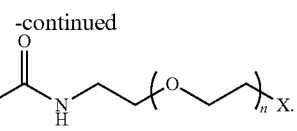

In some embodiments, R is selected from the group consisting of methoxy —$OCH_3$, azido —$N_3$, and —$NR_1R_2$, wherein $R_1$ and $R_2$ are independently selected from the group consisting of hydrogen —H, 4-oxopentanoic acid

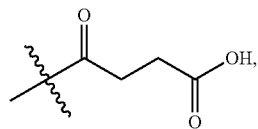 [SMILES: *C(=O)CCC(=O)O]

and 4-acetylbenzaldehyde

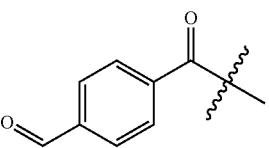

Suitable ligands of

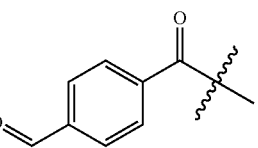

include the following:

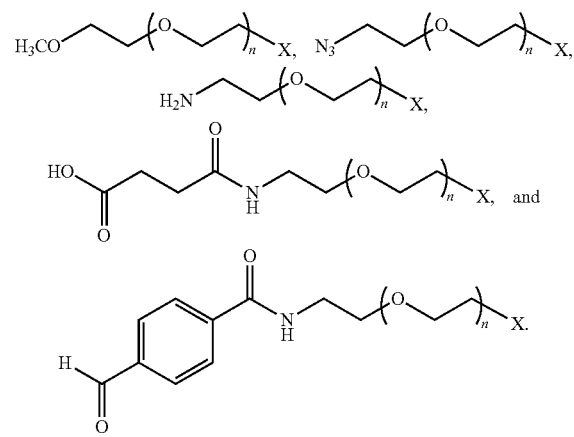

Further in the context of the above structures (I) and (I-A), at least one of $X_1$, $X_2$, and $X_3$ are selected from the group consisting of:

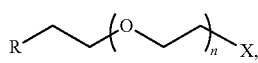

-continued

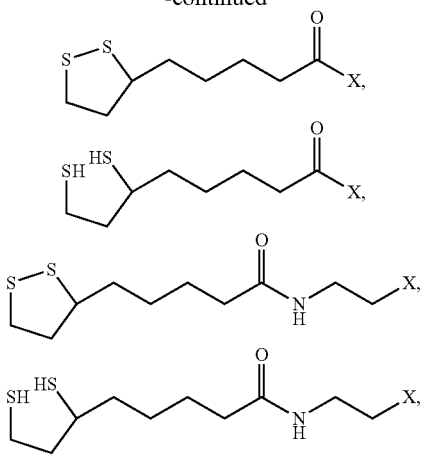

and any combination thereof;
wherein R is selected from the group consisting of hydrogen —H, hydroxyl —OH, methoxy —OCH$_3$, azido —N$_3$, and —NR$_1$R$_2$, wherein R$_1$ and R$_2$ are independently selected from the group consisting of hydrogen —H, 4-oxopentanoic acid

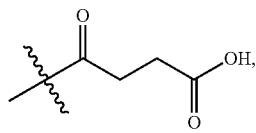 [SMILES: *C(=O)CCC(=O)O]

and 4-acetylbenzaldehyde

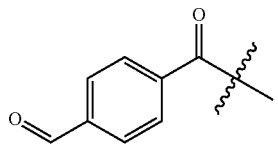

In some embodiments, R is selected from the group consisting of methoxy —OCH$_3$, azido —N$_3$, and —NR$_1$R$_2$, wherein R$_1$ and R$_2$ are independently selected from the group consisting of hydrogen —H, 4-oxopentanoic acid

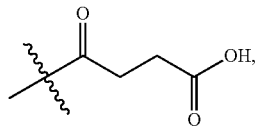 [SMILES: *C(=O)CCC(=O)O]

and 4-acetylbenzaldehyde

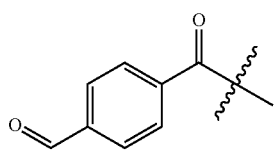

For those moieties comprising repeating groups, each n has a value between 3 and about 20, such as between about 3 and about 10.

In some embodiments, at least two of X$_1$, X$_2$, and X$_3$ in the structures (I) and (I-A) are selected from the group consisting of:

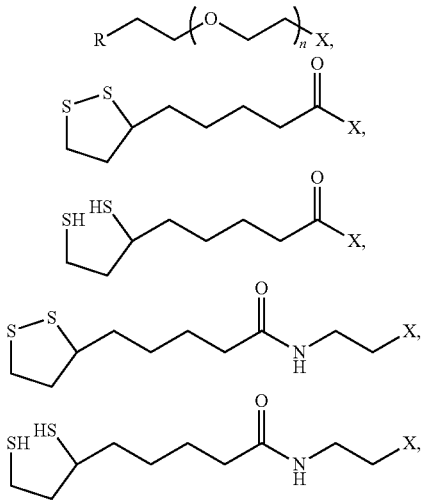

and any combination thereof;
wherein R is selected from the group consisting of hydrogen —H, hydroxyl —OH, methoxy —OCH$_3$, azido —N$_3$, and —NR$_1$R$_2$, wherein R$_1$ and R$_2$ are independently selected from the group consisting of hydrogen —H, 4-oxopentanoic acid

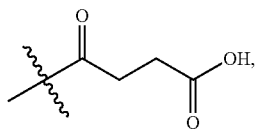 [SMILES: *C(=O)CCC(=O)O]

and 4-acetylbenzaldehyde

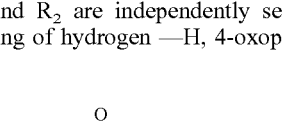

In some embodiments, R is selected from the group consisting of methoxy —OCH$_3$, azido —N$_3$, and —NR$_1$R$_2$, wherein R$_1$ and R$_2$ are independently selected from the group consisting of hydrogen —H, 4-oxopentanoic acid

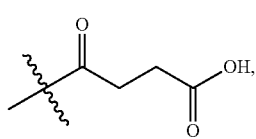 [SMILES: *C(=O)CCC(=O)O]

and 4-acetylbenzaldehyde

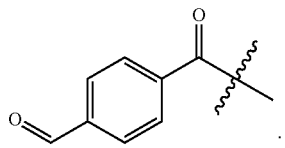

For those moieties comprising repeating groups, each n has a value between 3 and about 20, such as between about 3 and about 10.

In some embodiments, all three of $X_1$, $X_2$, and $X_3$ in the structures (I) and (I-A) are selected from the group consisting of:

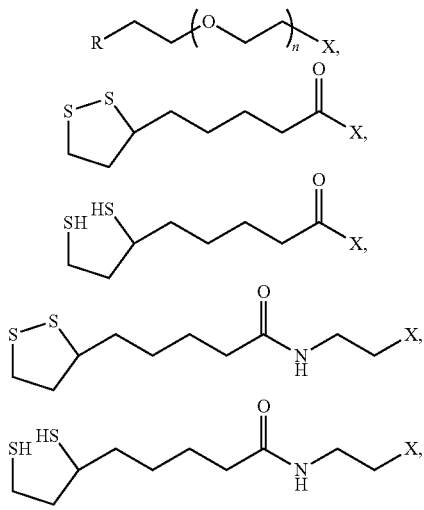

and any combination thereof;
wherein R is selected from the group consisting of hydrogen —H, hydroxyl —OH, methoxy —OCH$_3$, azido —N$_3$, and —NR$_1$R$_2$, wherein R$_1$ and R$_2$ are independently selected from the group consisting of hydrogen —H, 4-oxopentanoic acid

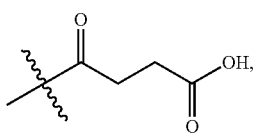 [SMILES: *C(=O)CCC(=O)O]

and 4-acetylbenzaldehyde

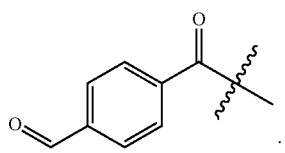

In some embodiments, R is selected from the group consisting of methoxy —OCH$_3$, azido —N$_3$, and —NR$_1$R$_2$, wherein R$_1$ and R$_2$ are independently selected from the group consisting of hydrogen —H, 4-oxopentanoic acid

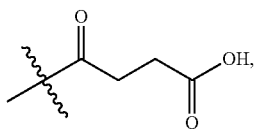 [SMILES: *C(=O)CCC(=O)O]

and 4-acetylbenzaldehyde

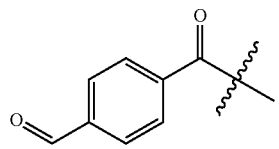

For those moieties comprising repeating groups, each n has a value between 3 and about 20, such as between about 3 and about 10.

In some embodiments, at least one of $X_1$, $X_2$, and $X_3$ is

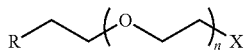

wherein R is selected from the group consisting of hydrogen —H, hydroxyl —OH, methoxy —OCH$_3$, azido —N$_3$, and —NR$_1$R$_2$, wherein R$_1$ and R$_2$ are independently selected from the group consisting of hydrogen —H, 4-oxopentanoic acid

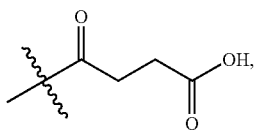 [SMILES: *C(=O)CCC(=O)O]

and 4-acetylbenzaldehyde

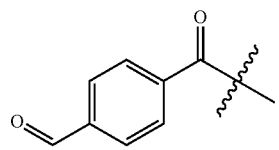

In some embodiments, R is selected from the group consisting of methoxy —OCH$_3$, azido —N$_3$, and —NR$_1$R$_2$, wherein R$_1$ and R$_2$ are independently selected from the group consisting of hydrogen —H, 4-oxopentanoic acid

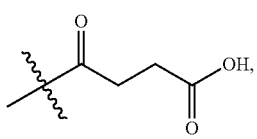

and 4-acetylbenzaldehyde

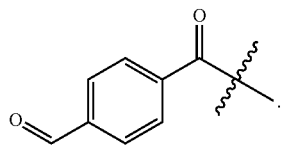 [SMILES: *C(=O)c1ccc(C=O)cc1]

For those moieties comprising repeating groups, each n has a value between 3 and about 20, such as between about 3 and about 10.

In some embodiments, at least one of $X_1$, $X_2$, and $X_3$ is

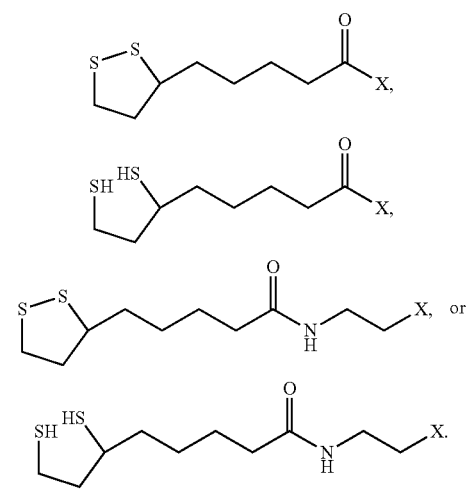

In some embodiments, two of the $X_1$, $X_2$, and $X_3$ are

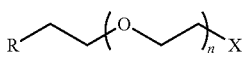

wherein R is selected from the group consisting of methoxy —OCH$_3$, azido —N$_3$, and —NR$_1$R$_2$, wherein R$_1$ and R$_2$ are independently selected from the group consisting of hydrogen —H, 4-oxopentanoic acid

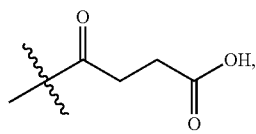 [SMILES: *C(=O)CCC(=O)O]

and 4-acetylbenzaldehyde

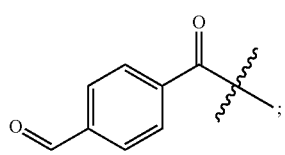 [SMILES: *C(=O)c1ccc(C=O)cc1]

and one of $X_1$, $X_2$, and $X_3$ is

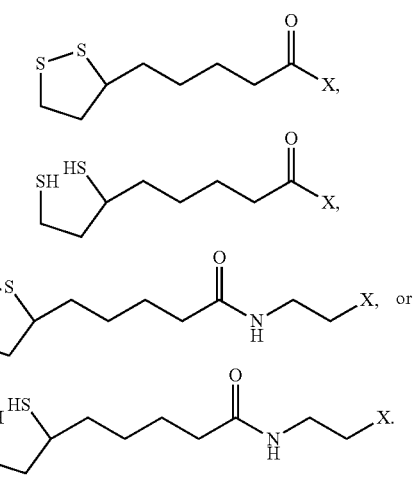

In some embodiments, one of $X_1$, $X_2$, and $X_3$ is

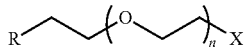

wherein R is selected from the group consisting of methoxy —OCH$_3$, azido —N$_3$, and —NR$_1$R$_2$, wherein R$_1$ and R$_2$ are independently selected from the group consisting of hydrogen —H, 4-oxopentanoic acid

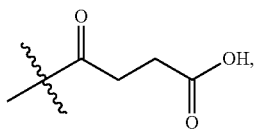 [SMILES: *C(=O)CCC(=O)O]

and 4-acetylbenzaldehyde

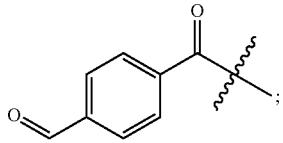 [SMILES: *C(=O)c1ccc(C=O)cc1]

and two of $X_1$, $X_2$, and $X_3$ are selected from among

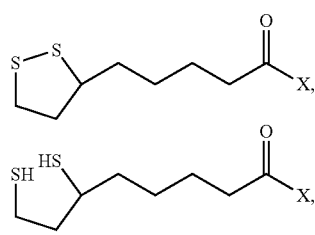

-continued

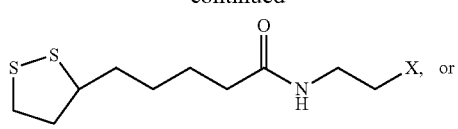

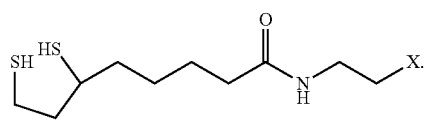

In some embodiments, the derivative of aspartic acid is the following Compound 1:

Compound 1

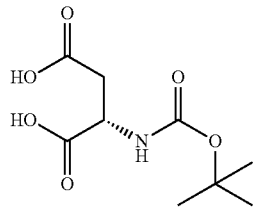

(tert-butoxycarbonyl)-L-aspartic acid.

In some embodiments, the derivative of aspartic acid is the following Compound 2:

Compound 2

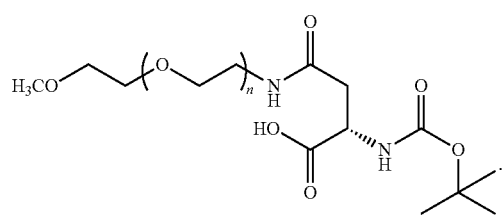

In some embodiments, the derivative of aspartic acid is the following Compound 3:

Compound 3

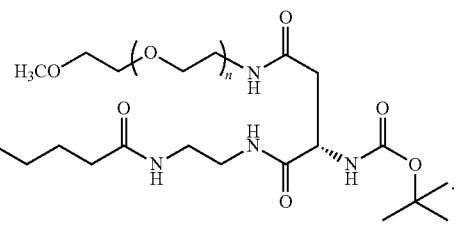

In some embodiments, the derivative of aspartic acid is the following Compound 4:

Compound 4

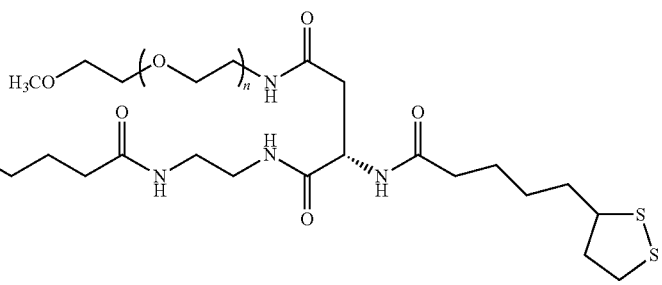

In some embodiments, the derivative of aspartic acid is the following Compound 5:

Compound 5

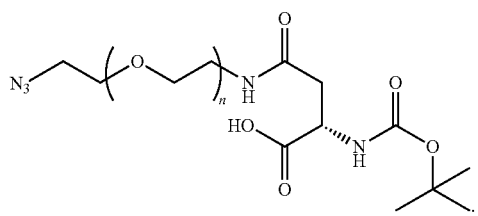

In some embodiments, the derivative of aspartic acid is the following Compound 6:

Compound 6

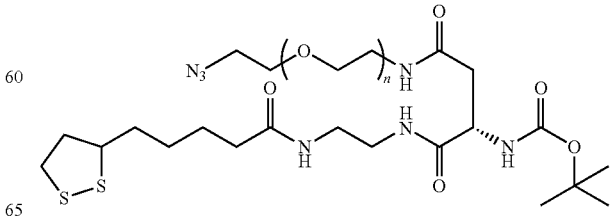

In some embodiments, the derivative of aspartic acid is the following Compound 7:

Compound 7

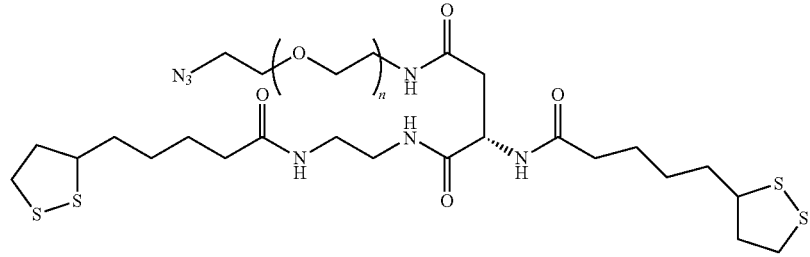

In some embodiments, the derivative of aspartic acid is the following Compound 8:

Compound 8

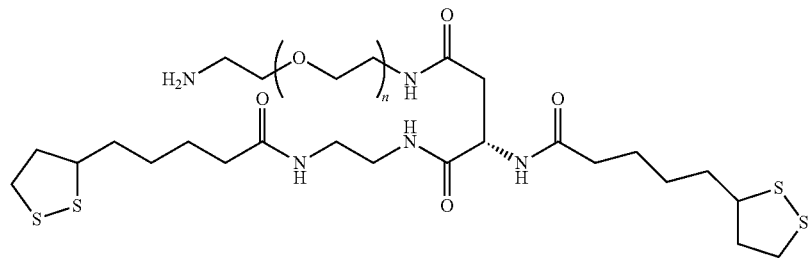

In some embodiments, the derivative of aspartic acid is the following Compound 9:

Compound 9

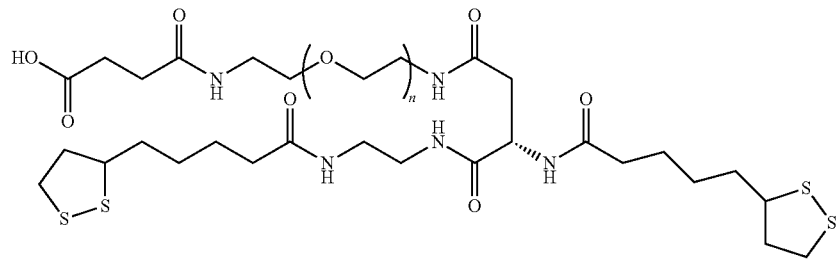

In some embodiments, the derivative of aspartic acid is the following Compound 10:

In some embodiments, the derivative of aspartic acid is the following Compound 11:

Compound 10

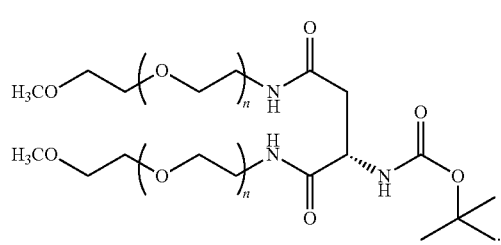

Compound 11

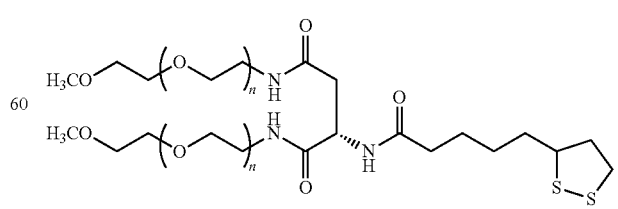

In some embodiments, the derivative of aspartic acid is the following Compound 12:

Compound 12

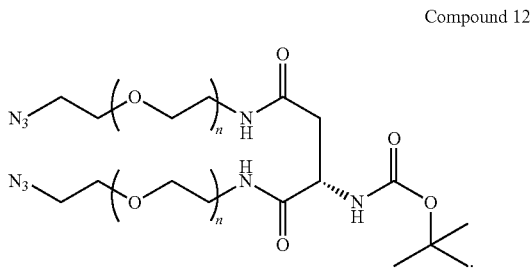

In some embodiments, the derivative of aspartic acid is the following Compound 13:

Compound 13

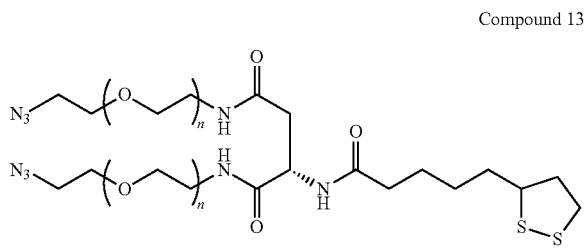

In some embodiments, the derivative of aspartic acid is the following Compound 14:

Compound 14

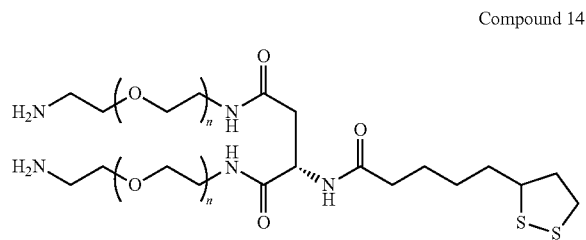

In some embodiments, the derivative of aspartic acid is the following Compound 15:

Compound 15

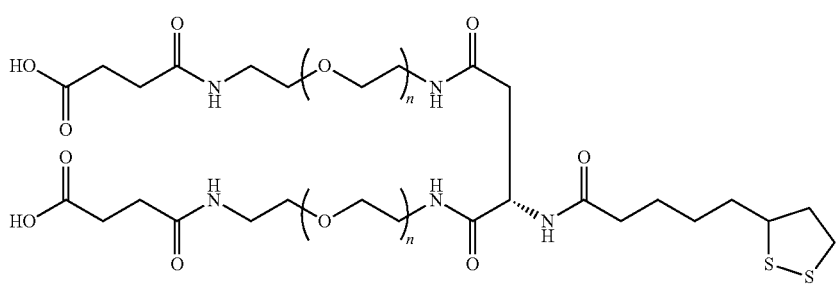

For those Compounds among Compounds 1 through 20 comprising repeating groups, each n has a value between 3 and about 20, such as between about 3 and about 10.

II. Article Comprising a Core Material and a Capping Layer Comprising Ligand Compounds In some embodiments, the present invention is directed to an article comprising a ligand compound as described above and a nanoparticle. The ligand compound forms a capping layer or coating over the nanoparticle core. In some embodiments, the nanoparticle comprises a core material selected from the group consisting of $Fe_3O_4$, $Fe_2O_3$, FePt, Co, Mn-doped $Fe_3O_4$, CdSe/ZnS, InP/ZnS, PbS, CdTe, CoPt, FeCoPt, $CoFe_2O_4$, MnO, $Mn_3O_4$, $Co_3O_4$, FeO, Ni, $TiO_2$, $Al_2O_3$, CdSe, PbSe, $ZrO_2$, ZnO, Au, Ag, and graphene oxide.

In some embodiments, the present invention is directed to an article comprising a ligand compound as described above and a nanoparticle. The ligand compound forms a capping layer or coating over the nanoparticle core. In some embodiments, the nanoparticle comprises a core material selected from the group consisting of silicon, germanium, tin, silicon carbide, selenium, tellurium, boron nitride, boron phosphide, boron arsenide, aluminum nitride, gallium nitride, gallium arsenide, indium nitride, indium antimonide, cadmium selenide, cadmium sulfide, zinc oxide, zinc sulfide, lead sulfide, and the like.

In some embodiments, the present invention is directed to an article comprising a ligand compound as described above and a nanoparticle. The ligand compound forms a capping layer or coating over the nanoparticle core. Exemplary metal elements that may serve as nanoparticle cores include gold (Au), silver (Ag), platinum (Pt), copper (Cu), nickel (Ni), and alloys thereof. Exemplary binary materials include CdSe, CdS, CdSeS, CdTe, InAs, InP, GaAs, PbSe, PbS, HgSe, and HgTe. Exemplary ternary materials include $AgInS_2$, $CuInS_2$, CdSeTe, ZnCdSe, and ZnCdTe.

In general, the nanoparticle core material is generally spherical, oblate spheroid, or prolate spheroid. The nanoparticle may comprise a diameter ranging from about 1 to about 10,000 nanometers, such as between about 1 and about 2500 nanometers, or between about 1 and about 1000 nanometers, or even between about 1 and about 100 nanometers. In some embodiments, core particles may range in diameter from about 2 nanometers to about 500 nanometers, from about 2 nanometers to about 100 nanometers, about 2 nanometers to about 50 nanometers, such as from about 2 nanometers to about 25 nanometers, or from about 5 to about 12 nanometers.

In some embodiments, the core materials may be coated with a shell material. The shell material may comprise a single metallic element or it may contain a binary material comprising a metal. In some embodiments, the shell material may comprise a ternary material, which may comprise two or three metals. The shell material may also be crystalline. The shell material may be monocrystalline or polycrystalline. Exemplary shell materials include ZnS, ZnSe, CdS, ZnSeS, CdS, CdSZn. The thickness of the shell coating may range from about 1 angstrom to about 500 angstroms, such as from about 1 angstrom to about 100 angstroms, such as from about 2 angstrom to about 50 angstroms, such as from about 3 angstroms to about 25 angstroms.

In some embodiments, the nanoparticle may comprise a core material comprising CdS, and the nanoparticle may comprise a shell material comprising ZnS. In these embodiments, one or both of the core material and shell material may be crystalline. In some embodiments, the nanoparticle may comprise a core material comprising CdSe, and the nanoparticle may comprise a shell material comprising ZnS. In these embodiments, one or both of the core material and shell material may be crystalline. In some embodiments, the nanoparticle may comprise a core material comprising CdTe, and the nanoparticle may comprise a shell material comprising ZnS. In these embodiments, one or both of the core material and shell material may be crystalline. In some embodiments, the nanoparticle may comprise a core material comprising CdSe, and the nanoparticle may comprise a shell material comprising CdS. In these embodiments, one or both of the core material and shell material may be crystalline. In some embodiments, the nanoparticle may comprise a core material comprising PbSe, and the nanoparticle may comprise a shell material comprising ZnS. In these embodiments, one or both of the core material and shell material may be crystalline. In some embodiments, the nanoparticle may comprise a core material comprising PbSe, and the nanoparticle may comprise a shell material comprising CdSe. In these embodiments, one or both of the core material and shell material may be crystalline. In some embodiments, the nanoparticle may comprise a core material comprising AgInS, and the nanoparticle may comprise a shell material comprising ZnS. In these embodiments, one or both of the core material and shell material may be crystalline.

III. Ligand Design.

Figure 1C:
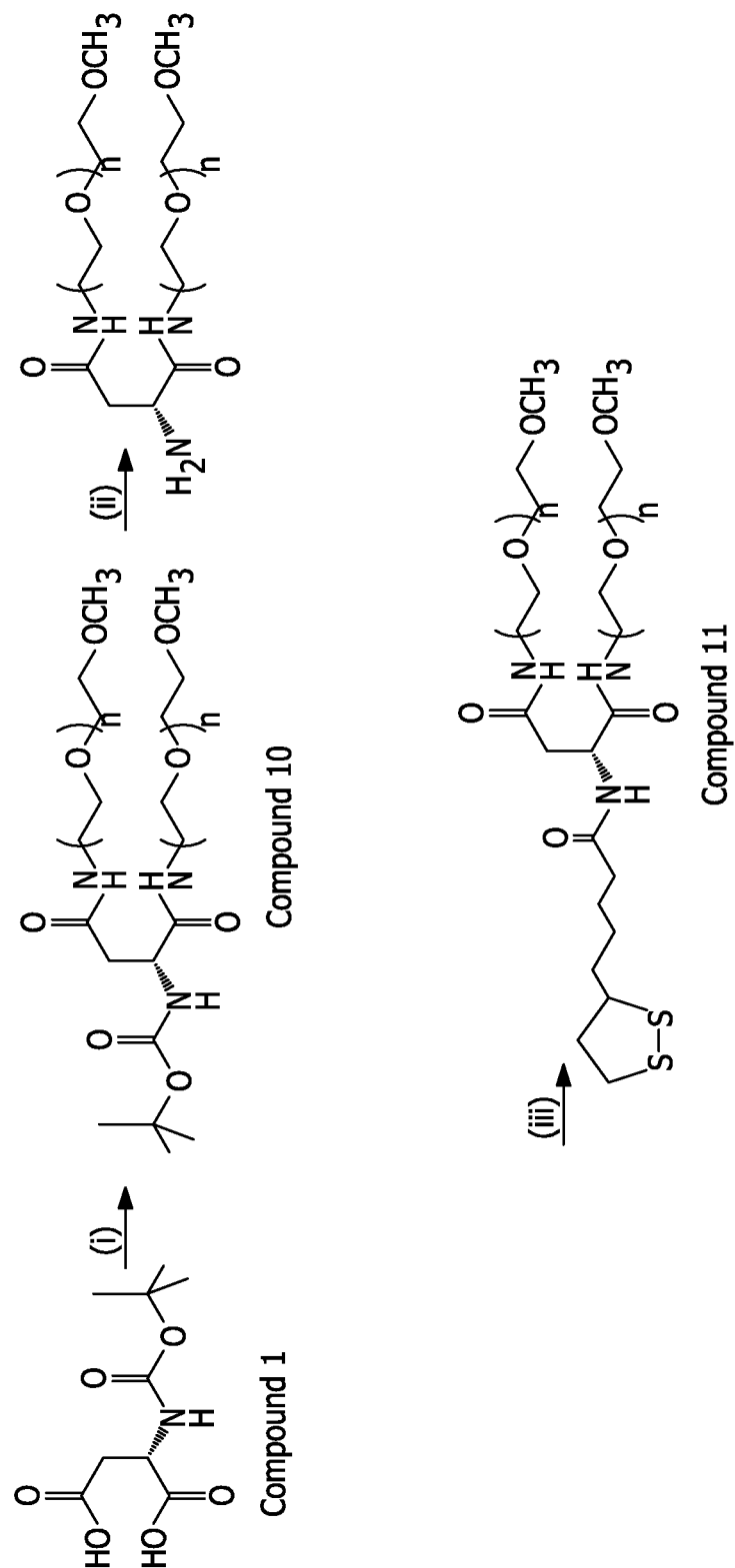
FIG. 1C is a schematic representation of the chemical structures and synthetic steps used to prepare the various ligands including: (Compound 11) LA-(PEG-OCH$_3$)$_2$ via the synthetic pathway shown through (i) NH$_2$-PEG-OCH$_3$, DCC, HOBt.H$_2$O; (ii) 4 M HCl in dioxane; and (iii) LA (lipoic acid), DCC, HOBt.H$_2$O.
Figure 1D:
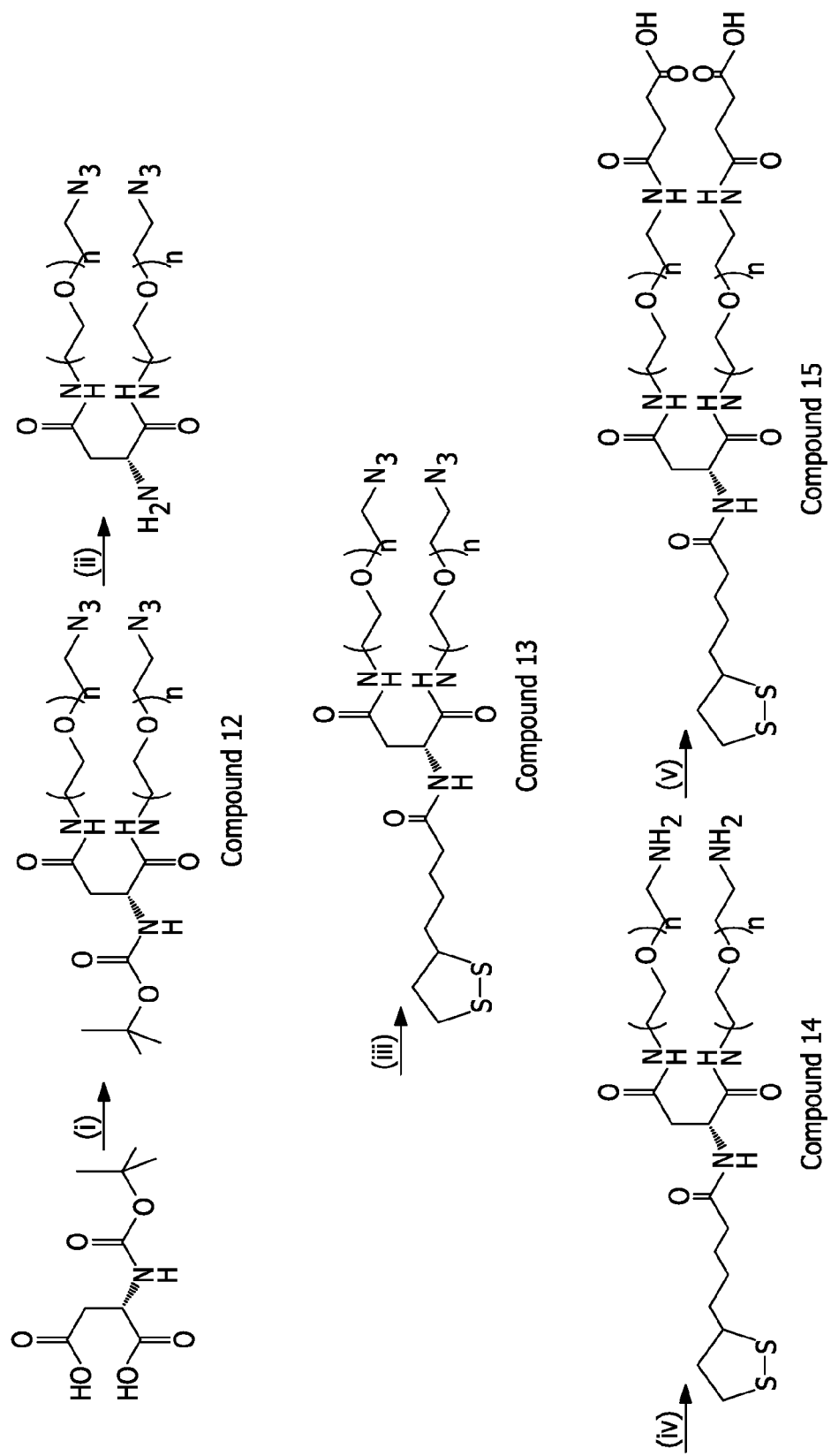
FIG. 1D is a schematic representation of the chemical structures and synthetic steps used to prepare the various ligands including: (Compound 15) LA-(PEG-N$_3$/NH$_2$/COOH)$_2$ via the synthetic pathway shown through (i) NH$_2$-PEG-N$_3$, DCC, HOBt.H$_2$O; (ii) 4 M HCl in dioxane; (iii) LA (lipoic acid), DCC, HOBt.H$_2$O; (iv) PPh$_3$, H$_2$O; and (v) succinic anhydride, Et$_3$N.

One key feature of the ligand compounds according to some embodiments of the present invention is the use of a single precursor, the amino acid aspartic acid or L-aspartic acid, to prepare the various ligands. The ability to selectively activate one or two groups in the aspartic acid allows one to build up the desired ligand structure, while controlling the nature and number of coordinating groups as well as the number of hydrophilic PEG moieties introduced in the same ligand. Additionally, the various synthetic steps rely mainly on conventional peptide coupling chemistry (e.g., BOC protection and deprotection under acidic conditions along with carbodiimide chemistry). Our design allows the introduction of several reactive groups (e.g., —$N_3$, —$NH_2$, —COOH) in the ligands and provides high reaction yield at each step. Several ligand architectures, including bis(LA)-PEG (higher coordination ligands) and LA-$(PEG)_2$ (ligands with higher PEG branching) have been prepared using the same chemical route. See FIGS. 1A, 1B, 1C, and 1D. The present route for preparing bis(LA)-appended ligands is simpler than the Michael addition reaction we have previously employed and is more effective for introducing terminal reactive groups in the ligands. See Reference 64. Furthermore, comparison between of coating of the NPs with either bis(LA)-PEG or LA-$(PEG)_2$ allow exploration of the effects of coordination vs steric hindrance on the surface ligand density. For LA-$(PEG)_2$, one can combine terminally-inert PEG and PEG-appended with a reactive group within the same ligand by coupling the $NH_2$-PEG-$OCH_3$ and $NH_2$-PEG-$N_3$ sequentially onto the Boc-aspartic acid. A few additional precautions have to be applied, nonetheless. The use of Boc-anhydride protection eliminates issues of cross coupling, while selective mono coupling is achieved by controlling the molar ratio of DCC (coupling reagent) and Boc-aspartic (e.g., a molar ratio of 1.1:1 was used in the scheme shown in FIG. 1A, step ii). Use of LA-ethylenediamine permitted the introduction of LA group via DCC coupling onto COOH groups in the aspartic acid. See FIG. 1A, step iii). To functionalize the bis(LA)-PEG ligands, $NH_2$-$PEG_{1000}$-$N_3$ was substituted for $NH_2$-$PEG_{750}$-$OCH_3$; transformation of the azide to amine and acid followed conventional chemical modifications. See Reference 54. The synthesis of LA-$(PEG)_2$ ligands was slightly simpler, as coupling of two PEG moieties (either identical or complementary) could be carried in the same step as shown in FIG. 1C and FIG. 1D. Finally, the chiral nature of the L-aspartic acid, with its off plane arrangements of the three reactive arms, yields ligands where the anchoring groups and the hydrophilic/reactive functionalities do not lay in the same plane. This offers reduced steric hindrance and may improve the ligand packing on the NP surfaces.

Some intermediate compounds (precursors), such as compound 4' and compound 7' can be used as capping ligands for QDs or AuNPs. Indeed these two compounds provide two commonly used reactive groups, amine and azide, that can be further modified. For example, compound 4' can potentially allow the attachment of target small molecules (redox complexes) very close to the NP surface. Similarly, compound 7' combines both azide and amine on the same ligand, which can permit dual targeting of the NPs with different biomolecules, or transformation of the amine to acid to yield azide/acid functionalized NPs.

IV. Ligand Exchange and Optical Characterization of the Nanocrystals.

The prepared ligands are compatible with photoligation as means of promoting in-situ cap exchange and phase transfer of TOP/TOPO-QDs to polar and buffer media. See Reference 69. This strategy exploits the photochemical transformation of lipoic acid in the presence of UV irradiation (~330-360 nm) and starts with the oxidized form of the ligands during the ligand exchange step, eliminating the need for chemical reduction of the LA groups prior to phase transfer. Furthermore, this scheme is mild towards sensitive groups such as azide and aldehyde, two functions that are highly desirable in bio-orthogonal chemistry. It is also compatible with other LA-based hydrophilic ligands such as LA-zwitterion. See References 65 and 69.

Figure 2A:
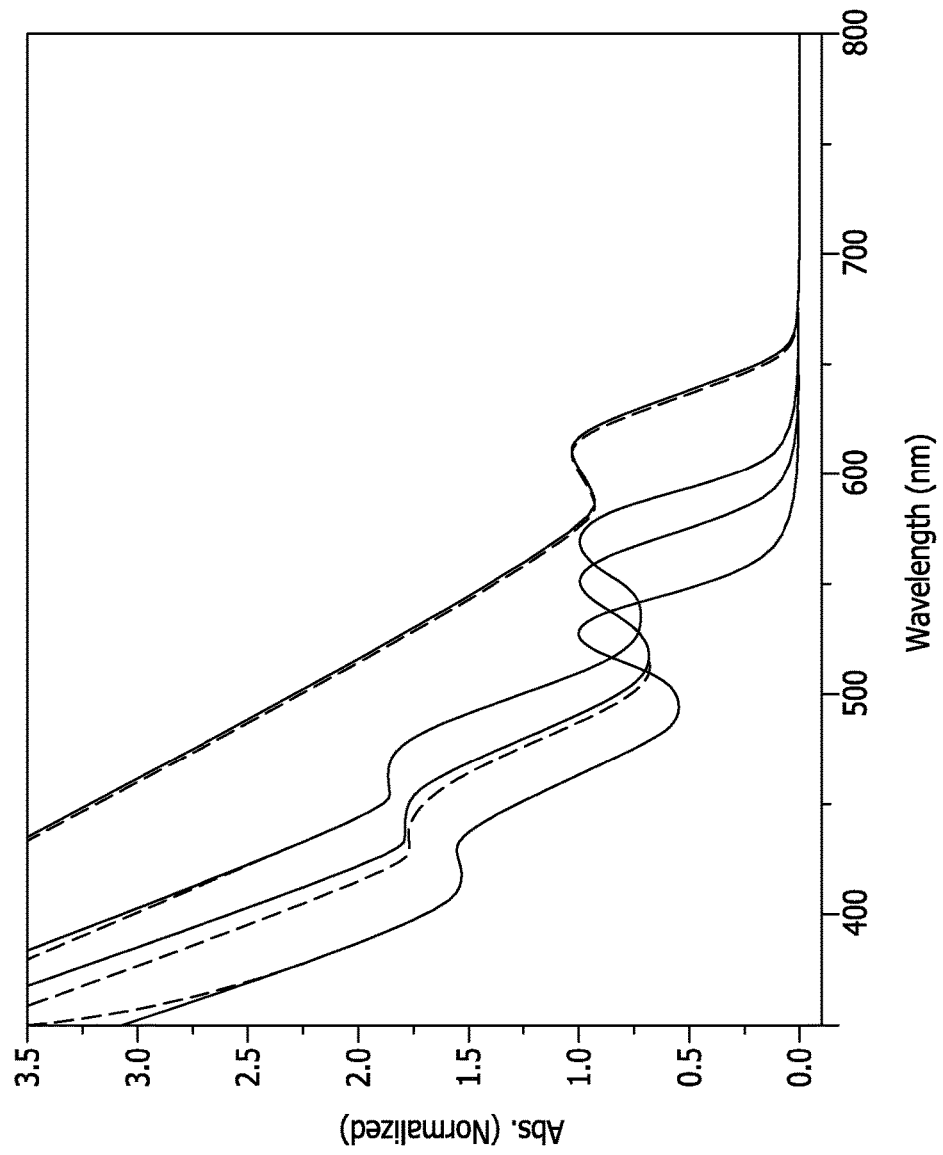
FIGS. 2A and 2B are UV-vis (FIG. 2A) and PL spectra (FIG. 2B) of the various sets of QDs ($\lambda_{em}$=540 nm, 567 nm, 590 nm, 598 nm); dotted lines are spectra collected from the native hydrophobic QDs in organic solvent and the solid lines designate spectra collected from hydrophilic QDs photoligated with bis(LA)-PEG-OCH$_3$. The absorption and PL spectra were normalized with respect to the band edge peak and the emission maximum respectively.
Figure 2B:
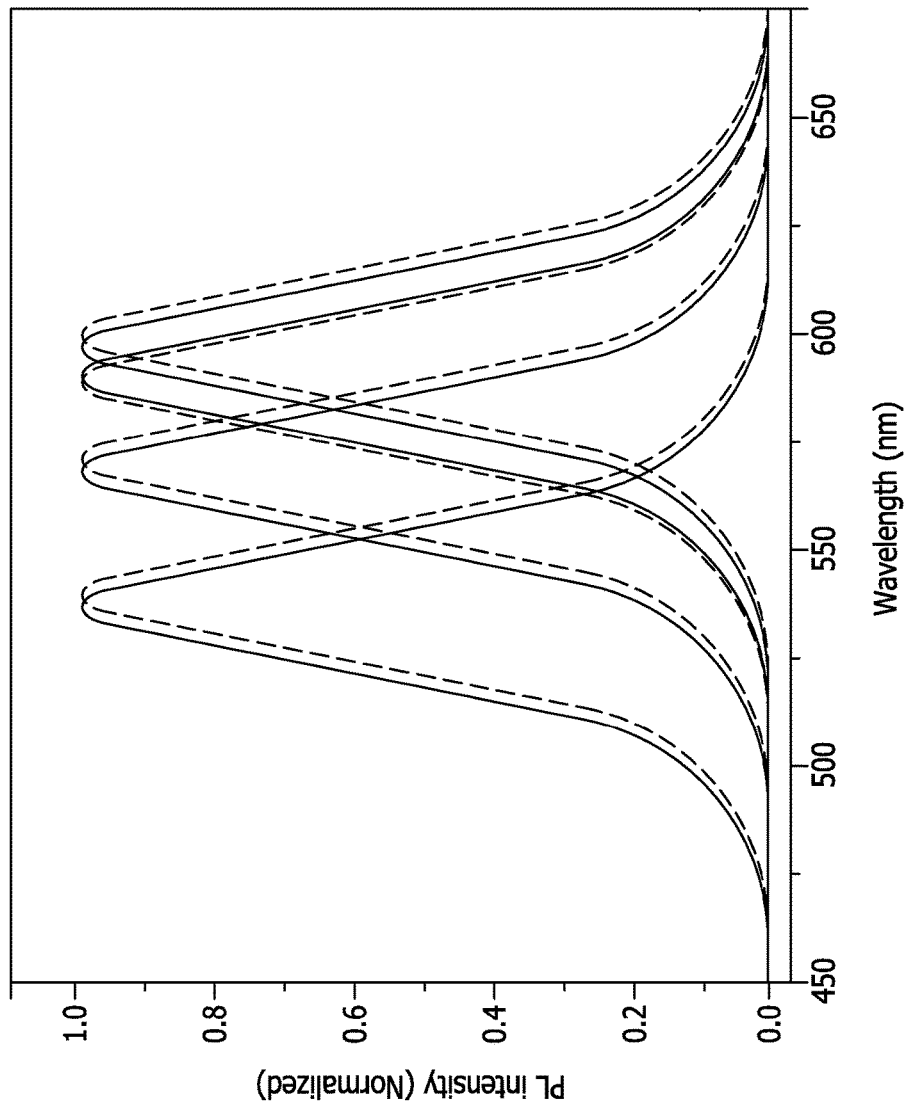
Figure 2C:
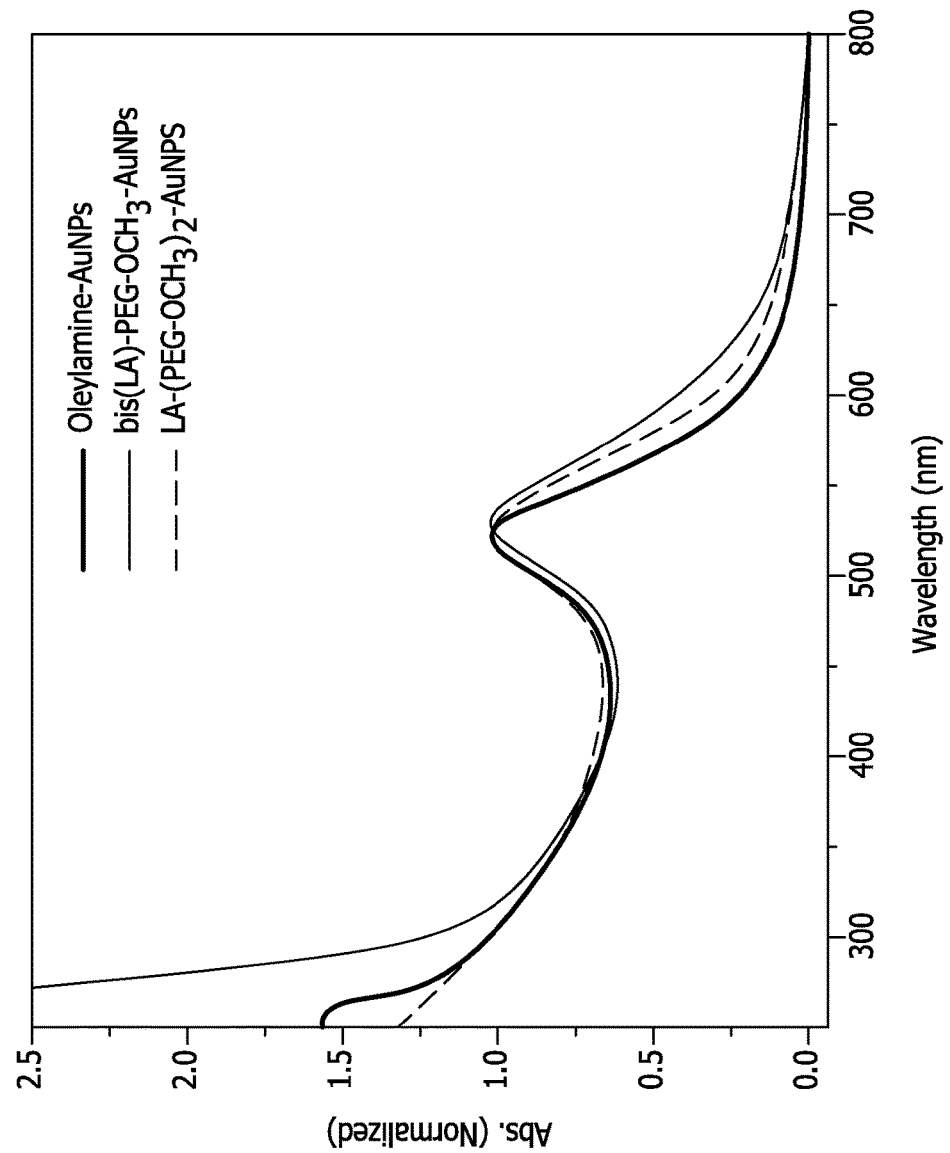
FIG. 2C is UV-vis absorption spectra of 10 nm (hydrodynamic radius) AuNPs dispersed in hydrophobic phase (thick line ——), ligand exchanged with bis(LA)-PEG-OCH$_3$ (thin line z,900) and LA-(PEG-OCH$_3$)$_2$ (dashed line - - - -). The strong absorbance below 350 nm measured for bis(LA)-PEG-OCH$_3$—AuNPs is due to a stronger contribution from the ligand. The spectra were normalized with respect to the surface plasmon resonance peak at 520 nm.

The photoligation was applied to cap exchange a few different size QDs with the new ligands. The absorption (FIG. 2A) and PL spectra (FIG. 2B) collected from the four sets of QDs ($\lambda_{em}$=540 nm, 567 nm, 590 nm, 598 nm) before and after phase transfer to DI water were essentially identical, indicating that the photoligation strategy did not alter the photophysical properties of the nanocrystals. Similar observations were collected for QDs photoligated with LA-(PEG-$OCH_3$)$_2$ ligands. Phase transfer of AuNPs was more straightforward as it did not require chemical reduction or photo-irradiation of the ligand prior to coating of the NPs. The oxidized ligands (i.e., bis(LA)-PEG and LA-$(PEG)_2$) were used; reduction of the dithiolanes upon coordination onto the Au surfaces is expected to take place. See Reference 71. FIG. 2C shows that the SPR peak in the absorption spectra collected from dispersions of AuNPs before and after phase transfer are essentially identical, indicating no change in the size or integrity of the nanoparticles after ligand exchange.

V. Colloidal Stability Tests Applied to QDs and AuNPs.

Figure 3:
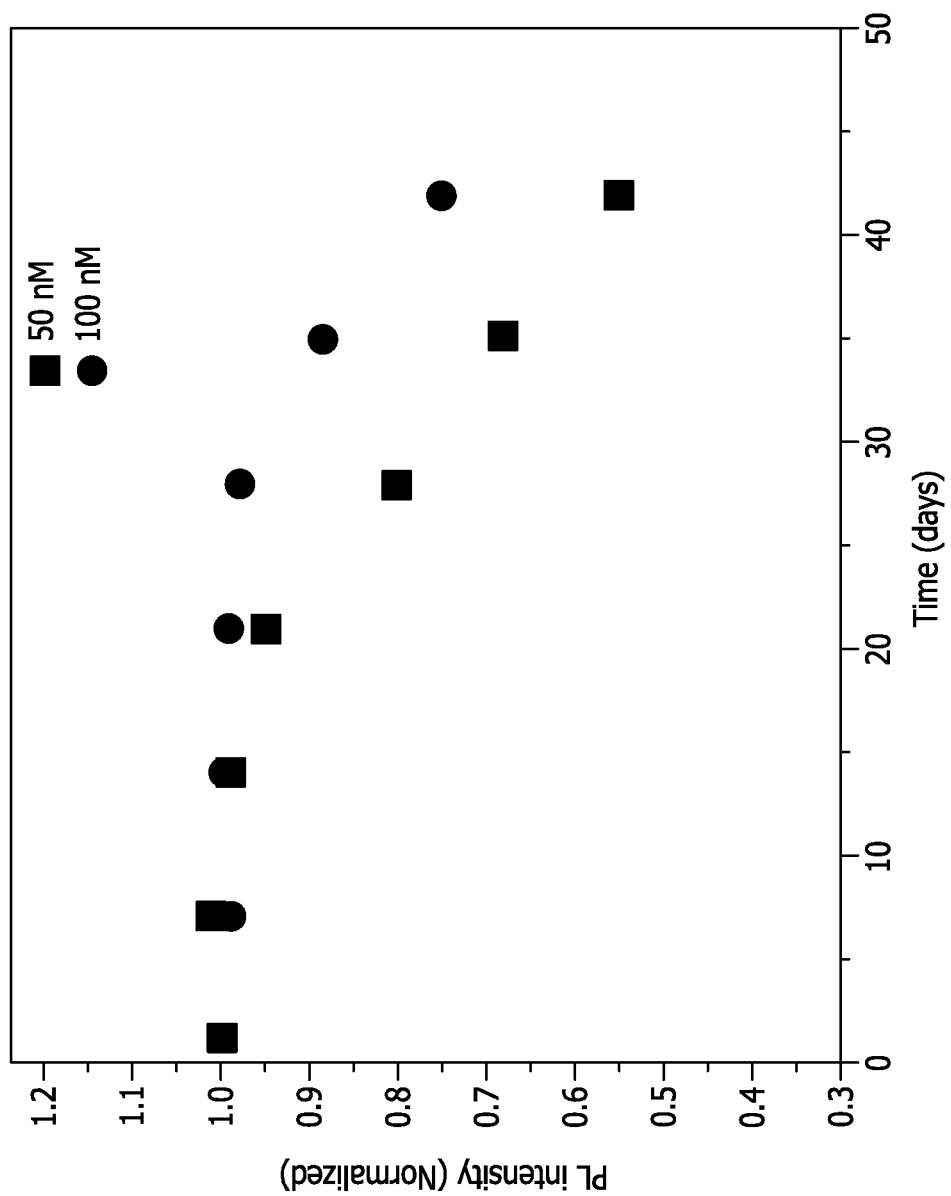
FIG. 3 is a Plot of PL intensity versus storage time of QDs ($\lambda_{em}$=540 nm) photoligated with bis(LA)-PEG-OCH$_3$ at different concentrations of 50 nM (■) and 100 nM (●). The samples were stored at ambient conditions with exposure to room light.

Colloidal stability of both types of materials phase transferred using bis(LA)-PEG were tested as these ligands are expected to provide stronger binding onto the metal-rich surfaces of the nanocrystals. Tests carried out using LA- (PEG)$_2$ were used as reference. Colloidal stability tests of QDs photoligated with bis(LA)-PEG-OCH$_3$ were carried out in the presence of added excess NaCl, cell growth media, acidic and basic pHs; additionally, the long term stability of dispersions were probed at very low concentrations stored at room temperature and under light exposure. Colloidal stability is most critical for applications in biology where media rich in reducing agents and salts are used, and rather low nanocrystal concentrations are needed for imaging and sensing. See Reference 64. QDs photoligated with bis(LA)-PEG-OCH$_3$ stayed homogeneously dispersed with no sign of aggregation over the pH range 3-14 for at least 6 months of storage at 4° C. (duration of the test). These dispersions also remained stable in the presence of 1M, 2M NaCl and when dispersed in 50%, 100% cell growth media. Stability tests of these bis(LA)-PEG-OCH$_3$-QD dispersions at nanomolar concentration were carried by visual examination combined with tracking of the PL emission with storage time. The progression of the fluorescence intensity collected from 50 nM and 100 nM QD dispersions was tracked over a four-week period. See FIG. 3. Both dispersions stayed homogeneous, though the PL signal progressively decayed; emission persisted at 50% of its initial value, nonetheless. This is promising compared to data collected for dispersions of QDs capped with monothiol-PEG and even DHLA-PEG ligands, where PL is strongly reduced under similar storage conditions. See References 45 and 70.

Figure 4A:
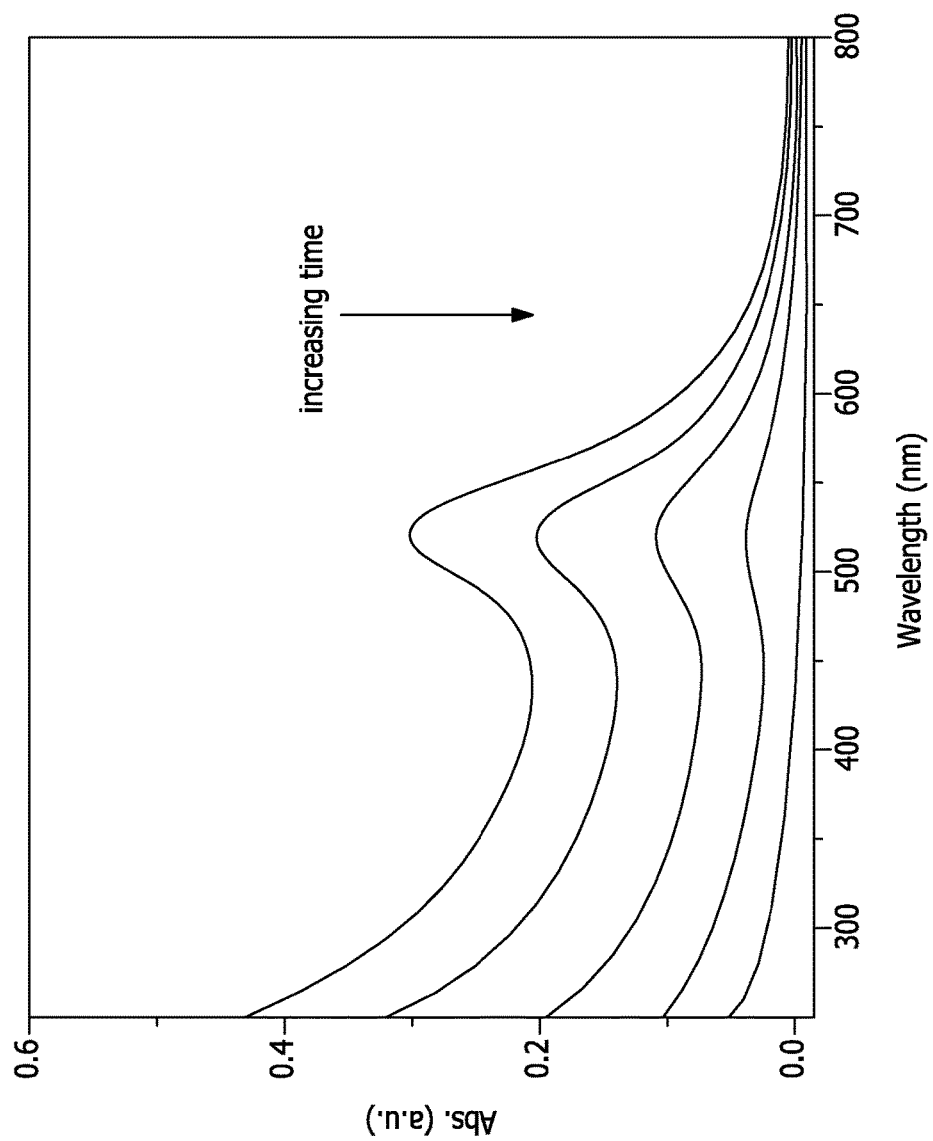
FIGS. 4A, 4B, and 4C depict Time-progression of the UV-vis absorption spectra of dispersions of AuNPs (6.3 nM) collected in the presence of NaCN (62 mM)
Figure 4B:
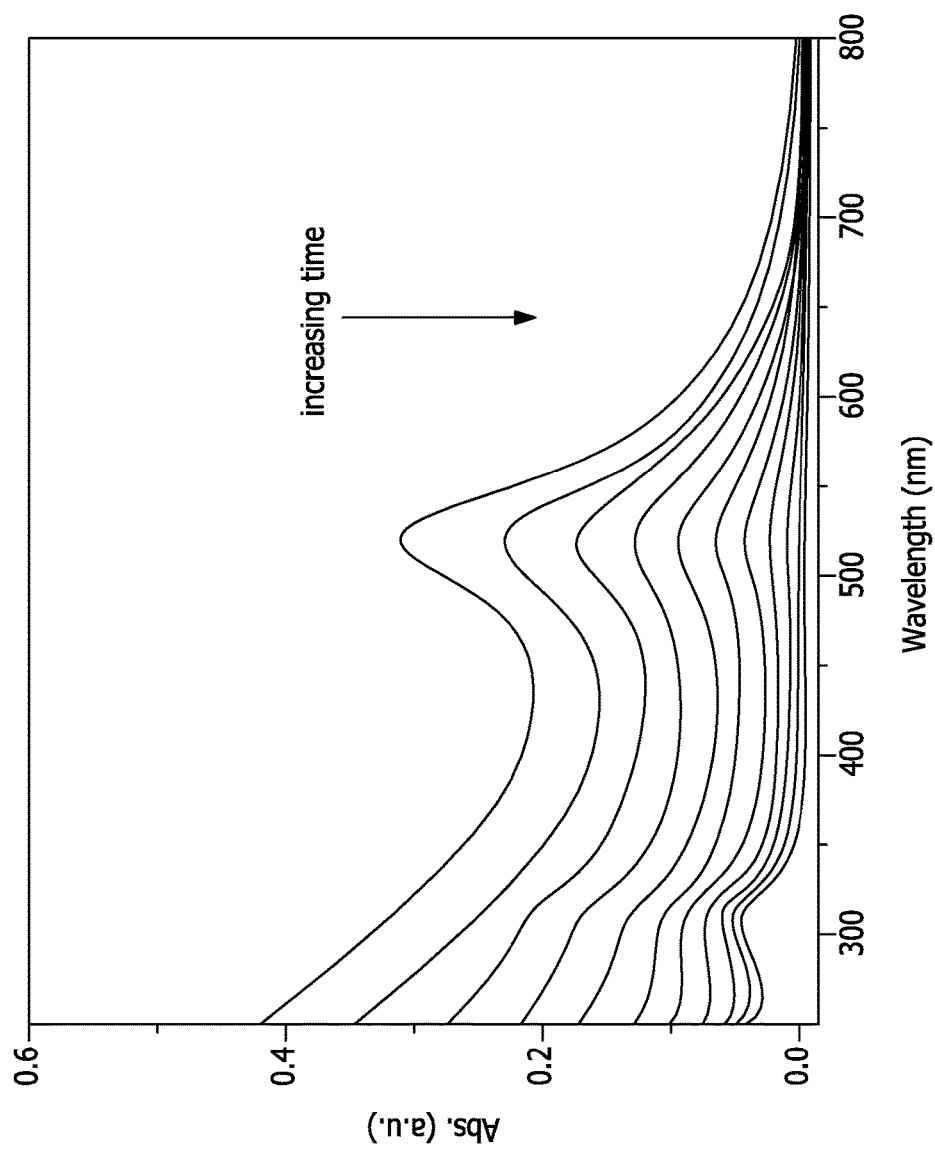
Figure 4C:
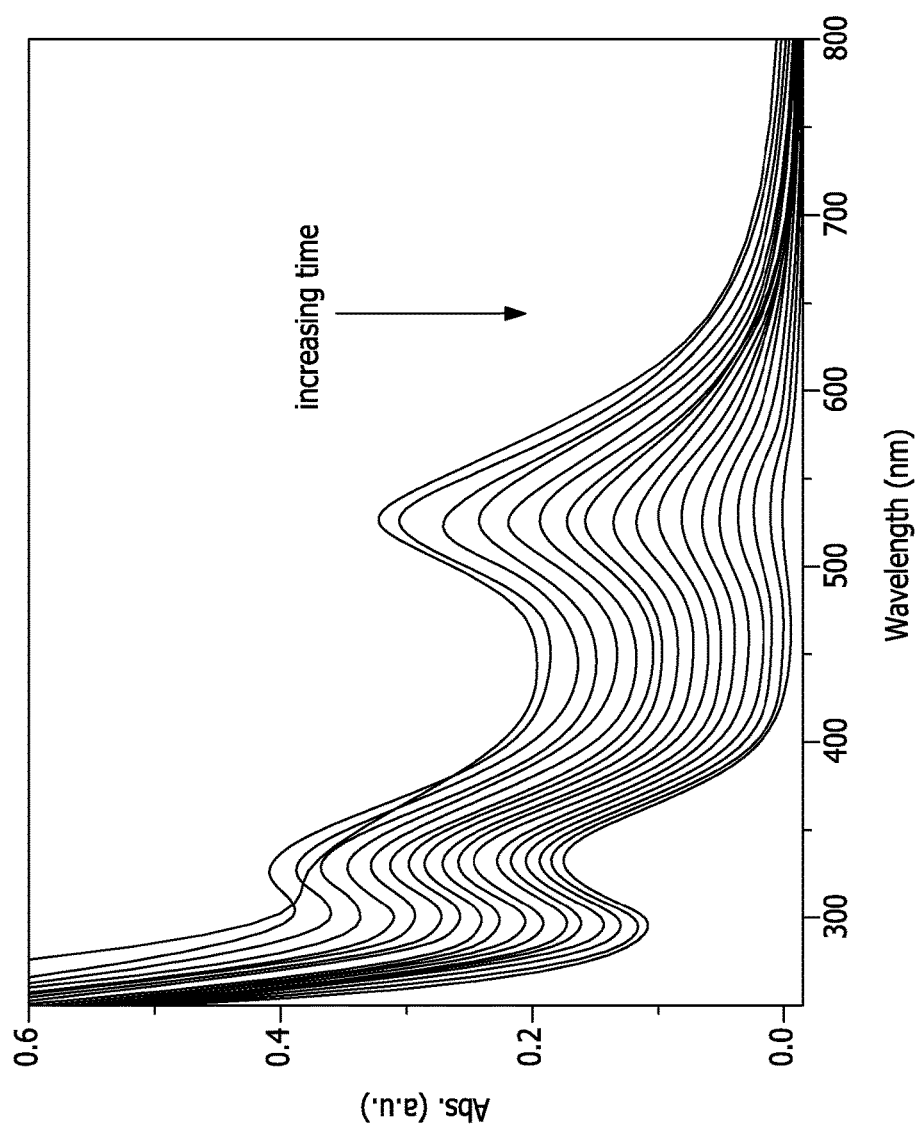
Figure 4D:
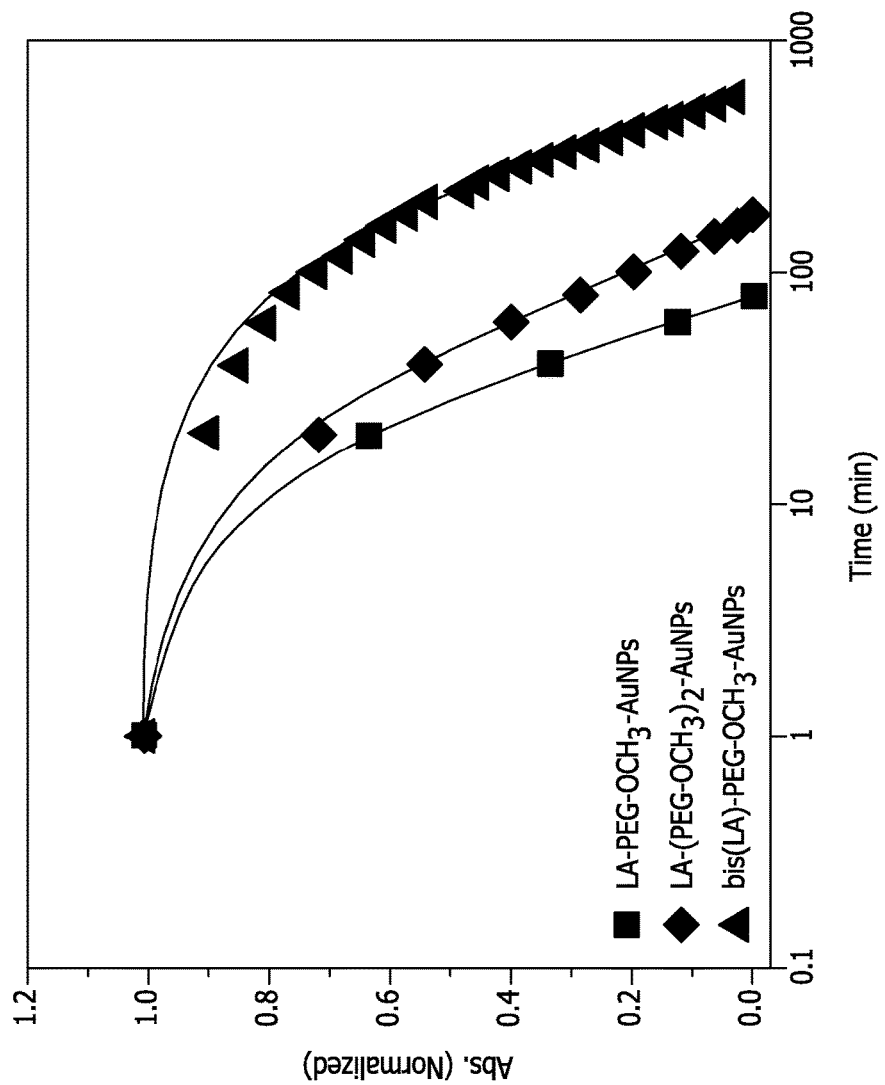
FIG. 4D is a semi-logarithmic plot of time-progression of the SPR measured for AuNPs capped with the three sets of ligands extracted from the data shown in (FIGS. 4A, 4B, and 4C.

Similarly, bis(LA)-PEG-OCH$_3$ was found to provide AuNPs with excellent long-term colloidal stability over the pH range 2 to 14, in the presence of excess NaCl and in cell growth media for over 1 year of storage under ambient conditions. Additional tests compared the stability of AuNPs ligated with either LA-(PEG)$_2$ or bis(LA)-PEG ligands (lower coordination and larger spatial extension and vice versa) against NaCN digestion. Cyanide anions (CN$^{-1}$) are highly reactive towards metal surfaces and can digest AuNP cores, forming Au(CN)$_2^-$ complexes in the medium. See References 68 and 72. This results in progressive loss of the plasmonic absorption feature. This test was applied to AuNPs ($R_H$=10 nm) ligated with LA-PEG-OCH$_3$, LA-(PEG-OCH$_3$)$_2$ and bis(LA)-PEG-OCH$_3$, and provided a side-by-side comparison of the effects of coordination, ligand size and spatial extension of the PEG moieties on the NPs stability to NaCN digestion. Aliquots of 6.2 M NaCN solution (5 μL) were added to dispersions of all three ligated-AuNPs (using final AuNP and NaCN concentrations of 6.3 nM and 62 mM, respectively) and the absorption spectra were collected every 20 min for periods ranging from 1.5 to 10 hours. FIG. 4A shows that the absorption rapidly decreased for LA-PEG-OCH$_3$—AuNPs to nearly baseline values after 1.5 hours; the dispersion progressed from pinkish-red to completely colorless, indicating the near complete digestion of the AuNP cores. In comparison, a slightly slower loss in the plasmonic absorption (corresponding to a slower digestion) was measured for LA-(PEG-OCH$_3$)$_2$—AuNPs, where background level was reached after 3.5 hours. FIG. 4B. The strongest resistance was measured for dispersions of bis(LA)-PEG-OCH$_3$—AuNPs, where nearly complete digestion of the AuNPs was reached after 10 hours. See FIG. 4C. We further assessed the rate of decomposition by measuring the time-dependent decrease of the surface plasmon peak at 520 nm and fitting it to a first order exponential decay function of the form:

$$y = y_0 \times e^{-\frac{t}{t_D}}, \quad (1)$$

Where $t_D$ designates the decay time and $y_0$ is the absorbance value at t=0, as shown in FIG. 4D. The decay time ($t_D$) extracted from fits to the data collected from the various AuNP samples are: 56 min for LA-PEG-OCH$_3$—AuNPs, 75 min for LA-(PEG-OCH$_3$)$_2$—AuNPs and 526 min for bis(LA)-PEG-OCH$_3$—AuNPs. We found that $t_D$ (bis(LA)-PEG-OCH$_3$) is ~one order of magnitude longer than $t_D$ (LA-PEG-OCH$_3$). Data show that the bis(LA) ligands provided substantially better protection for the AuNPs core against cyanide digestion.

VI. Colloidal Stability Against Ligand Desorption.

Figure 5A:
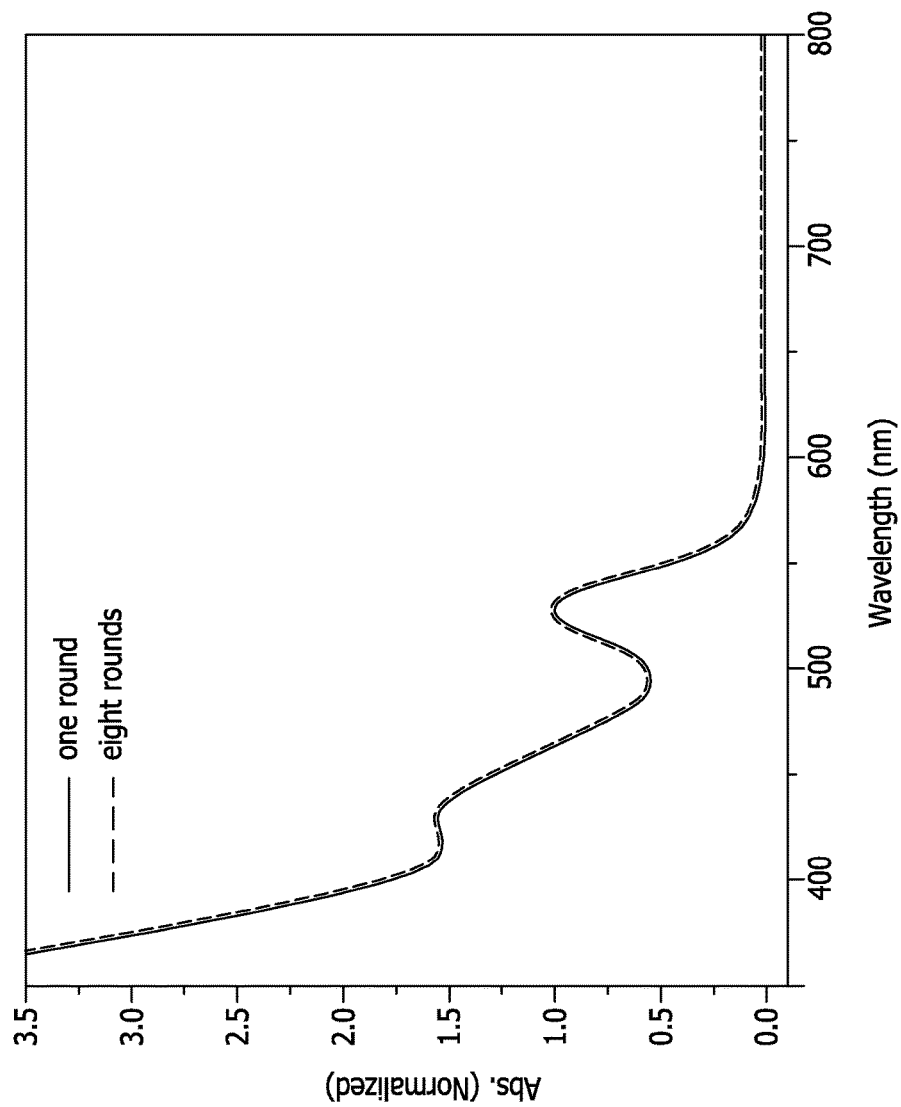
FIG. 5A is a UV-vis absorption spectrum and FIG. 5B is a PL spectrum of dispersions of bis(LA)-PEG-OCH$_3$-QDs ($\lambda_{em}$=540 nm) after one (thin line z,900) and eight rounds (dashed line - - - -) of purification using a centrifugal membrane device as described in the text. The absorption and PL spectra were normalized with respect to the band edge peak and the emission maximum, respectively. The insets show the white light and fluorescence images of the bis(LA)-PEG-OCH$_3$-QDs after eight rounds of purification then dispersed in DI water.
Figure 5B:
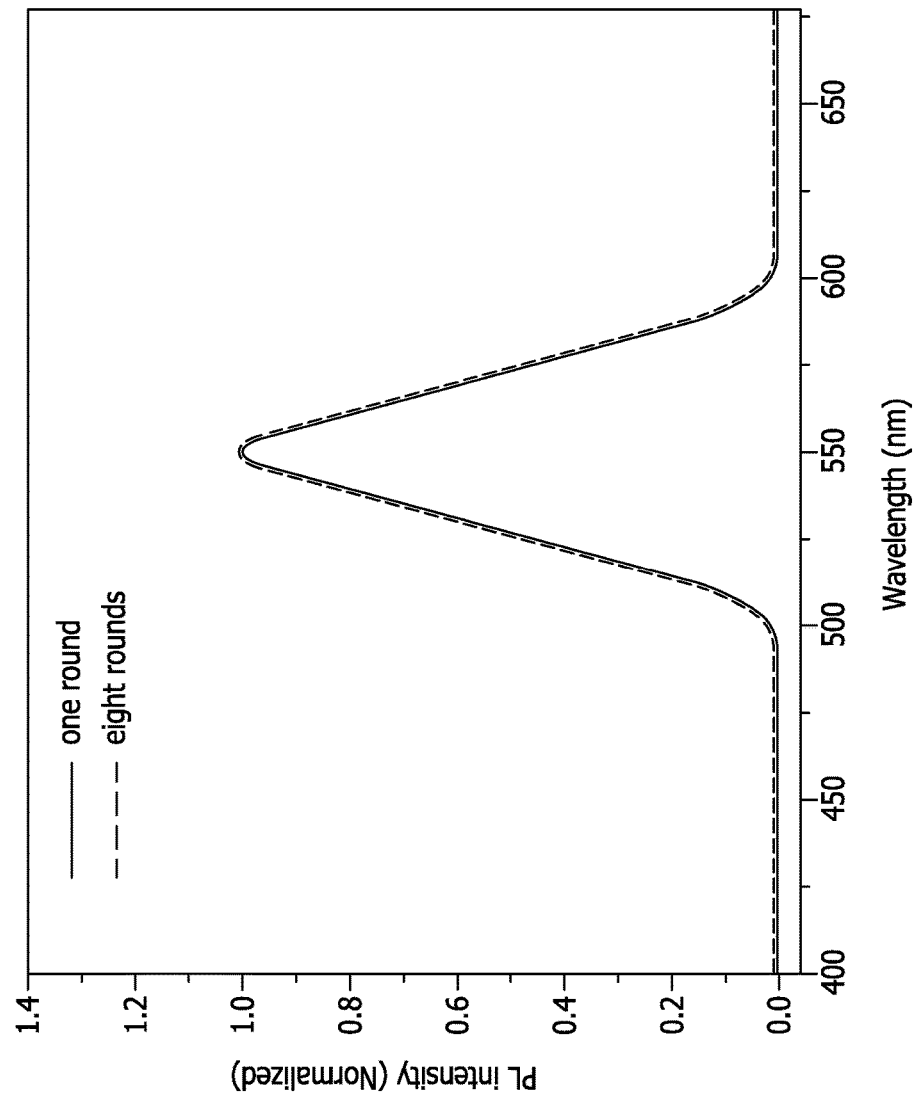

It is understood that coordination of the ligands on the QDs is not irreversible. See References 14 and 41. There is equilibrium between bound and free ligands in the dispersions, with stronger coordination producing lower dissociation constant and vice versa. Phase transfer performed via ligand exchange is usually carried in the presence of large excess of the new ligands (i.e., process is mass action driven). Thus, following ligand exchange dispersions are routinely purified by removing as much as possible the fraction of free solubilized ligands by applying precipitation using a solvent mixture when organic media are used. For dispersions in buffer media, free ligands are removed by applying a few rounds of concentration/dilution using a membrane centrifugation device (with a defined cutoff molecular weight, as described in the experimental section). This procedure relies on the ability of centrifugal forces to extrude the solvent along with solubilized small molecules including ligands through the membrane filter to counter the osmotic pressure in the dispersion (due to a lower chemical potential of the mixture). If the procedure is excessively applied, ligand desorption can shift the equilibrium, resulting in instability buildup and eventually aggregation of the nanoparticles. When using DHLA and DHLA-based ligands for stabilizing QDs we often applied the above procedure 3-4 times, while finding that stickiness to membrane can take place when more than 5 rounds are applied using ~2000 g for ~7-10 minutes. See Reference 71. We tested the colloidal stability of QDs photoligated with bis(LA)-PEG and AuNPs capped with the same ligand, by extending the rounds of centrifugation/dilution applied to dispersions of both materials. We found that the bis(LA)-PEG-OCH$_3$ ligands significantly reduced the ligand desorption rate and provided homogeneous and aggregate-free QD dispersions in buffer media even after 8 and 9 rounds of purification. FIGS. 5A and 5B show that the absorption and emission spectra of QDs were essentially unchanged between the first and eighth round. When the test was carried out using AuNPs, additional 10 rounds of membrane centrifugation was applied for LA-PEG-AuNPs and bis(LA)-PEG-AuNPs dispersions following ligand exchange (data not shown). In both cases, the AuNP dispersions stayed homogeneous, with no aggregate-buildup. This can be attributed to the strong coordination between thiol/sulfur and Au atoms in these dispersions.

The above results combined are promising and further confirm that higher coordination ligands bind stronger onto the QD surfaces, thus greatly improved the colloidal stability in buffer solutions and against centrifugation forces. They also clearly demonstrate that higher coordination provides better resistance to AuNPs against sodium cyanide digestion. Our data also showed that higher PEG branching (i.e., LA-(PEG-OCH$_3$)$_2$) yielded slightly better protection of the NPs compared to LA-PEG ligands, attributed to the denser PEG packing on the nanoparticle surfaces.

VII. Intracellular Delivery of QD-Transferrin Conjugates.

Figure 6A:
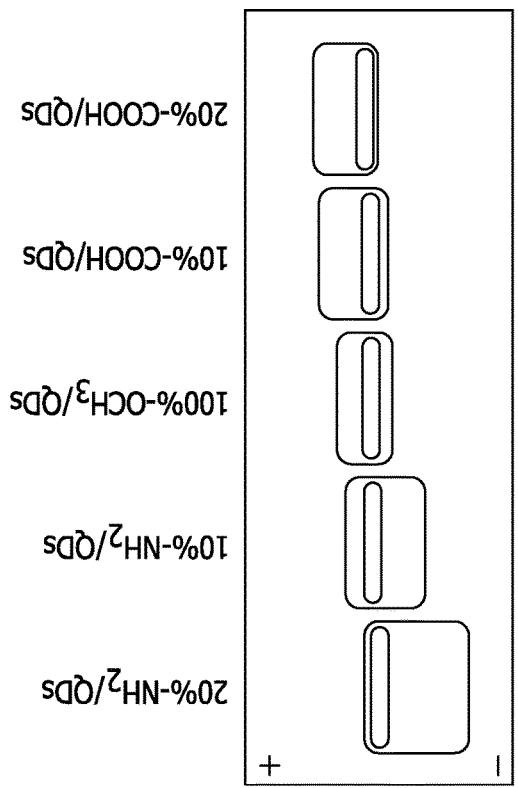
FIG. 6A is a gel electrophoresis image of QDs photoligated with a mixture of bis(LA)-PEG-NH$_2$/bis(LA)-PEG-OCH$_3$ and bis(LA)-PEG-COOH/bis(LA)-PEG-OCH$_3$ with different molar fractions of reactive ligands; the dispersion of 100% bis(LA)-PEG-OCH$_3$-QDs was used as control. The intensity difference of the spots is due to the slightly different amount of QD materials used when running the gel.
Figure 6B:
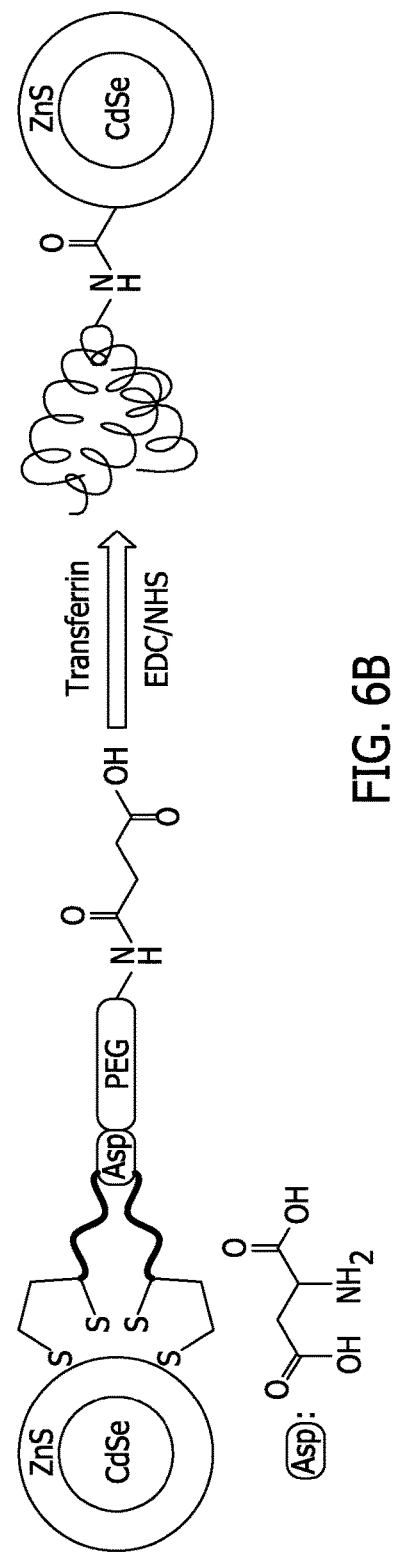
FIG. 6B is a schematic representation of the coupling between bis(LA)-PEG-COOH-QDs and transferrin via EDC/NHS coupling.
Figure 6C:
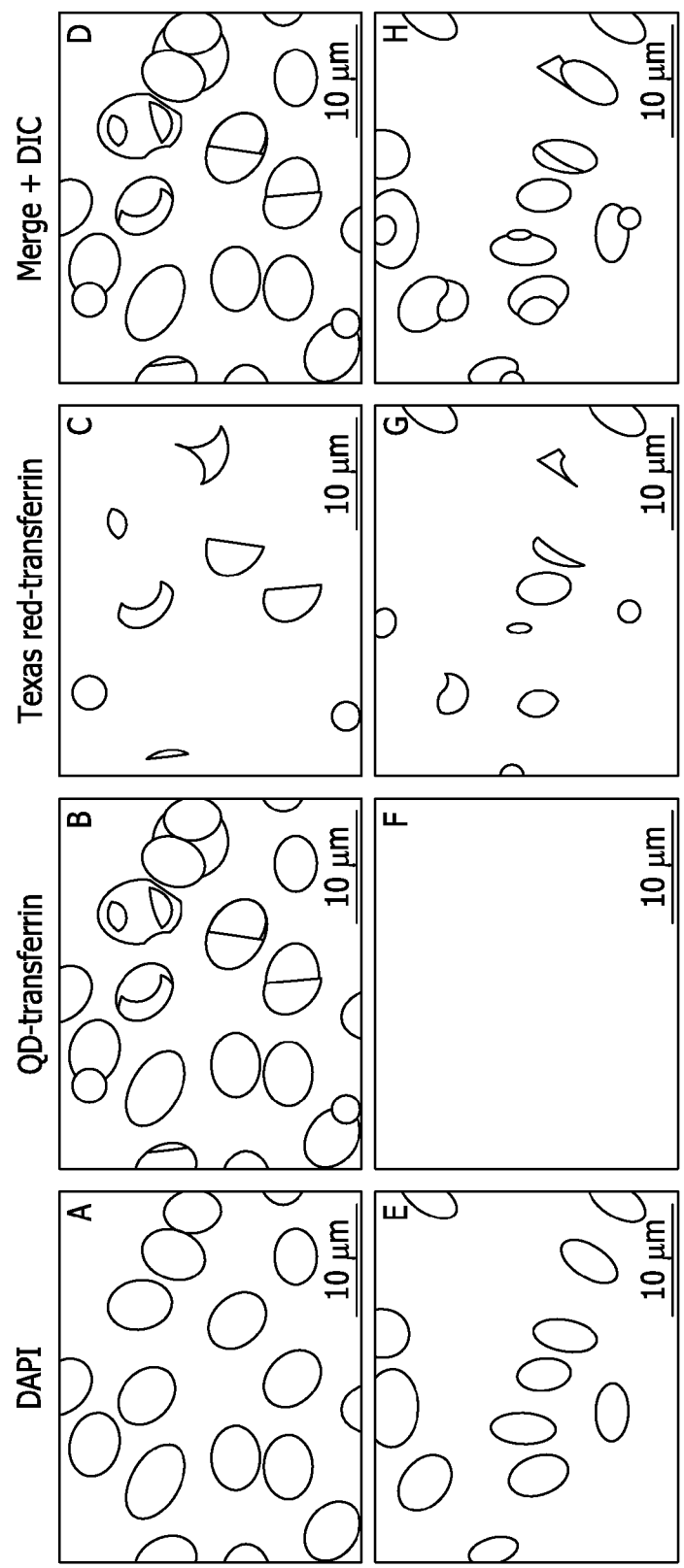
FIG. 6C are representative epifluorescence images of the QD-transferrin cellular delivery. Hela cells were incubated with green emitting QD-transferrin ($\lambda_{em}$=540 nm, 150 nM) (A-D) and nonconjugated QDs ($\lambda_{em}$=540 nm, 150 nM) (E-H) for 1.5 hrs. The fluorescence images of cell nuclei counterstained with DAPI, QD-transferrin, endosomes stained with Texas Red and the merged images for both cases are provided.

Our design can be combined with the use of mixed ligand exchange to prepare QDs that present varying numbers of reactive groups. This can be achieved by introducing (during the ligation step) a controllable fraction of —COOH, —NH$_2$, or N$_3$-modified ligands along with the inert-terminated ones. The gel electrophoresis image in FIG. 6A shows that the gel mobility shift of the QDs depends on the nature and fraction of terminally-modified ligands introduced during the phase transfer step. See Reference 49. We utilized 540 nm-emitting QDs photoligated with 15% bis(LA)-PEG-COOH to carry out covalent coupling of transferrin to the QDs via EDC/NHS coupling. See FIG. 6B. The coupling reaction targeted available amines on the protein surface. The formed conjugates were further tested for their biological activity by incubating the QD-transferrin conjugates (150 nM) with HeLa cells at 37° C. for 1 hour; transferrin is a glycoprotein that binds to specific receptors on the cell surface, promoting its transport inside the cell via receptor-mediated endocytosis. See Reference 73. Cells incubated with non-conjugated QDs or with Texas Red-Transferrin provided negative and positive control experiments, respectively. A representative set of epifluorescent images, shown in FIG. 6C (panels A-D), indicate that an efficient intracellular uptake of the QD-transferrin conjugates has taken place. The QD fluorescence (panel B) was mostly distributed in the perinuclear region of the cells; the nuclei were counterstained with DAPI. Additionally, the fluorescence pattern of the QDs was co-localized with that of Texas Red dye-labeled transferrin (panel C), indicating that the nanocrystals were primarily distributed within the endosomal compartments. We did not observe any detectable fluorescence signal for the control culture incubated with QDs only, indicating the absence of nonspecific interactions of the QDs with the cell membrane (see FIG. 6D, panels E-H).

VIII. QD-Peptide-Cy3 Conjugates and FRET Analysis.

Several QD-based sensors using energy or charge transfer interactions (as transduction mechanisms) have been designed over the past decade using QD-conjugates, to detect properties such as changes in the environment pH, the presence of metal ions and for monitoring enzymatic activity. See References 74 through 77. Designing of QD sensors greatly benefits from the ease of stable surface and ease of coupling with biomolecules of interest.

Figure 7A:
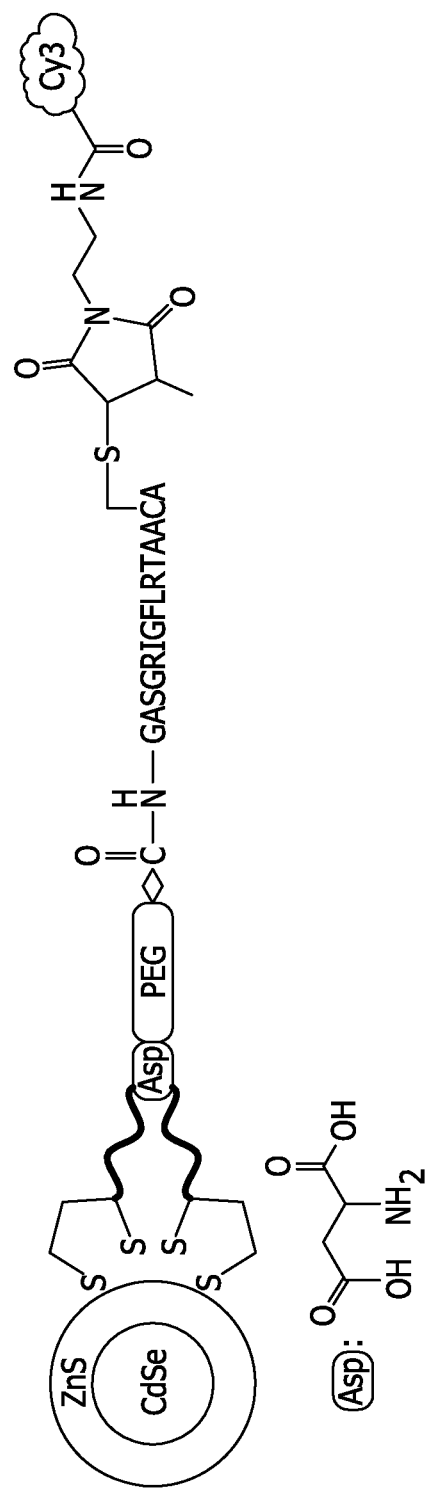
FIG. 7A is a schematic representation of the coupling of COOH-QDs with Cy3 pre-labeled peptide, the sequence of the peptide used is provided. The UV-vis absorption (FIG. 7B) and PL spectra (FIG. 7C) of 5% and 10% COOH-QDs ($\lambda_{em}$=522 nm) conjugated with the peptide-Cy3 via EDC/NHS coupling; QDs alone and dye alone were used as control.
Figure 7B:
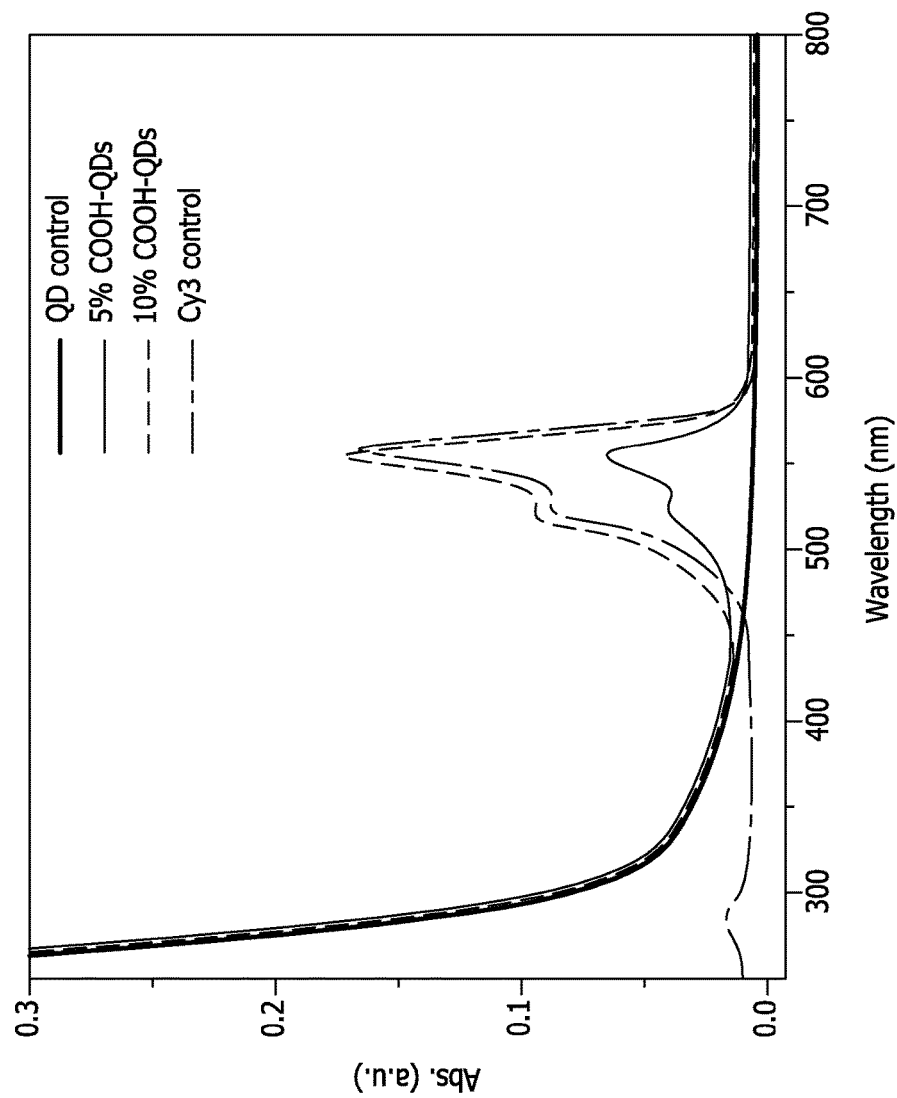
Figure 7C:
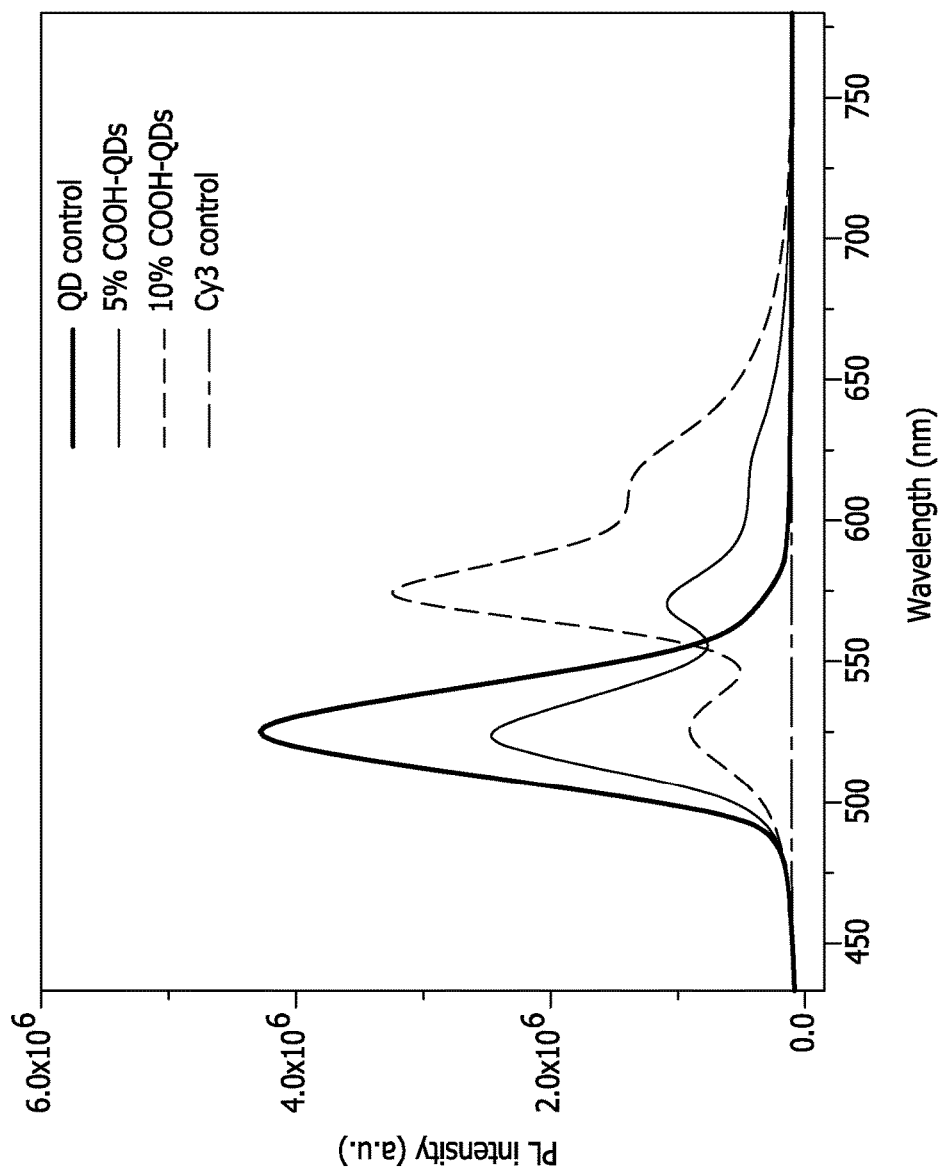

We have probed the assembly of QD-peptide-dye conjugates formed by coupling the COOH (on bis(LA)-PEG-QDs) with the peptide sequence shown in FIG. 7A. The C-terminal cysteine of the peptide was first reacted with maleimide-Cy3 dye, yielding Cy3-labeled peptide, then the N-terminal amine was further conjugated with COOH-functionalized QDs, via EDC/NHS coupling; two fractions of carboxylic acid modified QDs (5% and 10%) were used. The composite absorption spectra (FIG. 7B) collected from dispersions of the purified conjugates show contributions from the QDs and Cy3 dye; additionally, the dye contribution to the spectra varied with the fraction of COOH-modified ligands used in the ligand exchange step, indicating that the number of —COOH per QD tracked the fraction of bis(LA)-PEG-COOH ligands used. FIG. 7C also shows the emission spectra collected from the same dispersion. There is a progressive loss in QD emission combined with enhancement in the dye PL. Since the samples were excited at 400 nm where direct excitation of dye is minimal, we attribute the observed fluorescence data to efficient resonance energy transfer between the QDs and bound Cy3, producing strong quenching of the QD signal along with sizable sensitization of the dye fluorescence. See FIG. 7C. This was further supported by the pronounced shortening in the QD PL radiative decay time.

The absorption data were combined with the extinction coefficients of Cy3 ($1.5 \times 10^5$ M$^{-1}$cm$^{-1}$ at $\lambda$=552 nm) and green-emitting QDs ($3.348 \times 10^5$ M$^{-1}$cm$^{-1}$ at $\lambda$=350 nm), deduced from size and cross-section absorption measurements reported in previous studies, to extract an estimate for the number of Cy3 (n) attached to a QD. We measured n≈4 and n≈12 for conjugates prepared with 5% and 10% COOH-modified ligands, respectively. See References 78 and 79. Similarly, analysis of the deconvoluted fluorescence spectra within the Förster FRET model provided additional estimate for the valence. Assuming a centro-symmetric QD-peptide-dye configuration where acceptors are arrayed around the central donor at a fixed separation distance, the expression for the quenching efficiency, $E_n$, is given by:

$$E_n = \frac{nR_0^6}{nR_0^6 + r^6} \quad (2)$$

Where r represents the separation distance from the donor (QD) to the acceptors and R$_0$ is the Förster radius corresponding to $E_{n=1}$=0.5. See Reference 80.

For our system, we used R$_0$≈52 Å, extracted from the experimental spectral overlap and a Q$_D$ value of ~18%. We also used estimates for the QD radius≈27 Å (core-shell), the capping layer including a coiled PEG chain in good solvent conditions (end-to-end distance of ~23 Å), a peptide segment of ~11 Å and the size of the maleimide-dye ~5 Å, to extract a value for the center-t-center separation distance r of ≈66 Å. See References 70 and 81. Using this information and equation 2, we estimated that n≈4 for 5% COOH-QDs and ≈11 for 10% COOH-QDs. These values are in reasonable agreement with the values obtained from absorption spectra. The high FRET efficiencies measured for our QD-peptide conjugates proves that our ligand design provides compact QDs and QD-conjugates.

We should note that the peptide structure shown in FIG. 7A includes a sequence expected to be specifically recognized and cleaved by the enzyme matrix metalloproteinase (MT1-MMP), an extremely important indicator of cancer in cell cultures and tissue. We will pursue measurements of the kinetics of enzyme digestion of the dye-peptide substrate on the QDs both in solution and in cancer cell lines, and hope to report on those findings in future publications.

Starting from the aspartic acid, as a precursor, we synthesized several molecular scale multi-functional PEG-based ligands that present two and four coordinating groups and varying architectures. Ligands prepared and tested include bis(LA)-PEG and LA-(PEG)$_2$. This design exploits the availability of two carboxyl and one amine groups in the chiral L-aspartic acid and combines that with the use of BOC protective and carbodiimide chemistries to synthesize several capping ligands with controlled architecture, coordination and reactivity. The ligands were applied to cap AuNPs and QDs and transfer them to buffer media. The resulting nanoparticles exhibited great long-term colloidal stability over a broad range of conditions. We have also shown that the synthetic strategy permits the attachment of reactive groups including azide, amine and carboxylic acid, on the same ligand. This allowed conjugation of QDs with biomolecules (transferrin protein and peptide). These were tested for cellular uptake and energy transfer interactions.

QDs or AuNPs coated with these ligands would be greatly useful in sensing applications, based on FRET and CT interactions including sensing of soluble ions and enzymatic activity. The hydrophilic NPs described here are also promising for intracellular sensing and imaging where colloidal stability at very low concentrations combined with multi-functionality are highly desired. The bis(LA)-PEG and LA(PEG)$_2$ ligands provide the means to probe the effects of coordination versus steric interactions on the ligand density on inorganic nanocrystals. We should emphasize that amino-acids are promising platforms for developing novel organic ligands and the synthetic strategy applied here can be potentially applied to other precursors, such as lysine, to provide ligands for stabilizing other inorganic nanoparticles.

EXAMPLES

The following non-limiting examples are provided to further illustrate the present invention.

Example 1

Experimental Section

Materials.

Poly(ethylene glycol) with molecular weight 600 and 1000 were purchased from Acros Organics (Morris Plains, N.J.). Poly(ethylene glycol) methyl ether (molecular weight of 750), aspartic acid, lipoic acid (LA), N,N-dicylohexyl-carbodiimide (DCC), 4-(N,N-dimethylamino)pyridine (DMAP), di-tert-butyl dicarbonate (Boc$_2$O), triphenylphosphine, succinic anhydride, 4M HCl in dioxane, triethylamine, tetramethylamonium hydroxide (TMAH), and organic solvents (chloroform, methanol, hexane, ethyl acetate, etc.) were purchased from Sigma Chemicals (St. Louis, Mo.). Phosphate salts used for buffer preparation, NaCl, Na$_2$CO$_3$, and Na$_2$SO$_4$ were also purchased from Sigma Chemicals. Hydroxybenzotriazole (HOBt.H$_2$O) was purchased from Alfa Aesar (Ward Hill, Mass.). Column chromatography purification was performed using silica gel (60 Å, 230-400 mesh, from Bodman Industries, Aston, Pa.). Sulfo-Cy3 maleimide dye and PD-10 column were purchased from GE Healthcare (Piscataway, N.J.). Deuterated solvents used for NMR experiments were purchased from Cambridge Isotope Laboratories Inc. (Andover, Mass.). The chemicals and solvents were used as received unless otherwise specified. All synthetic reactions described here were carried out under nitrogen atmosphere, unless otherwise specified. Standard nitrogen vacuum manifold technique was used to carry out chemical reactions when needed, and air sensitive materials were handled in an MBraun Labmaster 130 glovebox (Stratham, N.H.).

Instrumentation.

$^1$H NMR spectra were collected using a Bruker Spectro-Spin 600 MHz spectrometer (Bruker SpectroSpin, Billerica, Mass.). A Shimadzu UV-Vis absorption spectrophotometer (UV 2450 model, Shimadzu, Columbia, Md.) was used to measure the UV-vis absorption spectra from the various dispersions, while the fluorescence spectra were collected on a Fluorolog-3 spectrometer (Jobin Yvon Inc., Edison, N.J.) equipped with PMT and CCD detectors. Solvent evaporation (to concentrate or dry samples) was carried out using a lab-scale Buchi rotary evaporator R-215 (New Castle, Del.). The photoligation experiments were carried out using a UV photo-reactor Model LZC-4V (Luzchem Research Inc., Ottawa, Canada). Gel electrophoresis experiments were performed using a 1% agarose gel. Samples were prepared by diluting dispersions of QDs or QD-conjugates in a TBE buffer (100 m MTris, 83 mM boric acid, 1 mM EDTA, pH8.4), then mixing with loading buffer (2.5% ficoll 400, 1.6 mM Tris-HCl, 8.3 mM EDTA, pH7.4). Aliquots of these dispersions were loaded into the agarose gel and run for 20 min using an applied voltage of 8.0 V/cm. Gel images were captured in the fluorescence mode using a Gel Doc XR+ System.

Ligand Synthesis.

The set of ligands prepared in this study, either made of one PEG moiety appended with two lipoic acid anchoring groups (bis(LA)-PEG), or made of two PEG moieties attached onto one lipoic acid (LA-(PEG)$_2$) were all prepared starting from the aminoacid aspartic acid as precursor. Our synthetic route also allows easy functionalization of the ligands with various terminal reactive functions such as azide, amine and acid groups. The poly(ethylene glycol) precursors used for the synthesis, namely NH$_2$-PEG$_{750}$-OCH$_3$ and NH$_2$-PEG$_{1000}$-N$_3$ were prepared and purified following protocols described in our previous reports.[54,71] These ligands were applied as, to cap exchange with oleylamine-AuNPs. They were, however, combined with the photochemical modification of lipoic acid to achieve in-situ ligand exchange and phase transfer of TOP/TOPO-capped QDs. FIG. 1 shows the chemical structures along with the synthetic steps used for preparing of the various ligands. Below, we detail the synthetic protocols used for preparing these ligands.

Example 2

Compound 1 (Boc-Asp)

In a 500 mL one-neck round bottom flask, aspartic acid (Asp, 4 g, ~30 mmol), 1,4-Dioxane (120 mL) and H$_2$O (60 mL) were mixed yielding a heterogeneous solution. An aqueous solution of NaOH (1 M) was added to the mixture with constant stirring until the solution became homogeneous and clear indicating that the aspartic acid was completely dissolved. The solution was cooled using an ice-bath, then di-tert-butyl dicarbonate (Boc$_2$O, 7.2 g, ~33 mmol) dissolved in 1,4-Dioxane (20 mL) was added dropwise. The reaction mixture was then stirred at room temperature overnight. Once the reaction was complete, the solvent was partially evaporated, using a rotary evaporator, to a final volume of ~30 mL. Then, EtOAc (20 mL) was added and the water layer was acidified under ice-cold conditions using an aqueous solution of KHSO$_4$ to pH2. The solution mixture was transferred to a separatory funnel and the product was extracted using EtOAc (volume, 3 times). The organic layers were combined and dried over Na$_2$SO$_4$. The solvent was evaporated using rotary evaporator, and further vacuum drying was applied overnight to yield the compound as white solid (~6 g; reaction yield~85%).

$^1$H NMR (600 MHz, DMSO-d$_6$): δ 1.38 (s, 9H), 2.51-2.55 (m, 1H), 2.65-2.69 (m, 1H), 4.24-4.28 (m, 1H), 7.05-7.07 (d, 1H, J=12 Hz), 12.5 (s, 2H).

Example 3

Compound 2 (Boc-Asp-PEG-OCH$_3$)

Boc-Asp, compound 1 (3.1 g, 13.3 mmol) was dissolved in EtOAc (30 mL) in a 100 mL two-neck round bottom flask equipped with a magnetic stirring bar. The solution was purged with N$_2$ and cooled to ~0° C. using an ice bath, then a solution of DCC (3.01 g, 14.6 mmol) in EtOAc (30 mL) was added dropwise through an additional funnel over ~20 minutes. Once the addition was complete, the mixture was gradually warmed up to room temperature and was continuously stirred for another 4 hrs. The solid byproduct was first removed using a filter paper and the solvent was evaporated to provide the DCC activated Boc-aspartic acid compound as a white solid. This compound was mixed with $NH_2$-$PEG_{750}$-$OCH_3$ (14.7 g, 20 mmol) and THF (100 mL) in a 250 mL three-neck round bottom flask and the solution was refluxed at 66° C. overnight. The reaction mixture was cooled to room temperature, filtered through a filter paper and chromatographed on a silica column (230-400 mesh). A one round elution with $CHCl_3$ was first applied to remove impurities, and the product was collected using 40:1 (vol/vol) mixture of $CHCl_3$:MeOH as the eluent. After evaporating the solvent, light yellowish oil was collected (~11 g; reaction yield~90%).

$^1$H NMR (600 MHz, $CDCl_3$): δ 1.39 (s. 9H), 2.56-2.60 (m, 1H), 2.91-2.95 (m, 1H), 3.33 (s, 3H), 3.49-3.51 (m, 3H), 3.59-3.60 (m, 64H), 4.43-4.47 (m, 1H), 5.75-5.76 (br, 1H), 6.97 (br, 1H).

Example 4

Compound 3 (LA-Asp-PEG-$OCH_3$)

In a round bottom flask, compound 2 (7.1 g, 7.5 mmol) was mixed with THF (50 mL) and cooled under ice cold condition. A mixture of DCC (2 g, 9.7 mmol) and HOBt.$H_2O$ (1.5 g, 9.8 mmol) dissolved in 15 mL THF was added to the reaction flask dropwise under $N_2$ atmosphere with constant stirring. After the addition was complete, the solution was gradually warmed up to room temperature and stirred for 1 hr. LA-ethylenediamine (2.8 g, 11.3 mmol) dispersed in 5 mL $CHCl_3$ was added dropwise via a syringe; LA-ethylenediamine was pre-synthesized following previous literature protocols. See Reference 82. The reaction mixture was left stirring at room temperature for two days, then filtered through a filter paper. The compound was then purified on a silica gel column in 2 steps: impurities were first removed by elution with $CHCl_3$. Then the compound was eluted using 30:1 (vol:vol) $CHCl_3$:MeOH solvent mixture. Following evaporation of the solvent the product was collected as a yellow oil (~6.7 g; reaction yield~76%).

$^1$H NMR (600 MHz, $CDCl_3$): δ 1.42-1.48 (m, 11H), 1.61-1.73 (m, 4H), 1.87-1.93 (m, 1H), 2.21-2.23 (t, 2H, J=6 Hz), 2.42-2.48 (m, 1H), 2.57-2.60 (m, 1H), 2.71-2.74 (m, 1H), 3.08-3.12 (m, 1H), 3.14-3.18 (m, 1H), 3.37 (s, 3H), 3.39-3.45 (m, 4H), 3.52-3.55 (m, 5H), 3.63 (m, 65H), 4.45-4.49 (m, 1H), 6.20 (br, 1H), 6.91 (br, 1H), 6.99 (br, 1H).

Example 5

Compound 4 (bis(LA)-PEG-$OCH_3$)

In a round bottom flask, 15 mL of 4 M HCl in 1,4-Dioxane was added to compound 3 (6.7 g, 5.7 mmol) under ice cold conditions and left stirring for 4 hrs at room temperature. The solvent was evaporated using rotary evaporator followed by dispersion in $H_2O$ (70 mL). This aqueous solution was transferred to a separation funnel and washed with diethyl ether (50 mL, two times). The aqueous layer was collected, basified using saturated $Na_2CO_3$ to ~pH 9, and the compound was extracted using $CHCl_3$ (50 mL, three times). The solvent was finally evaporated to obtain the Boc-deprotected product (compound 4', 5.5 g, yield~90%). This Boc-deprotected compound (5.5 g, 5.1 mmol) was mixed with LA (1.6 g, 7.8 mmol) and DMAP (0.2 g, 1.6 mmol) in $CHCl_3$ (50 mL) and the mixture was cooled to ~0° C. under ice cold conditions. DCC (1.6 g, 7.8 mmol) dissolved in $CHCl_3$ (15 mL) was added dropwise, then the reaction was stirred for two days at room temperature. Dicyclohexylurea (DCU) was removed by filtration, and the chloroform layer was further washed with saturated sodium carbonate solution (30 mL, two times) to remove excess unreacted lipoic acid. The solution was concentrated and purified on a silica gel column using a 30:1 (vol:vol) $CHCl_3$:MeOH as eluent. After solvent evaporation, the product was finally collected as a yellow solid (~4.5 g; reaction yield~70%).

$^1$H NMR (600 MHz, $CDCl_3$): δ 1.46-1.51 (m, 4H), 1.65-1.73 (m, 8H), 1.9-1.95 (m, 2H), 2.22-2.24 (t, 2H, J=6 Hz), 2.26-2.28 (t, 2H, J=6 Hz), 2.45-2.85 (m, 2H), 2.53-2.57 (m, 1H), 2.67-2.7 (m, 1H), 3.11-3.18 (m, 2H), 3.18-3.22 (m, 2H), 3.39 (s, 3H), 3.44-3.47 (m, 4H), 3.55-3.59 (m, 8H), 3.65 (m, 65H), 4.74-4.77 (m, 1H), 6.80 (br, 1H), 6.90 (br, 1H), 7.40 (br, 1H).

Example. 6

Compound 5 (Boc-Asp-PEG-$N_3$)

Boc-aspartic acid (compound 1, 2.1 g, 9.0 mmol) was dissolved in EtOAc (30 mL) using a 100 mL two-neck round bottom flask equipped with a magnetic stirring bar. The solution was cooled using an ice bath, purged with $N_2$, and DCC (2.04 g, 9.9 mmol) dissolved in EtOAc (20 mL) was added dropwise. The reaction was gradually warmed up to room temperature and left stirring for 4 hrs. The solid byproduct was first removed using a filter paper, followed by solvent removal using a rotary evaporator. The obtained white powder was mixed with $NH_2$-$PEG_{1000}$-$N_3$ (14 g, 13.5 mmol, dissolved in 100 mL THF) and refluxed at 66° C. overnight. The product mixture was filtered through filter paper, dried over $Na_2SO_4$, concentrated using rotary evaporator and chromatographed on a silica gel column. The pure product was collected using a solvent mixture of $CHCl_3$:MeOH (20:1 by volume) for elution. A light yellow oil was collected after evaporating the solvent (~10 g; reaction yield~90%).

$^1$H NMR (600 MHz, $CDCl_3$): δ 1.38 (s, 9H), 2.62-2.66 (m, 1H), 2.82-2.94 (m, 1H), 3.33-3.34 (m, 5H), 3.47-3.5 (m, 5H), 3.59 (m, 90H), 4.39-4.43 (m, 1H), 5.56-5.57 (br, 1H), 6.80 (br, 1H).

Example 7

Compound 6 (LA-Asp-PEG-$N_3$)

Compound 5 (5 g, 4 mmol) and THF (40 mL) were mixed in a 100 mL two-neck round bottom flask equipped with a magnetic stirring bar. A solution mixture of DCC (1.1 g, 5.3 mmol), HOBt.$H_2O$ (0.8 g, 5.2 mmol) and THF (10 mL) was added to the flask dropwise under ice cold conditions. The mixture was stirred at room temperature for 1 hour, then LA-ethylenediamine (1.48 g, 6 mmol) dissolved in 5 mL $CHCl_3$ was subsequently added dropwise. The reaction mixture was left stirring at room temperature and under $N_2$ atmosphere for two days. Once the reaction was completed, the mixture was filtered using a filter paper (to remove a white solid byproduct), and the solution was concentrated under vacuum using a rotary evaporator, then purified on a silica gel column using a mixture of 30:1 (vol:vol) $CHCl_3$:MeOH as eluent. The product was collected as yellow oil (~4.7 g; reaction yield~79%).

¹H NMR (600 MHz, CDCl₃): δ 1.42-1.46 (m, 11H), 1.63-1.69 (m, 4H), 1.86-1.92 (m, 1H), 2.29-2.31 (t, 2H, J=6 Hz), 2.42-2.47 (m, 1H), 2.71-2.74 (m, 1H), 2.75-2.78 (m, 1H), 3.07-3.11 (m, 1H), 3.14-3.18 (m, 1H), 3.37-3.4 (m, 6H), 3.54-3.55 (m, 4H), 3.62 (m, 90H), 4.52-4.55 (m, 1H).

Example 8

Compound 7 (bis(LA)-PEG-N₃)

De-protection of the BOC group was applied to compound 6: 4 M HCl in 1,4-dioxane (15 mL) was added to 4 g (2.7 mmol) of compound 6 and the mixture was stirred for 4 hours at room temperature. The purification was carried out following the same procedure used in the synthesis of compound 4, as detailed above. This de-protected product (compound 7', 3 g, 2.17 mmol), LA (0.67 g, 3.25 mmol) and DMAP (0.08 g, 0.66 mmol) were dissolved in 20 mL CHCl₃, followed by dropwise addition of a DCC solution in CHCl₃ (0.67 g, 3.25 mmol, 10 mL) under ice cold conditions. The reaction mixture was purged with N₂ and stirred for 2 days at room temperature. A white solid byproduct was removed by filtration, the CHCl₃ layer was washed with saturated Na₂CO₃ solution (15 mL, two times), then the solution mixture was purified on a silica gel column using 30:1 (vol:vol) CHCl₃:MeOH mixture as the eluent to obtain the compound 7 as a yellow solid (~2.3 g; reaction yield~67%).

¹H NMR (600 MHz, CDCl₃): δ 1.42-1.47 (m, 4H), 1.64-1.69 (m, 8H), 1.86-1.92 (m, 2H), 2.21-2.23 (t, 2H, J=6 Hz), 2.24-2.26 (t, 2H, J=6 Hz), 2.42-2.48 (m, 2H), 2.65-2.69 (m, 1H), 2.78-2.82 (m, 1H), 3.08-3.12 (m, 2H), 3.15-3.19 (m, 2H), 3.4-3.43 (m, 5H), 3.51-3.56 (m, 6H), 3.63 (m, 90H), 4.70-4.75 (m, 1H), 6.90 (br, 1H), 7.10 (br, 1H), 7.40 (br, 1H).

Example 9

Compound 8 (bis(LA)-PEG-NH₂)

Compound 7 (2.9 g, 1.86 mmol) was dissolved in THF (50 mL) at room temperature with constant stirring; a slight heating may be required to ensure that the compound is completely dissolved. Triphenylphosphine (0.73 g, 2.8 mmol) was added (at room temperature) and the reaction mixture was stirred for 40 minutes under N₂, followed by addition of H₂O (0.33 mL, 18.3 mmol), and the reaction mixture was further left stirring overnight. Once the reaction was complete, the solvent was evaporated using a rotary evaporator, then EtOAc was added to the residue and stirred with slight heating (~60° C.) to dissolve the compound. The solution was transferred to a separatory funnel, to which 1 M HCl (50 mL) was added. The organic layer was removed and the aqueous layer was further washed with EtOAc (40 mL, 1 time) to remove the remaining impurities. Saturated Na₂CO₃ solution was added to the aqueous layer to basify the solution (~pH 9). The final product was extracted with CHCl₃ (50 mL, three times), dried over Na₂SO₄ and collected after evaporating the solvent as yellow oil (~1.8 g; reaction yield~62%).

¹H NMR (600 MHz, CDCl₃): δ 1.42-1.47 (m, 4H), 1.63-1.68 (m, 8H), 1.85-1.89 (m, 2H), 2.18-2.20 (t, 2H, J=6 Hz), 2.22-2.24 (t, 2H, J=6 Hz), 2.42-2.48 (m, 2H), 2.53-2.56 (m, 1H), 2.75-2.79 (m, 1H), 2.83-2.87 (t, 2H, J=6 Hz), 3.08-3.12 (m, 2H), 3.15-3.19 (m, 2H), 3.33-3.39 (m, 6H), 3.51-3.56 (m, 6H), 3.63 (m, 90H), 4.71-4.75 (m, 1H).

Example 10

Compound 9 (bis(LA)-PEG-COOH)

Bis(LA)-PEG-NH₂ (compound 8, 1 g, 0.65 mmol), succinic anhydride (0.13 g, 1.3 mmol), triethylamine (0.23 mL, 1.69 mmol) and CHCl₃ (20 mL) were mixed in a 100 mL one-neck round bottom flask. The mixture was stirred at room temperature overnight under N₂ atmosphere. The solvent was removed under vacuum and 1 M HCl (20 mL) was added to the residue. The product was further extracted using CHCl₃ (30 mL, three times). The organic layers were combined, dried over Na₂SO₄, filtered through a filter paper, and the solvent was evaporated, yielding the final product (compound 9) as a yellow oil (~0.63 g; reaction yield~60%).

¹H NMR (600 MHz, CDCl₃): δ 1.4-1.46 (m, 4H), 1.64-1.7 (m, 8H), 1.88-1.93 (m, 2H), 2.24-2.29 (m, 4H), 2.44-2.49 (m, 2H), 2.54-2.56 (m, 1H), 2.61-2.65 (m, 4H), 2.74-2.78 (m, 1H), 3.09-3.12 (m, 2H), 3.14-3.19 (m, 2H), 3.34-3.4 (m, 6H), 3.50-3.55 (m, 6H), 3.64 (m, 90H), 4.72-4.75 (m, 1H).

Example 11

Compound 10 (Boc-Asp-(PEG-OCH₃)₂)

Compound 1 (1 g, 4.29 mmol), NH₂-PEG₇₅₀-OCH₃ (7.6 g, 10.34 mmol) and DMF (20 mL) were mixed in a 100 mL two-neck round bottom flask equipped with a magnetic stir bar. The solution was stirred at room temperature until all the solid materials were fully dissolved. DCC (1.9 g, 9.22 mmol) and HOBt.H₂O (1.41 g, 9.22 mmol) dissolved in DMF (10 mL) were further added dropwise using a syringe under ice cold conditions. Once the addition was complete, the mixture solution was warmed up to room temperature and left stirring for two days under N₂ atmosphere. The reaction mixture was filtered through a filter paper (to remove a white solid byproduct), and then CHCl₃ (40 mL) was added. This solution was further washed with 1 M HCl (20 mL, 1 time) and saturated Na₂CO₃ (20 mL, 1 time), dried by adding Na₂SO₄, and the solvent was evaporated using rotary evaporator. The residue was chromatographed on silica gel column with 25:1 (vol:vol) CHCl₃:MeOH mixture as eluent, yielding the product as a yellow oil (~6.2 g; reaction yield~86%).

¹H NMR (600 MHz, CDCl₃): δ 1.39 (s, 9H), 2.51-2.54 (m, 1H), 2.8-2.83 (m, 1H), 3.33 (s, 6H), 3.4-3.42 (m, 4H), 3.49-3.59 (m, 9H), 3.60 (m, 140H), 4.39 (m, 1H), 6.14-6.15 (br, 1H), 6.7 (br, 1H), 7.14 (br, 1H).

Example 12

Compound 11 (LA-(PEG-OCH₃)₂)

The de-protection of compound 10 and purification of the product were carried out following the same procedure as detailed above for compound 7. The de-protected compound 10 (3 g, 1.91 mmol) was mixed with LA (0.47 g, 2.28 mmol) and DMF (15 mL) in a 100 mL two-neck round bottom flask equipped with a magnetic stirring bar. In a separate vial, a solution of DCC (0.47 g, 2.28 mmol), HOBt.H₂O (0.35 g, 2.28 mmol) in DMF (5 mL) was added dropwise to the reaction solution under ice cold conditions with constant stirring. The reaction solution was gradually warmed up to room temperature and left stirring for another two days to ensure the completeness of the reaction. After filtering off the white solid byproduct, the solution was washed with saturated $Na_2CO_3$ (10 mL, two times), dried over $Na_2SO_4$, and concentrated using a rotary evaporator. The crude product was further purified over silica gel chromatography using 20:1 vol:vol $CHCl_3$:MeOH mixture as eluent to provide a yellow oil paste (~2.5 g; reaction yield~74%).

$^1$H NMR (600 MHz, $CDCl_3$): δ 1.40-1.52 (m, 2H), 1.62-1.72 (m, 4H), 1.87-1.93 (m, 1H), 2.24-2.26 (t, 2H, J=6 Hz), 2.43-2.48 (m, 1H), 2.53-2.57 (m, 1H), 2.81-2.85 (m, 1H), 3.08-3.13 (m, 1H), 3.15-2.29 (m, 1H), 3.37 (s, 6H), 3.42-3.46 (m, 5H), 3.52-3.56 (m, 9H), 3.63 (m, 120H), 4.70-4.72 (m, 1H), 7.05 (br, 1H), 7.34 (br, 1H), 7.46 (br, 1H).

Example 13

Compound 12 (Boc-Asp-(PEG-$N_3$)$_2$)

Boc-aspartic acid (compound 1, 1 g, 4.29 mmol), $NH_2$-$PEG_{1000}$-$N_3$ (10.4 g, 10.27 mmol) and DMF (20 mL) were added to 100 mL two-neck round bottom flask containing a magnetic stir bar. The mixture was stirred until a homogeneous solution was formed. A solution of DCC (1.95 g, 9.46 mmol) and HOBt.$H_2O$ (1.44 g, 9.41 mmol) in DMF (5 mL) was added to the reaction mixture dropwise under ice cold conditions. Once the addition was complete, the reaction solution was gradually warmed up to room temperature and left stirring for two days. A white solid byproduct was filtered off using a filter paper, and the solvent was evaporated under vacuum. The residue was purified over silica gel column using 20:1 vol:vol $CHCl_3$:MeOH mixture as eluent, yielding the product as a yellow oil (~6.2 g; reaction yield~65%).

$^1$H NMR (600 MHz, $CDCl_3$): δ 1.43 (s, 9H), 2.50-2.53 (m, 1H), 2.83-2.87 (m, 1H), 3.36-3.40 (m, 6H), 2.50-2.53 (m, 5H), 3.63 (m, 175H), 4.40-4.44 (m, 1H), 6.14-6.15 (br, 1H), 6.67 (br, 1H), 7.13 (br, 1H).

Example 14

Compound 13 (LA-(PEG-$N_3$)$_2$)

Compound 12 was de-protected and purified following the same procedure as described above. The de-protected compound 12 (3 g, 1.41 mmol), LA (0.35 g, 1.7 mmol), and DMF (10 mL) were mixed in a 100 mL two-neck round bottom flask. The solution was stirred until becoming homogeneous, then cooled to ~0° C. using an ice bath. In a separate vial, DCC (0.32 g, 1.55 mmol) and HOBt.$H_2O$ (0.24 g, 1.55 mmol) were dissolved in DMF (5 mL), and then added to the above reaction mixture under $N_2$ atmosphere. The reaction solution was warmed to room temperature and further stirred for two days. The byproduct (as a white solid) was filtered off using a filter paper, and the residue was purified using silica gel chromatography using 20:1 vol:vol $CHCl_3$:MeOH mixture as eluent. The product was obtained as yellow oil (~2.3 g; reaction yield~70%).

$^1$H NMR (600 MHz, $CDCl_3$): δ 1.38-1.46 (m, 2H), 1.62-1.67 (m, 4H), 1.96-1.92 (m, 1H), 2.21-2.23 (t, 2H, J=6 Hz), 2.41-2.46 (m, 1H), 2.62-2.65 (m, 1H), 2.87-2.91 (m, 1H), 3.05-3.09 (m, 1H), 3.12-3.16 (m, 1H), 3.38-3.41 (m, 6H), 3.52-3.55 (m, 6H), 3.62 (m, 175H), 4.73-4.76 (m, 1H), 6.81-6.89 (br, 2H)

Example 15

Compound 14 (LA-(PEG-$NH_2$)$_2$)

Compound 13 (2 g, 0.87 mmol) was dissolved in THF (40 mL) in a 100 mL one-neck round bottom flask equipped with a magnetic stirring bar, followed by the addition of triphenylphosphine (0.68 g, 2.6 mmol). The solution was stirred at room temperature under $N_2$ atmosphere for 30 min, then $H_2O$ (0.31 g, 17.3 mmol) was added. The reaction mixture was further stirred at room temperature overnight and purified following the same steps as described for preparing bis(LA)-PEG-$NH_2$ (compound 8). The product was collected as yellow oil (~1.2 g; reaction yield~60%).

$^1$H NMR (600 MHz, $CDCl_3$): δ 1.4-1.45 (m, 2H), 1.59-1.65 (m, 4H), 1.85-1.89 (m, 1H), 2.1-2.3 (t, 2H, J=6 Hz), 2.39-2.44 (m, 1H), 2.67-2.73 (m, 1H), 2.83-2.85 (t, 4H, J=6 Hz), 2.84-2.87 (m, 1H), 3.04-3.08 (m, 1H), 3.11-3.15 (m, 1H), 3.37-3.4 (m, 3H), 3.48-3.52 (m, 10H), 3.62 (m, 175H), 4.43-4.46 (m, 1H).

Example 16

Compound 15 (LA-(PEG-COOH)$_2$)

Compound 14 (1 g, 0.44 mmol), succinic anhydride (0.09 g, 0.88 mmol), triethylamine (0.16 mL, 1.15 mmol) and $CHCl_3$ (15 mL) were mixed in a 100 mL one-neck round bottom flask equipped with a magnetic stirring bar. The reaction was stirred at room temperature overnight under $N_2$, then the solvent was evaporated using a rotary evaporator. The residue was dissolved in 1 M HCl (20 mL), and the product was extracted using $CHCl_3$ (40 mL, three times). After drying over $Na_2SO_4$ and evaporating the organic solvent, compound 15 was obtained as yellow oil (~0.6 g; reaction yield~60%).

$^1$H NMR (600 MHz, $CDCl_3$): δ 1.39-1.46 (m, 2H), 1.60-1.66 (m, 4H), 1.86-1.90 (m, 1H), 2.19-2.21 (t, 2H, J=6 Hz), 2.30-2.46 (m, 1H), 2.60-2.66 (m, 8H), 2.70-2.74 (m, 1H), 2.84-2.88 (m, 1H), 3.25-3.09 (m, 1H), 3.11-2.16 (m, 1H), 3.38-3.41 (m, 6H), 3.50-3.55 (m, 6H), 3.63 (m, 180H), 4.70-4.74 (m, 1H).

Example 17

Quantum Dot Synthesis

CdSe—ZnS core-shell QDs with different cores sizes were synthesized by reacting organometallic precursors (e.g., cadmium acetylacetonate and trioctylphosphine selenium) in hot coordinating solvent mixture made of alkylphosphines, alkyphosphine-carboxyl, and alkylamine. See References 32 and 83. As-prepared the QD surfaces were primarily capped with TOP/TOPO ligands making them highly hydrophobic in nature. Ligand exchange with lipoic acid modified ligands prepared as described above was applied to promote their transfer to water media and render them biocompatible. See Reference 45.

Example 18

Photoligation of QDs with LA-modified Ligands

The phase transfer of the QDs relied on the in-situ photochemical transformation of the various LA-modified ligands. We briefly describe the procedure applied to cap the QDs with bis(LA)-PEG-$OCH_3$ and LA-(PEG-$OCH_3$)$_2$ (compound 4 and compound 11) and transfer them to aqueous media. Stock dispersion of TOP/TOPO-capped CdSe—ZnS quantum dots (8 μM, 163 μL) in toluene/hexane mixture was precipitated using ethanol. The turbid mixture was centrifuged at 1900 g for 15 min, the supernatant was discarded, and the solid pellet was redispersed in 500 μL of hexane. In a separate scintillation vial, bis(LA)-PEG-OCH$_3$ (68 mg) or LA-(PEG-OCH$_3$)$_2$ (95 mg) was dissolved in 500 μL of MeOH mixed with a catalytic amount of tetramethylammonium hydroxide (TMAH). The contents of the vials were combined in one vial containing a magnetic stir bar. The vial atmosphere was switched to N$_2$, then placed inside a UV reactor (Luzchem Research Inc., Ottawa, Canada). The reaction mixture was irradiated with UV light ($\lambda_{irr}$ peak at 350 nm, at a power of 4.5 mW/cm$^2$) for 30-40 min with continuous stirring. A complete transfer of the QDs from hexane layer to the bottom methanol layer occurred, indicating ligand exchange of the native TOP-TOPO with the bis(LA)-PEG-OCH$_3$ or LA-PEG$_2$-OCH$_3$ has indeed taken place. The solvents were evaporated under vacuum, then a solvent mixture (made of 1:1:10 in volume MeOH:CHCl$_3$:C$_6$H$_{14}$) was added followed by centrifugation at 1900 g for 6 minutes. The top solvent layer was decanted, the precipitate was mildly dried under vacuum. The resulting QD pellet was readily dispersed in DI water. The water dispersions of QDs were further purified using three rounds of centrifugation using a membrane filtration device (Amicon Ultra, 50 kD) to remove the free unbound ligands. The same protocol can be applied to prepare QDs that are functionalized with reactive groups such as —N$_3$, —NH$_2$ and —COOH. Here we simply mix a small fraction of bis(LA)-PEG-N$_3$, bis(LA)-NH$_2$ or bis(LA)-PEG-COOH with the inert bis(LA)-PEG-OCH$_3$ ligands and follow the steps described above. Similarly, hydrophilic and reactive QDs were prepared using a mixture of LA-(PEG-OCH$_3$)$_2$ and —N$_3$, —NH$_2$ and —COOH-appended ligands and following the same steps. Note: the dissolution of bis(LA)-PEG-OCH$_3$ ligands in water requires slight heating and continuous stirring. However, once the disulfide ring is opened followed by ligation with QDs, the obtained nanoparticles are readily dispersed in DI water.

Example 19

Ligand Exchange on AuNPs

Hydrophobic oleylamine-stabilized AuNPs with a hydrodynamic radius of 10 nm were prepared following a previously detailed synthetic scheme and stored in hexane.[84] Cap exchange of these AuNPs with bis(LA)-PEG-OCH$_3$ and LA-(PEG-OCH$_3$)$_2$ was carried out following the same protocol. Here, we briefly describe the cap exchange using bis(LA)-PEG-OCH$_3$ ligands using either two-phase or one-phase configuration. 100 μL of a stock dispersion of oleylamine-AuNPs (30 nM, in hexane) was further added with hexane solvent to a total volume of 500 μL. 20 mg of bis(LA)-PEG-OCH$_3$ dissolved in 500 μL of MeOH were added to the above dispersion of AuNPs in hexane, and the mixture was left stirring at room temperature overnight. This produces a phase transfer of the AuNPs from top hexane layer to bottom methanol layer, indicating that oleylamine has been replaced by bis(LA)-PEG-OCH$_3$ ligands. The procedure is also expected to induce a reduction of LA to DHLA.[49] The bis(LA)-PEG-OCH$_3$—AuNPs were purified and dispersed in DI water, by first evaporating the solvent(s), re-dispersion in a solvent mixture, and centrifugation, using the same conditions as done above for the QDs. Finally 2-3 rounds of centrifugation using a membrane filtration device (Amicon Ultra, 50 kD) was used to remove the remaining unbound ligands. Conversely, the single phase configuration utilized THF as the solvent. Briefly, starting with 100 μL of oleylamine-AuNPs (30 nM in hexane), the solvent was evaporated under vacuum then bis(LA)-PEG-OCH$_3$ (20 mg) in THF (500 μL) was added forming a homogeneous phase. The solution was stirred at room temperature overnight, then THF was evaporated under vacuum. To the dry NPs, a solvent mixture of MeOH/CHCl$_3$/Hexane was added, similar to the one used above for the QDs, yielding a turbid sample. Following centrifugation, the solvent was decanted, the sample was gently dried. The resulting precipitate was readily dispersed in water, then 2-3 rounds of centrifugation using a membrane filtration device (Amicon Ultra, 50 kD) were used to purify the AuNPs from excess unbound ligands and solubilized organics.

Example 20

Conjugation of QDs to Transferrin Via EDC Coupling

The QDs (12.5 μM, 40 μL) photoligated with a mixture of bis(LA)-PEG-OCH$_3$ and bis(LA)-PEG-COOH (85:15 in molar ratio), EDC (52 mM in DI water, 14.4 μL), NHS (87 mM in DI water, 17.3 μL) were mixed with 178.3 μL of 10 mM phosphate buffer (PB, pH 6.5) in a scintillation vial. The vial was wrapped with aluminum foil and the mixture was stirred at room temperature for 1 hr. Then 4 mL of 10 mM PB (pH 8.7) was added and the content was subsequently transferred to a membrane filtration device (Amicon Ultra, 50 kD), then one round of concentration/dilution was applied to remove excess EDC. The sample was concentrated to a final volume of ~100 μL, then NHS (87 mM in DI water, 9 μL), transferrin (2.4 mg) and 10 mM PB (pH 8.7) were added; the total volume of the reaction was maintained at 400 μL. The mixture was left to react at room temperature for 5 hours with constant stirring, then loaded onto a PD-10 desalting column (GE Healthcare) to remove unreacted transferrin and excess coupling reagents. The conjugates were characterized using absorption spectroscopy before testing them in cellular uptake measurements.

Example 21

Conjugation of QDs with Peptide (A42)

QDs photoligated with 5% and 10% bis(LA)-PEG-COOH were used to label a peptide with the sequence of GAS-GRIGFLRTAACA (M.W.~1449.4). This peptide has a C-terminal cysteine (C) at one end which was coupled to a maleimide-functionalized dye and a glycine residue (G) at the N-terminal was reacted with the COOH-QDs. It was synthesized manually using in situ neutralization cycles for Boc-solid-phase-peptide synthesis (Boc-SPPS) following procedures described in the literature. See Reference 85. Briefly, the synthesis was carried out using 0.2 mmol MBHA resin (4-Methylbenzhydrylamine, 0.40 mmol/g), 1.0 mmol of aminoacid, 1.0 mmol of HCTU (in a 0.4 M solution in DMF), and 1.5 mmol of DIEA. Coupling times were 20 min. Following chain assembly, the peptide was cleaved from the resin with HF and 10% of anisole for 1 hour at 0° C.

We provide the details for conjugating 5% COOH-QDs and peptide-Cy3 using carbodiimide chemistry. Briefly, in a scintillation vial, 5% COOH-QDs (6.6 µM, 38 µL) were diluted in 10 mM pH 6.5 PB (72 µL) and mixed with EDC (5.2 mM in 10 mM pH6.5 PB, 40 µL). The reaction mixture was stirred for 1 hour at room temperature (in the dark), followed by the addition of NHS (8.7 mM in 10 mM pH8.7 PB, 47 µL) and a solution of Cy3-labeled peptide (529 µM, 25 µL) in DMSO. 10 mM PB (pH8.7, 278 µL) was added to render the mixture basic. The reaction mixture was left stirring for 5 hours at room temperature, and the conjugates were purified using a PD-10 desalting column. The QD-peptide conjugates were characterized using the absorption and fluorescence spectroscopy. Conjugation of peptide-Cy3 to 10% COOH-QDs was carried out following the same protocol, except that the amount of coupling reagent and peptide-Cy3 were doubled in order to compensate for the higher number of carboxyl groups per QD and maintain the same molar ratio between acid groups and target peptide-Cy3 as above.

Example 22

Cell Culture

Hela cells were cultured in complete growth medium (Dulbecco's modified eagle's medium, DMEM, Corning Cellgro) supplemented with 4.5 g/L glucose, L-glutamine, sodium pyruvate, 1% (v/v) antibiotic-antimycotic 100× (Gibco), 1% (v/v) nonessential amino-acid solution 100× (Sigma), and 10% (v/v) fetal bovine serum (FBS, from Gibco). Cells were cultured in T25-flasks, incubated at 37° C. under 5% $CO_2$ atmosphere and subcultured every 2-4 days using trypsin-EDTA (Invitrogen).

Example 23

Cellular Delivery of QD-Tf Conjugates

The cells were seeded onto 18 mm circle micro-cover glasses placed into 24-well microtiter plates (CellStar, VWR), approximately $8 \times 10^4$ cells were seeded per well, and the plates were placed in an incubator at 37° C. overnight. Given amounts of bis(LA)-PEG-$OCH_3$-QDs and QD-Tf conjugates were measured and diluted into culture medium (DMEM without phenol red, Invitrogen) to the desired concentration (150 nM), and were subsequently added to the cell culture and incubated at 37° C. for 1 hr. Texas Red-Tf (40 µg/mL) was also added to the culture as efficient marker of the late endosomal compartments. After incubation, excess unbound QD-conjugates and Texas Red-Tf were removed by washing with phosphate-buffered saline (PBS, pH7.4) three times. For subsequent imaging, the cells were fixed with 3.7% paraformaldehyde in PBS at room temperature, and cell nuclei were stained in with DAPI dye (Invitrogen).

Example 24

Cellular Imaging

The epifluorescence images shown in FIG. 6 were collected using an Inverted Research Nikon Eclipse Ti Microscope equipped with a CoolSNAP HQ2 CCD color camera, available at the FSU Department of Chemistry and Biochemistry. The blue DAPI fluorescence was detected using a DAPI cube (with 340-380 nm excitation and 435-485 nm emission lines). The green QD fluorescence signal was detected using a GFP/EGFP cube (with 465-495 nm excitation and 515-555 nm emission lines). The Texas Red-Tf fluorescence was detected using a TEXAS RED HYQ cube (with 532-587 nm excitation and 608-683 nm emission lines).

Example 25

Coupling of the Peptide (A42) to Sulfo-Cy™ 3 Maleimide Mono-reactive Dye

We used the cysteine group at one end of the peptide with the sequence of GASGRIGFLRTAACA (MW~1449.4 g/mol) to couple with sulfo-Cy3 maleimide dye. Briefly, 0.1 mg of peptide (~69 nM) dissolved in 5-10 µL DMSO was first dispersed in 200 µL, of PBS (pH~7.8) in a glass vial. Then 0.0396 mg (2 times molar excess with respect to the peptide) of TCEP-HCl dissolved in 50 µl PBS was mixed and stirred for 15-20 min at room temperature under nitrogen atmosphere. A stock solution of Sulfo-Cy™ 3 maleimide mono-reactive dye (MW=766) was prepared by dissolving the dye in dry DMSO and then 0.26 mg of Sulfo-Cy3 maleimide dye (5 times molar excess with respect to the peptide) was added to the peptide solution followed by purging with nitrogen. The solution was stirred for 3 hours at room temperature; the dye coupled peptide was purified using HPLC.

Example 26

FRET Analysis of the Fluorescence Data from QD-peptide-dye Conjugates

The steady-state fluorescence spectra were collected on a Fluorolog-3 spectrometer (HORIBA Jobin Yvon Inc., Edison, N.J.) equipped with TBX PMT and air-cooled CCD camera detectors. All the steady-state PL spectra were collected using a narrow excitation line at 350 nm. The time-resolved (TR) PL decays were collected and analyzed with a time correlation single photon counting (TCSPC) system integrated into the Fluorolog-3. The sample excitation at 440 nm with a repetition rate of 1 MHz was provided by a pulsed NanoLED-440LH (100 ps, FWHM). The signal was detected with the TBX detector, with a resolution of ~0.1 ns. The PL decay profiles with time for the QD-peptide-Cy3 conjugates (limited to a narrow window centered at 510 nm) were fitted to a three-exponential function of the form:[1]

$$I(t) = A_1 e^{\frac{t}{\tau_1}} + A_2 e^{\frac{t}{\tau_2}} + A_3 e^{\frac{t}{\tau_3}} \quad (1)$$

where t is time and $A_i$ is a weighting parameter associated with each decay time, $\tau_i$. An average amplitude-weighted lifetime, $\tau_{avg}$, was extracted from the fit using Data Station software (Horiba Jovin-Yvon), with:

$$\tau_{avg} = \frac{\sum A_i \tau_i^2}{\sum A_i \tau_i} \quad (2)$$

The PL quenching efficiency, E, were extracted from the steady-state or time-resolved fluorescence data, using the expressions:[2]

$$E = 1 - \frac{F_{DA}}{F_D}, \text{ for steady-state fluorescence} \quad (3a)$$

$$\text{and } E = 1 - \frac{\tau_{DA}}{\tau_D}, \text{ for time-resolved fluorescence} \quad (3b)$$

where $F_D$ and $F_{DA}$ respectively represent the PL intensity of QDs alone and the QD-peptide-Cy3 conjugates, while $\tau_D$ and $\tau_{DA}$ represent the PL lifetime measured for QDs alone and QDs coupled with peptide-Cy3. Analysis of FRET data provided an additional estimate for the number of acceptors (dyes) around each QD donor. The energy transfer quenching efficiency within the Förster dipole-dipole model and assuming a centro-symmetric configuration for the QD-peptide-dye conjugates becomes:[1]

$$E_n = \frac{nR_0^6}{nR_0^6 + r^6} \quad (4)$$

where r represents the center-to-center separation distance between the central QD and dyes and $R_0$ is the Förster radius corresponding to $E_{n=1}=0.5$; $R_0$ is given by:

$$R_0 = \left(\frac{9000 \times \ln(10) \times k_p^2 Q_D I}{128\pi^5 n_D^4 N_A}\right)^{1/6} = 9.78 \times 10^3 (n_D^{-4} k_p^2 Q_D I)^{1/6} (\text{in Å}) \quad (5)$$

$R_0$ depends on the PL quantum yield of the donor, QD, the refractive index of the medium, $n_D$, the Avogadro's number, $N_A$, the dipole orientation parameter, $\kappa_p^2$, and the spectral overlap integral, I. A value of $\kappa_p^2=2/3$ was used for the orientation factor in our present configuration.[3] I is extracted from integration (over all wavelengths) of the spectral overlap function, $J(\lambda)=PL_{D\text{-}corr}(\lambda)\times\lambda^4\times\varepsilon_A(\lambda)$; where $PL_{D\text{-}corr}$ and $\varepsilon_A$ designate the normalized fluorescence spectrum of the donor and the extinction coefficient spectrum of the acceptor, respectively. For our system, using the experimental spectral overlap and a $Q_D$ value of ~18% yielded a value of $R_0 \approx 52$ Å.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A Compound 4 having the structure:

Compound 4

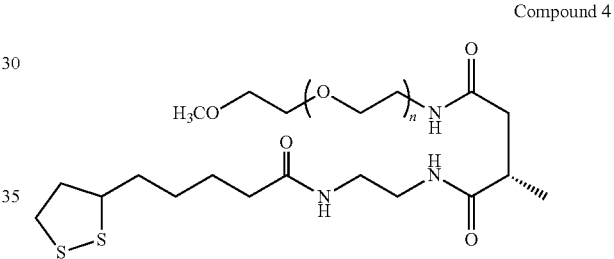

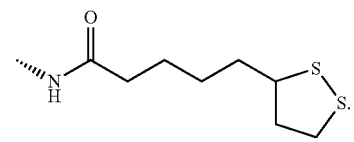

2. A Compound 7 having the structure:

Compound 7

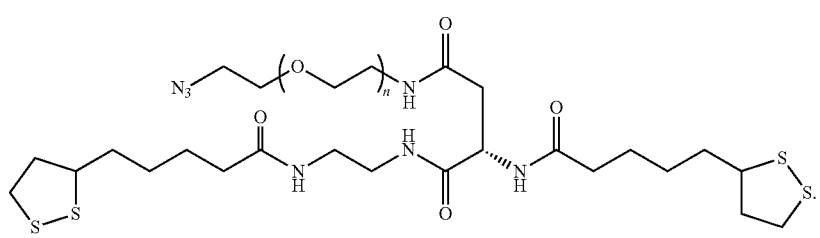

3. A Compound 8 having the structure:
Compound 8
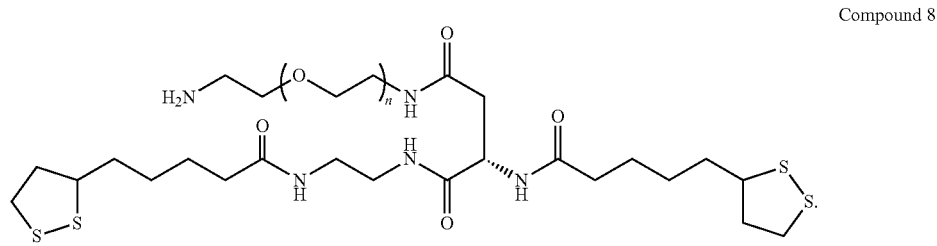
4. A Compound 9 having the structure:
Compound 9
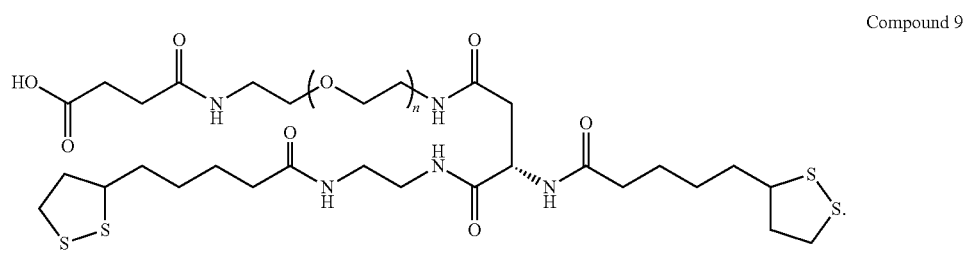
5. A Compound 11 having the structure:
Compound 11
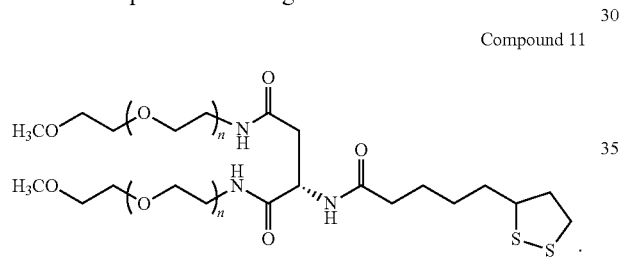
6. A Compound 13 having the structure:
Compound 13
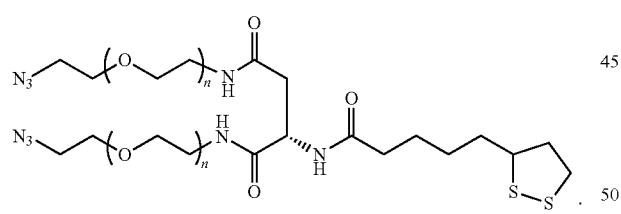
7. A Compound 14 having the structure:
Compound 14
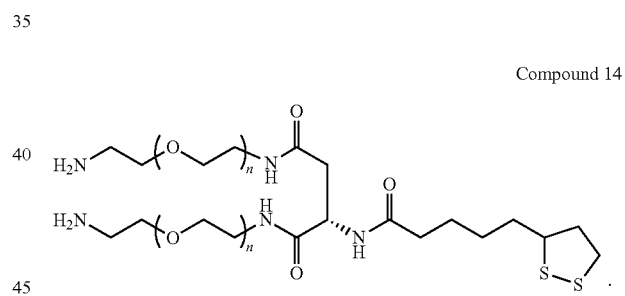
8. A Compound 15 having the structure:
Compound 15
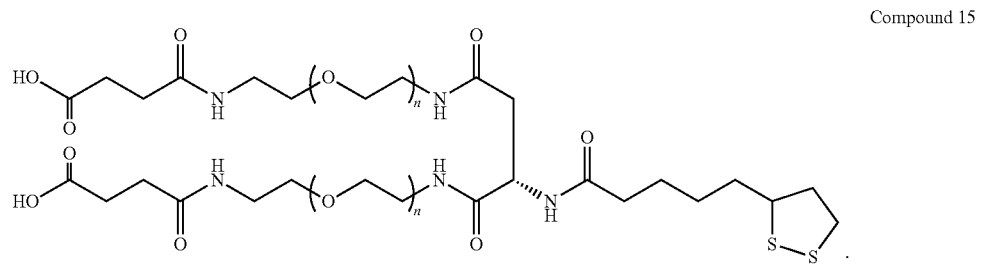

9. A composition comprising:
a nanoparticle comprising a material selected from the group consisting of $Fe_3O_4$, $Fe_2O_3$, FePt, Co, Mn-doped $Fe_3O_4$, CdSe/ZnS, InP/ZnS, PbS, CdTe, CoPt, FeCoPt, $CoFe_2O_4$, MnO, $Mn_3O_4$, $Co_3O_4$, FeO, Ni, $TiO_2$, $Al_2O_3$, CdSe, PbSe, $ZrO_2$, ZnO, Au, Ag, and graphene oxide; and
a capping layer comprising the compound 4 of claim 1.

10. A composition comprising:
a nanoparticle comprising a material selected from the group consisting of silicon, germanium, tin, silicon carbide, selenium, tellurium, boron nitride, boron phosphide, boron arsenide, aluminum nitride, gallium nitride, gallium arsenide, indium nitride, indium antimonide, cadmium selenide, cadmium sulfide, zinc oxide, zinc sulfide, and lead sulfide; and
a capping layer comprising the compound 4 of claim 1.

11. A composition comprising:
a nanoparticle comprising a material selected from the group consisting of gold (Au), silver (Ag), platinum (Pt), copper (Cu), nickel (Ni), and alloys thereof; CdSe, CdS, CdSeS, CdTe, InAs, InP, GaAs, PbSe, PbS, HgSe, HgTe, $AgInS_2$, $CuInS_2$, CdSeTe, ZnCdSe, and ZnCdTe; and
a capping layer comprising the compound 4 of claim 1.

* * * * *